US012760071B2

(12) United States Patent
Collier et al.

(10) Patent No.: US 12,760,071 B2
(45) Date of Patent: Oct. 13, 2026

(54) SUPRAMOLECULAR POLYPEPTIDE COMPOSITIONS AND METHODS OF MAKING AND USING THE SAME

(71) Applicant: Duke University, Durham, NC (US)

(72) Inventors: Joel Collier, Durham, NC (US); Nicole Votaw, Durham, NC (US)

(73) Assignee: Duke University, Durham, NC (US)

( * ) Notice: Subject to any disclaimer, the term of this patent is extended or adjusted under 35 U.S.C. 154(b) by 892 days.

(21) Appl. No.: 17/608,443

(22) PCT Filed: May 4, 2020

(86) PCT No.: PCT/US2020/031351
§ 371 (c)(1),
(2) Date: Nov. 2, 2021

(87) PCT Pub. No.: WO2020/223730
PCT Pub. Date: Nov. 5, 2020

(65) Prior Publication Data

US 2022/0194989 A1 Jun. 23, 2022

Related U.S. Application Data

(60) Provisional application No. 62/841,972, filed on May 2, 2019.

(51) Int. Cl.
*C07K 14/00* (2006.01)
*A61K 38/00* (2006.01)
*A61K 38/16* (2006.01)

(52) U.S. Cl.
CPC ............ *C07K 14/001* (2013.01); *A61K 38/16* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,207,749 B1 | 3/2001 | Mayes et al. | |
| 6,514,938 B1 | 2/2003 | Gad et al. | |
| 7,560,100 B2 | 7/2009 | Pinchasi et al. | |
| 7,655,221 B2 | 2/2010 | Rasmussen et al. | |
| 9,200,082 B2 * | 12/2015 | Collier | C07K 14/78 |
| 9,241,987 B2 * | 1/2016 | Collier | A61K 47/646 |
| 9,849,174 B2 * | 12/2017 | Collier | A61K 39/015 |
| 10,596,238 B2 * | 3/2020 | Collier | A61K 39/0005 |
| 11,246,924 B2 * | 2/2022 | Collier | C07K 14/001 |
| 2007/0087114 A1 | 4/2007 | Chilkoti et al. | |
| 2009/0191173 A1 | 7/2009 | Eisenbach-Schwartz et al. | |
| 2010/0292130 A1 | 11/2010 | Skerra et al. | |
| 2014/0193827 A1 | 7/2014 | Schwartz et al. | |
| 2014/0273148 A1 | 9/2014 | Collier et al. | |
| 2016/0074509 A1 | 3/2016 | Collier et al. | |
| 2022/0362159 A1 | 11/2022 | Collier et al. | |
| 2022/0387605 A1 * | 12/2022 | Collier | A61K 47/42 |

FOREIGN PATENT DOCUMENTS

| | | |
|---|---|---|
| EP | 2173890 A1 | 4/2010 |
| WO | 2008039483 A2 | 4/2008 |
| WO | 2008155134 A1 | 12/2008 |
| WO | 2009091518 A2 | 7/2009 |
| WO | 2011063264 A1 | 5/2011 |
| WO | 2012177868 A1 | 12/2012 |
| WO | 2017173398 A1 | 10/2017 |
| WO | 2019018572 A1 | 1/2019 |

OTHER PUBLICATIONS

U.S. Appl. No. 18/693,805, filed Sep. 20, 2022, Collier; Joel H.*
GenBank Accession No. XP_064100865, 2 pages (2024) (Year: 2024).*
Lee et al., Adv. Sci. 6:15 pages (first available Nov. 2018) (Year: 2018).*
Towfic F, Funt JM, Fowler KD, Bakshi S, Blaugrund E, Artyomov MN, Hayden MR, Ladkani D, Schwartz R, Zeskind B. Comparing the biological impact of glatiramer acetate with the biological impact of a generic. PLoS One. Jan. 8, 2014;9(1):e83757.
Varkony et al. The glatiramoid class of immunomodulator drugs. Expert Opin Pharmacother 10(4):657-68, 2009.
Meira PL, Heystek HC, Wormmeester J, Wierenga EA, Kapsenberg ML. Glatiramer Acetate (Copolymer-1, Copaxone) Promotes Th2 Cell Development and Increased IL-10 Production Through Modulation of Dendritic Cells. The Journal of Immunology. 2003;170(9):4483-4488.
Weber MS, Hohlfeld R, Zamvil SS. Mechanism of action of glatiramer acetate in treatment of multiple sclerosis. Neurotherapeutics. 2007;4(4):647-653.
Weber MS, Prod'homme T, Youssef S, et al. Type II monocytes modulate T cell-mediated central nervous system autoimmune disease. Nat Med. 2007;13(8):935-943.
Wen, Y.; Collier, J. H., Supramolecular peptide vaccines: tuning adaptive immunity. Current opinion in immunology 2015, 35, 73-79.
Wu, Y.; Norberg, P. K.; Reap, E. A.; Congdon, K. L.; Fries, C. N.; Kelly, S. H.; Sampson, J. H.; Conticello, V. P.; Collier, J. H., A Supramolecular Vaccine Platform Based on α-Helical Peptide Nanofibers. ACS Biomaterials Science & Engineering 2017, 3 (12), 3128-3132.
Xu H, Hu C, Gong R, et al. Evaluation of a Novel Chimeric B Cell Epitope-Based Vaccine against Mastitis Induced by Either *Streptococcus agalactiae* or *Staphylococcus aureus* in Mice. Clin Vaccine Immunol. 2011;18(6):893-900.
Xu K, Acharya P, Kong R, et al. Epitope-based vaccine design yields fusion peptide-directed antibodies that neutralize diverse strains of HIV-1. Nat Med. Jun. 2018:1-19.

(Continued)

*Primary Examiner* — Thea D' Ambrosio
(74) *Attorney, Agent, or Firm* — Quarles & Brady, LLP

(57) ABSTRACT

The present disclosure provides a supramolecular (self-assembling) polypeptide complex that comprises a plurality of randomized polyamino acids that self-assemble into nanofibers and methods of making and using same.

13 Claims, 28 Drawing Sheets
(5 of 28 Drawing Sheet(s) Filed in Color)
Specification includes a Sequence Listing.

(56) References Cited

OTHER PUBLICATIONS

Yenkoidiok-Douti, L.; Jewell, C. M., Integrating Biomaterials and Immunology to Improve Vaccines Against Infectious Diseases. ACS Biomaterials Science & Engineering 2020.
Zhang L. The Immunogenicity and Immunoprotection of VBP3 Multi-epitope Vaccine Targeting Angiogenesis and Tumor Inhibition in Lung Cancer-Bearing Mice. International Journal of Peptide Research and Therapeutics. 2019;25 (1):215-225.
Zieglmayer P, Focke-Tejkl M, Schmutz R, et al. Mechanisms, safety and efficacy of a B cell epitope-based vaccine for immunotherapy of grass pollen allergy. EBIOM. 2016;11(C):43-57.
Adar Y, Singer Y, Levi R, et al. A universal epitope-based influenza vaccine and its efficacy against H5N1. Vaccine. 2009;27(15):2099-2107.
Aharoni R, Eilam R, Stock A, et al. Glatiramer acetate reduces Th-17 inflammation and induces regulatory T-cells in the CNS of mice with relapsing-remitting or chronic EAE. Journal of Neuroimmunology. 2010;225(1-2):100-111.
Aharoni R. Immunomodulatory Therapeutic Effect of Glatiramer Acetate on Several Murine Models of Inflammatory Bowel Disease. Journal of Pharmacology and Experimental Therapeutics. 2006;318(1):68-78.
Aharoni R. The mechanism of action of glatiramer acetate in multiple sclerosis and beyond. Autoimmunity Reviews. 2013;12(5):543-553.
Alexander J, Sidney J, Southwood S, et al. Development of High Potency Universal DR-Restricted Helper Epitopes by Modification of High Affinity DR-Blocking Peptides. Immunity. 1994;1:751-761.
Banskota et al. "Long circulating genetically encoded intrinsically disordered zwitterionic polypeptides for drug delivery." Biomaterials vol. 192 (2019): 475-485.
Banskota S, Saha S, Bhattacharya J, Kirmani N, Yousefpour P, Dzuricky M, Zakharov N, Li X, Spasojevic I, Young K, Chilkoti A. Genetically Encoded Stealth Nanoparticles of a Zwitterionic Polypeptide-Paclitaxel Conjugate Have a Wider Therapeutic Window than Abraxane in Multiple Tumor Models. Nano Lett. Apr. 8, 2020;20(4):2396-2409.
Blanchette F, Neuhaus O. Glatiramer Acetate. J Neurol. 2008;255(S1):26-36.
Butovsky O, Koronyo-Hamaoui M, Kynis G, et al. Glatiramer acetate fights against Alzheimer's disease by inducing dendritic-like microglia expressing insulin-like growth factor 1. PNAS. 2006;103(31):11784-11789.
Chen J, Pompano RR, Santiago FW, et al. The use of self-adjuvanting nanofiber vaccines to elicit high-affinity B cell responses to peptide antigens without inflammation. Biomaterials. 2013;34(34):8776-8785.
Duda Pw, Schmied MC, Cook SL, Krieger JI, Hafler DA. Glatiramer acetate (Copaxone®) induces degenerate, Th2-polarized immune responses in patients with multiple sclerosis. J Clin Invest. 2000; 105(7):967-976.
Elliott SL, Suhrbier A, Miles JJ, et al. Phase I Trial of a CD8+ T-Cell Peptide Epitope-Based Vaccine for Infectious Mononucleosis. JVI. 2008;82(3):1448-1457.
Fremont DH, Hendrickson WA, Marrack P, Kappler J. Structures of an MHC Class II molecule with covalently bound single peptides. Science. 1996;272(5264).
Gasiorowski JZ, Collier JH. Directed Intermixing in Multicomponent Self-Assembling Biomaterials. Biomacromolecules. 2011;12(10):3549-3558. doi:10.1021/bm200763y.
Grandi A, Fantappiè L, Irene C, et al. Vaccination With a FAT1-Derived B Cell Epitope Combined With Tumor-Specific B and T Cell Epitopes Elicits Additive Protection in Cancer Mouse Models. Front Oncol. 2018;8:207-214.
Gupta RK. Aluminum compounds as vaccine adjuvants. Advanced Drug Delivery Reviews. 1998;32:155-172.
Bachmann MF et al. The Influence of Antigen Organization on B Cell Responsiveness. Science. 1993;262 (5138):1448-1451.
Hudalla GA, Sun T, Gasiorowski JZ, Han H, Tian YF, Chong AS, Collier JH. Gradated assembly of multiple proteins into supramolecular nanomaterials. Nat Mater. Aug. 2014;13(8):829-36.
Hurtgen BJ, Hung C-Y, Ostroff GR, Levitz SM, Cole GT. Construction and Evaluation of a Novel Recombinant T Cell Epitope-Based Vaccine against Coccidioidomycosis. Deepe GS Jr., ed. Infect Immun. 2012;80(11):3960-3974.
International Search Report and Written Opinion for International Patent Application No. PCT/US2020/031351, dated Oct. 13, 2020.
International Search Report and Written Opinion for International Patent Application No. PCT/US2020/053095, dated Feb. 25, 2021.
Jin X, Newman MJ, De-Rosa S, et al. A novel HIV T helper epitope-based vaccine elicits cytokine-secreting HIV-specific CD4+ T cells in a Phase I clinical trial in HIV-uninfected adults. Vaccine. 2009;27(50):7080-7086.
Kelly SH, Shores LS, Votaw NL, Collier JH. Biomaterial strategies for generating therapeutic immune responses. Adv Drug Deliv Rev. May 15, 2017;114:3-18.
Kelly, S. H.; Wu, Y.; Varadhan, A. K.; Curvino, E. J.; Chong, A. S.; Collier, J. H., Enabling sublingual peptide immunization with molecular self-assemblies. Biomaterials 2020, 119903.
Kondamudi et al. Drugs as causative agents and therapeutic agents in inflammatory bowel disease. Acta Pharmaceutica Sinica B 3(5):289-296, 2013.
Landa G, Butovsky O, Shoshani J, Schwartz M, Pollack A. Weekly Vaccination with Copaxone (Glatiramer Acetate) as a Potential Therapy for Dry Age-Related Macular Degeneration. Current Eye Research. 2009;33(11-12):1011-1013.
Lee JS, Campbell HD, Kozak CA, Young IG. The IL-4 and IL-5 Genes are Closely Linked and Are Part of a Cytokine Gene Cluster on Mouse Chromosome 11. 1989;15(2):143-152.
Li H-B, Zhang J-Y, He Y-F, et al. Systemic immunization with an epitope-based vaccine elicits a Th1-biased response and provides protection against Helicobacter pylori in mice. Vaccine. 2012;31(1):120-126.
Mahdavi M, Moreau V, Kheirollahi M. Identification of B and T cell epitope based peptide vaccine from IGF-1 receptor in breast cancer. Journal of Molecular Graphics and Modelling. 2017;75:316-321.
Melis et al., Crohn's-like ileo-colitis in patients affected by glycogen storage disease lb: two years' follow-up of patients with a wide spectrum of gastrointestinal signs. Acta Paediatr 92(12):1415-21, 2003.
Mora-Solano C, Wen Y, Han H, et al. Active immunotherapy for TNF-mediated inflammation using self-assembled peptide nanofibers. Biomaterials. 2017;149:1-11.
Mountford AP, Fisher A, Wilson RA. The profile of IgG1 and IgG2a antibody responses in mice exposed to Schistosoma mansoni. Parasite Immunology. 1994;16:521-527.
Moutaftsi M, Bui H-H, Peters B, et al. Vaccinia virus-specific CD4+ T cell responses target a set of antigens largely distinct from those targeted by CD8+ T cell responses. The Journal of Immunology. 2007;178(11):6814-6820.
Neuhaus O, Farina C, Yassouridis A, et al. Multiple sclerosis: Comparison of copolymer-1-reactive T cell lines from treated and untreated subjects reveals cytokine shift from T helper 1 to T helper 2 cells. Proc Natl Acad Sci USA. 2000;97(13):7452-7457.
Oany A, Pervin T, Emran A. Design of an epitope-based peptide vaccine against spike protein of human coronavirus: an in silico approach. DDDT. Aug. 2014:1139-11.
Ohagan DT, MacKichan ML, Singh M. Recent developments in adjuvants for vaccines against infectious diseases. Biomolecular Engineering. 2001;18:69-75.
Onodi F, Maherzi-Mechalikh C, Mougel A, et al. High Therapeutic Efficacy of a New Survivin LSP-Cancer Vaccine Containing CD4+ and CD8+ T-Cell Epitopes. Front Oncol. 2018;8:517.
Philpott et al. Drug-induced gastrointestinal disorders. Frontline Gastroenterology 5(1):49-57, 2014.
Pompano RR, Chen J, Verbus EA, et al. Titrating T-Cell Epitopes within Self-Assembled Vaccines Optimizes CD4+ Helper T Cell and Antibody Outputs. Adv Healthcare Mater. 2014;3(11):1898-1908.
Reick C PhD, MD GE, PhD TT, et al. Expression of brain-derived neurotrophic factor in astrocytes—Beneficial effects of glatiramer

(56) References Cited

OTHER PUBLICATIONS acetate in the R6/2 and YAC128 mouse models of Huntington's disease. Experimental Neurology. 2016;285(Part A):12-23.

Rudra JS, Tian YF, Jung JP, Collier JH. A self-assembling peptide acting as an immune adjuvant. Proc Natl Acad Sci USA. 2010;107(2):622-627.

Rudra, J. S.; Sun, T.; Bird, K. C.; Daniels, M. D.; Gasiorowski, J. Z.; Chong, A. S.; Collier, J. H., Modulating adaptive immune responses to peptide self-assemblies. Acs Nano 2012, 6 (2), 1557-1564.

Schellekens et al. The therapeutic equivalence of complex drugs. Regul Toxicol Pharmacol 59(1):176-83, 2011.

Seroski and Hudalia , Self-Assembled Peptide and Protein Nanofibers for Biomedical Applications, Chapter 19 In Biomedical Applications of Functionalized Nanomaterials, (2018) 569-598.

Sloan-Lancaster J, Allen PM. Altered peptide ligand-induced partial T cell activation: molecular mechanisms and role in T cell biology. Annu Rev Immunol. 1996;14:1-27.

Sohaebuddin SK, Thevenot PT, Baker D, Eaton JW, Tang L. Nanomaterial cytotoxicity is composition, size, and cell type dependent. Particle and Fibre Toxicology. 2010;7(22).

Sun, T.; Han, H.; Hudalla, G. A.; Wen, Y.; Pompano, R. R.; Collier, J. H., Thermal stability of self-assembled peptide vaccine materials. Acta biomaterialia 2016, 30, 62-71.

Teitelbaum D, Arnon R, Sela M. Copolymer 1: from basic research to clinical application. Cell Mol Life Sci. Jan. 1997;53(1):24-8.

Teitelbaum D, Brenner T, Abramsky O, Aharoni R, Sela M, Arnon R. Antibodies to glatiramer acetate do not interfere with its biological functions and therapeutic efficacy. Mult Scler. 2003;9(6):592-599.

Teitelbaum D, Meshorer A, Hirshfeld T, Arnon R, Sela M. Suppression of experimental allergic encephalomyelitis by a synthetic polypeptide. Eur J Immunol. 1971;1(4):242-248.

* cited by examiner a

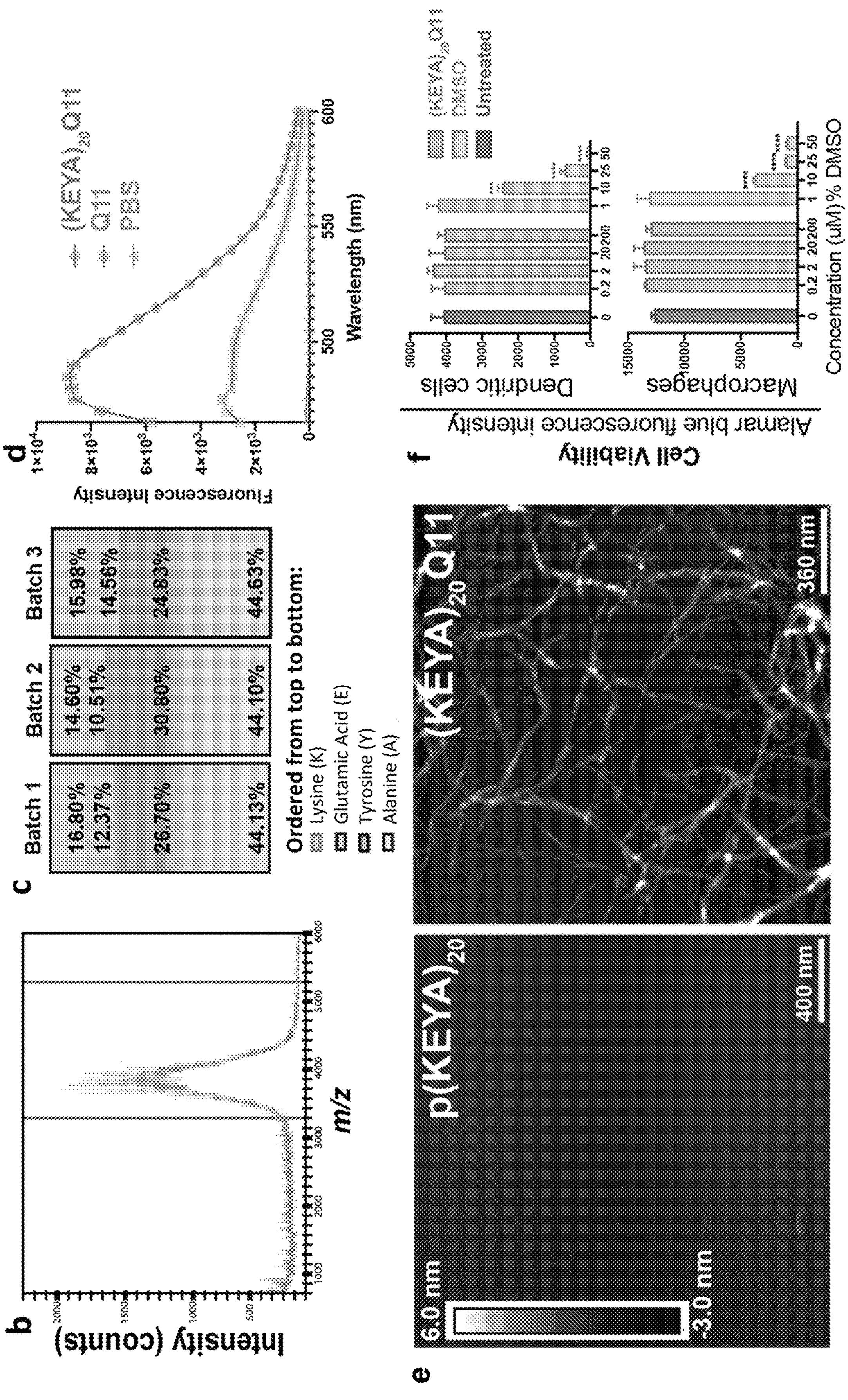
FIGURE 3-continued a b
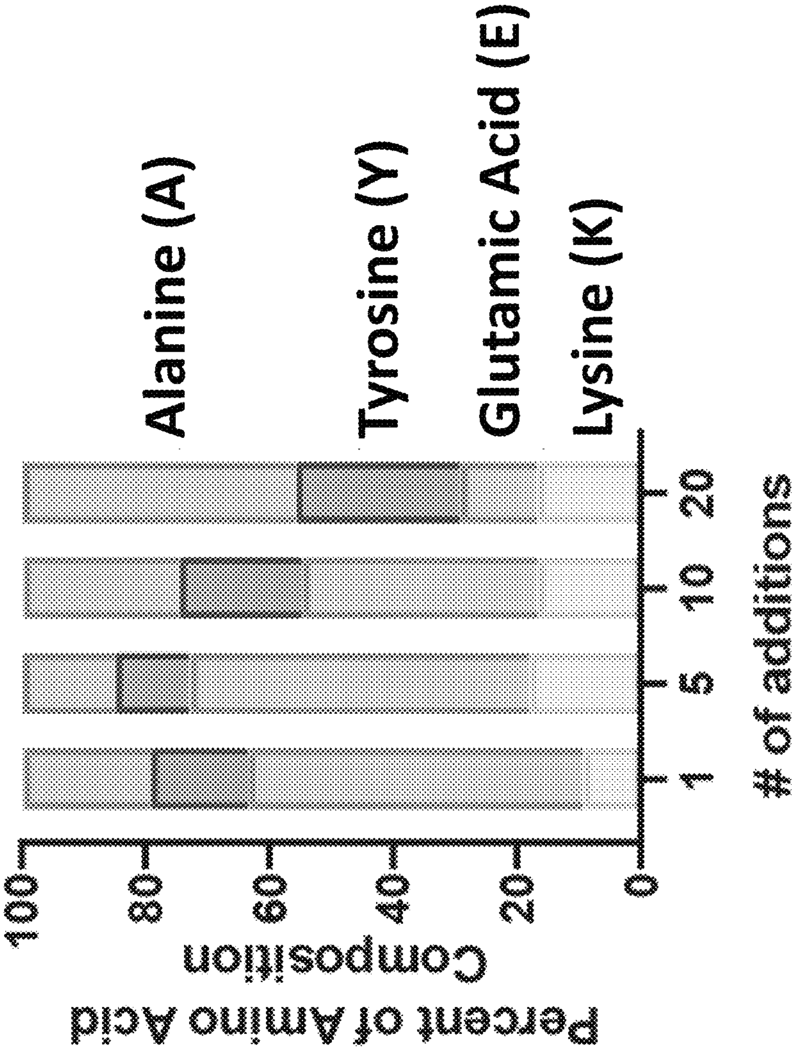
FIGURE 4-continued

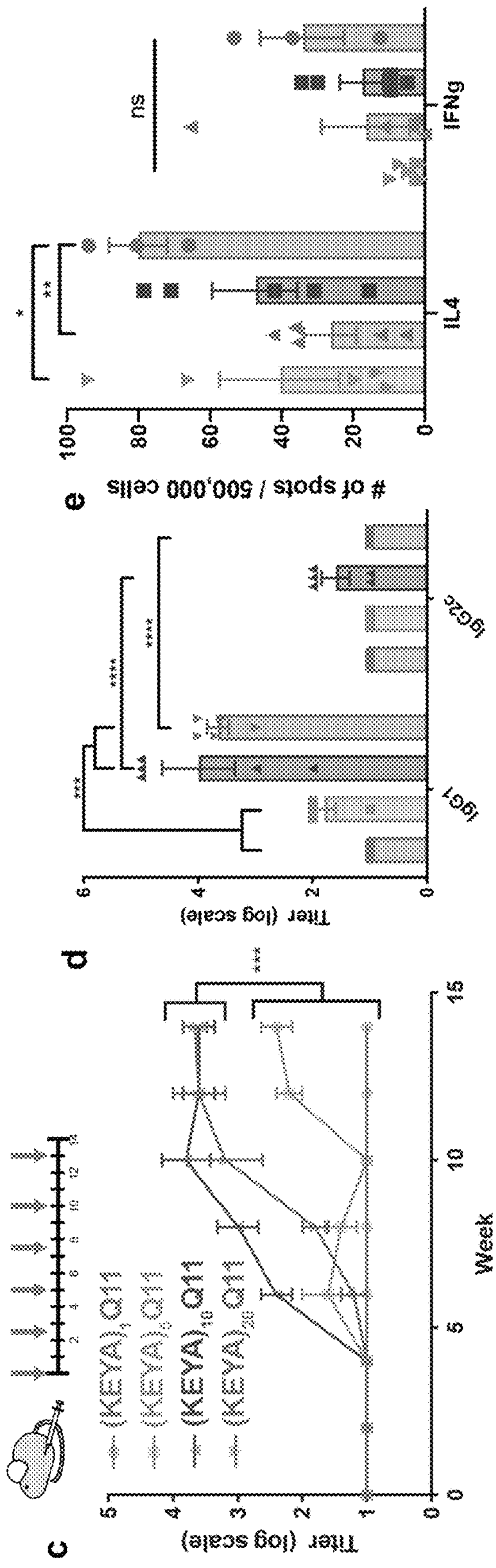
FIGURE 4-continued

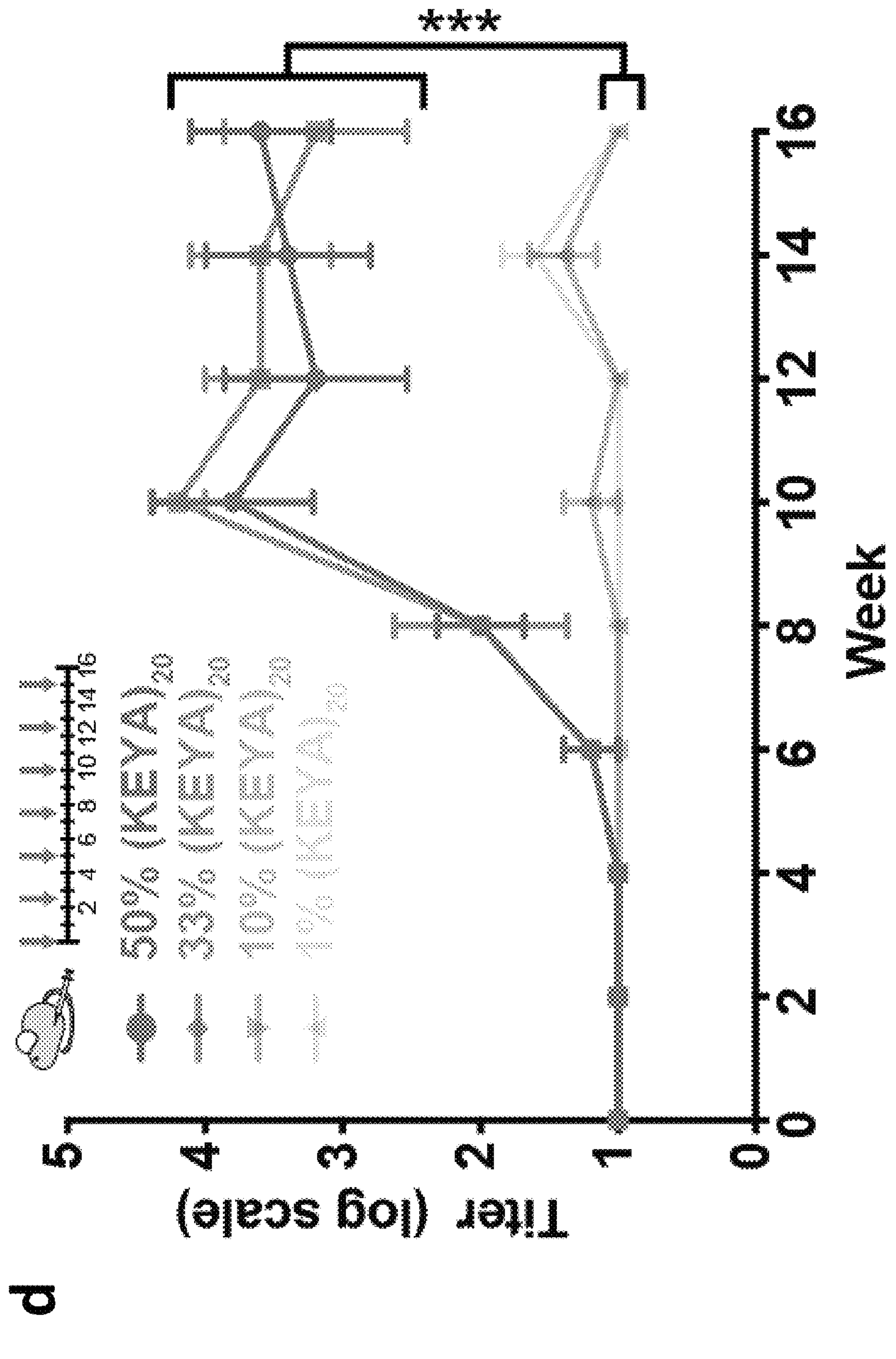
FIGURE 5-continued

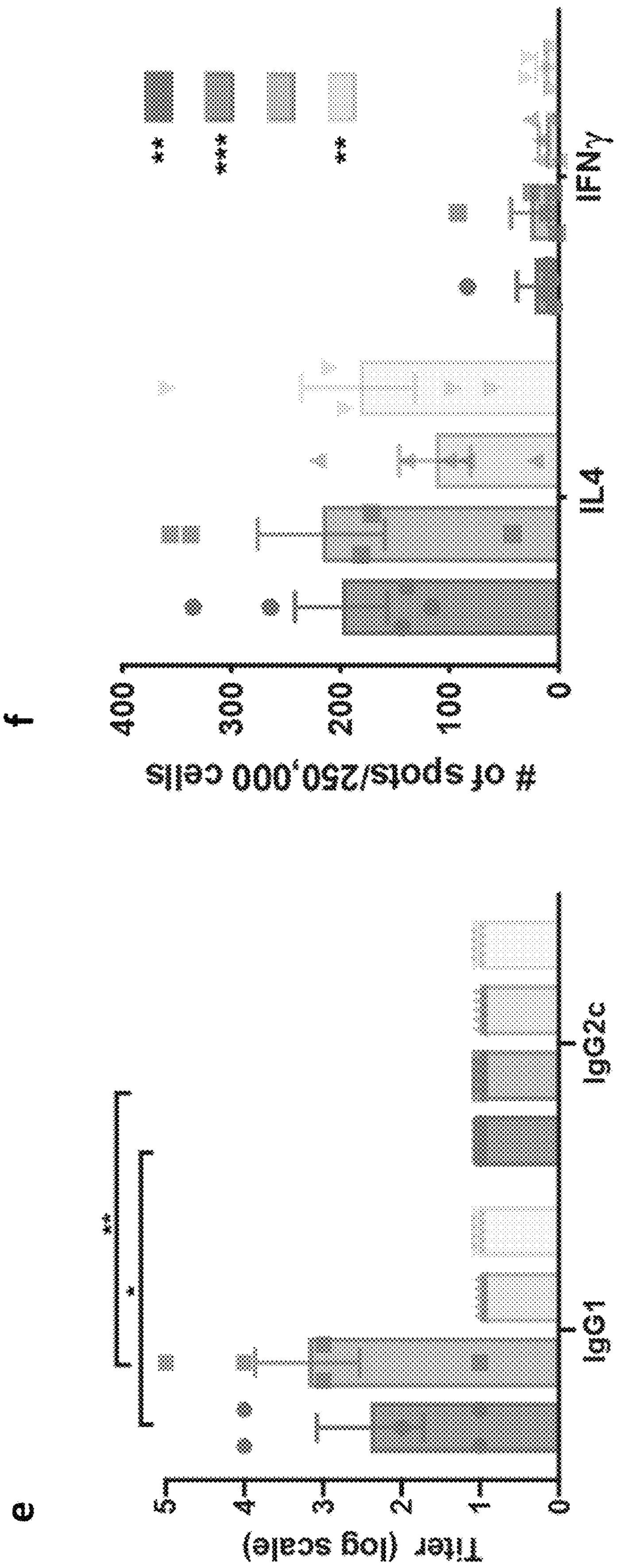
FIGURE 5-continued

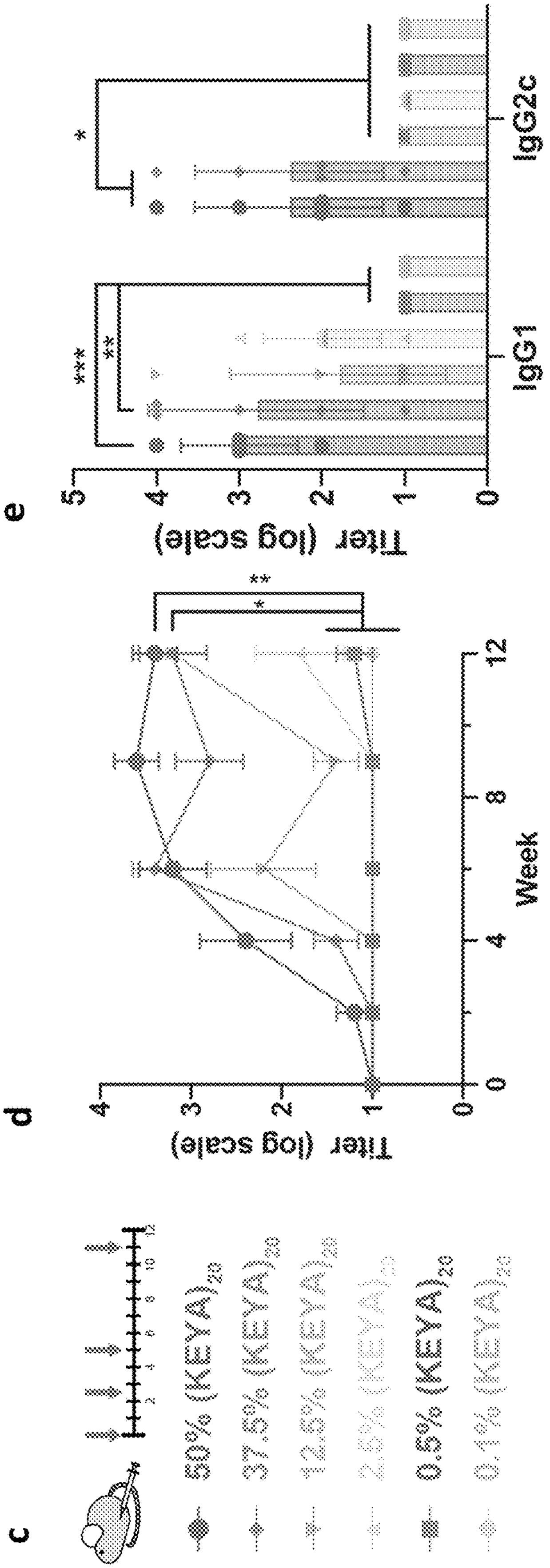
FIGURE 6-continued

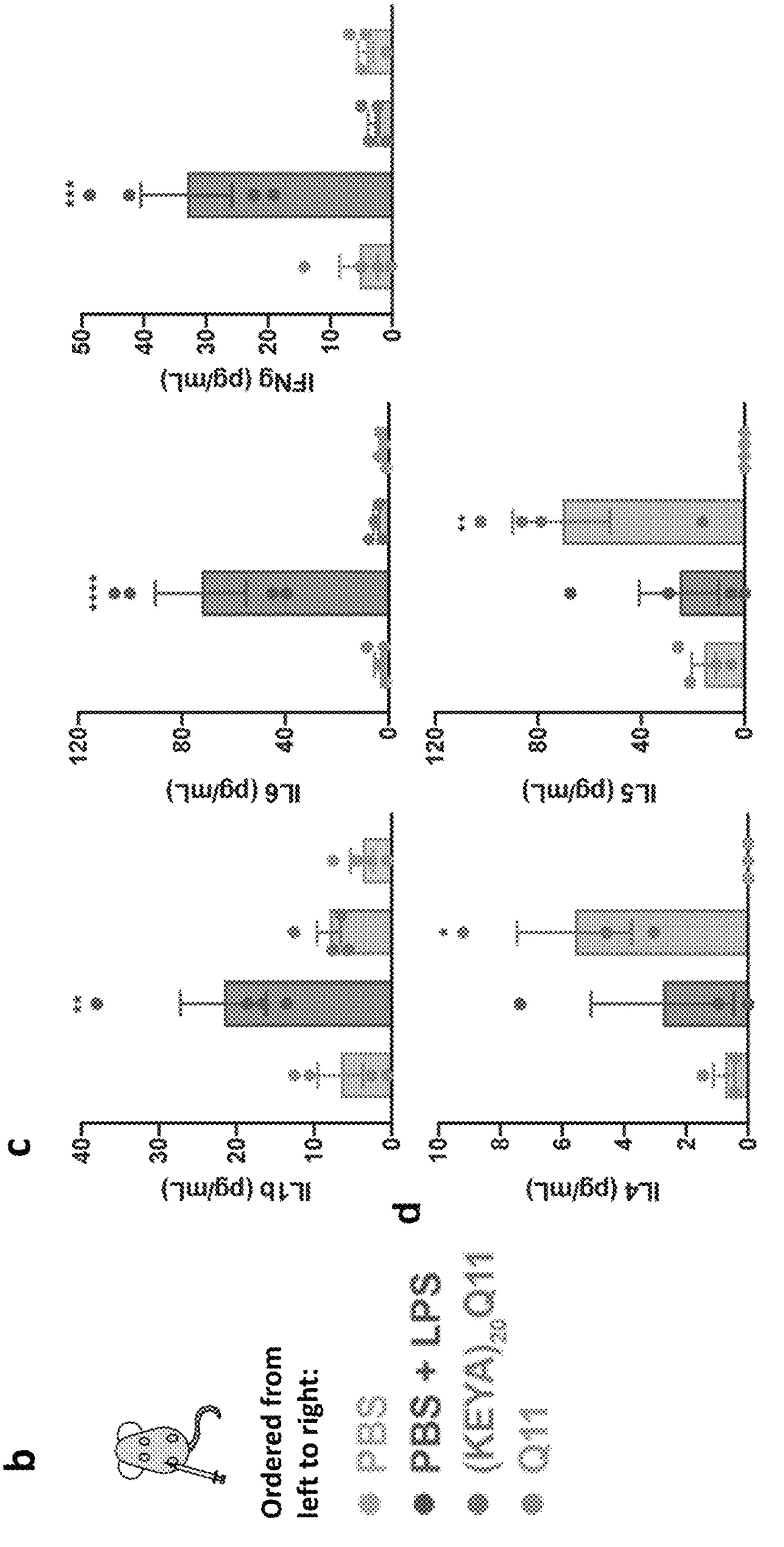
FIGURE 7-continued

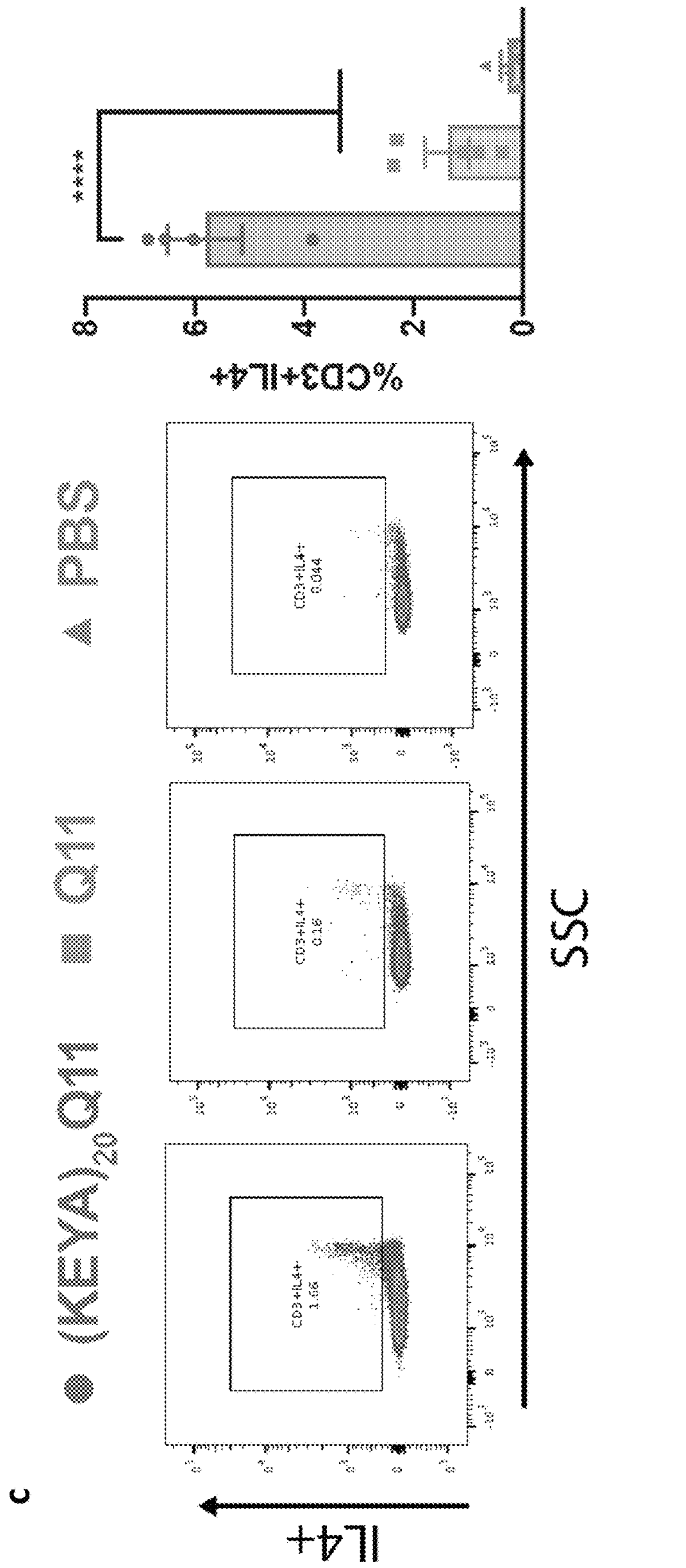
FIGURE 8-continued

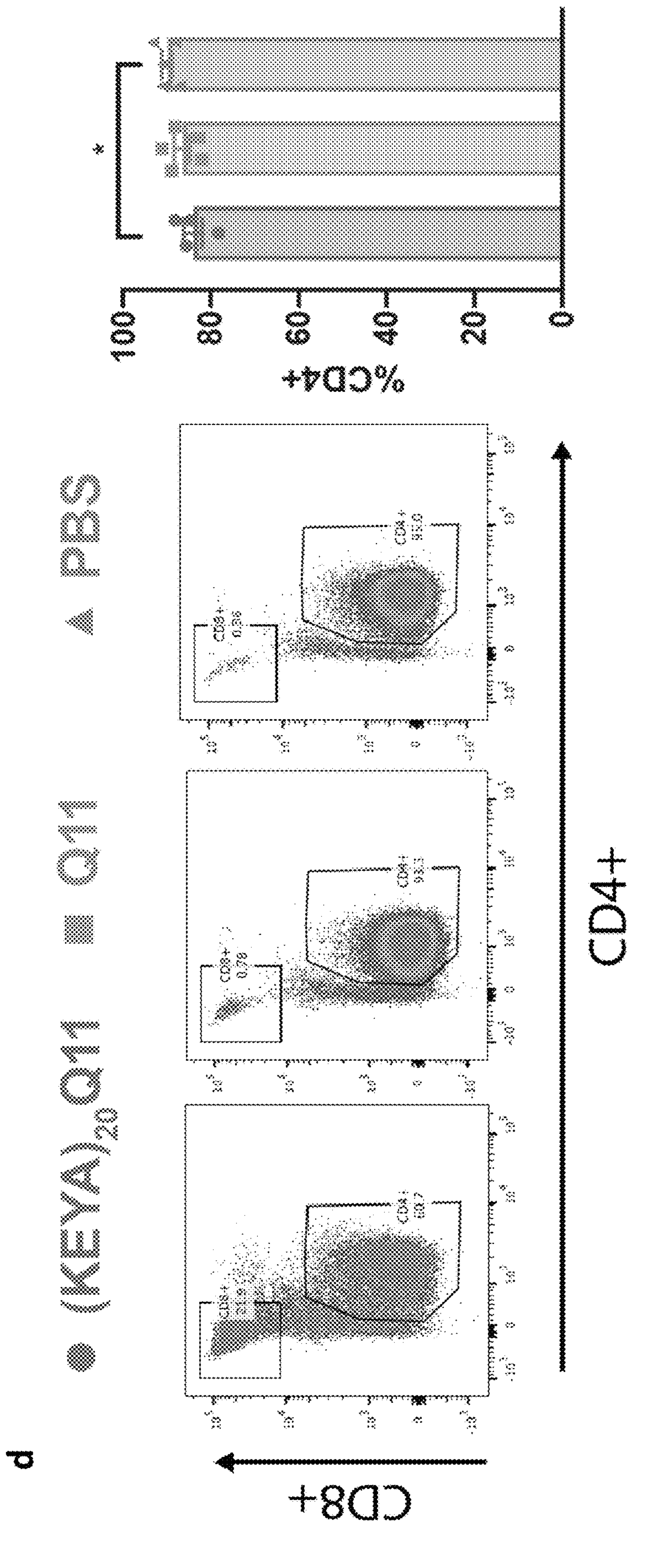
FIGURE 8-continued

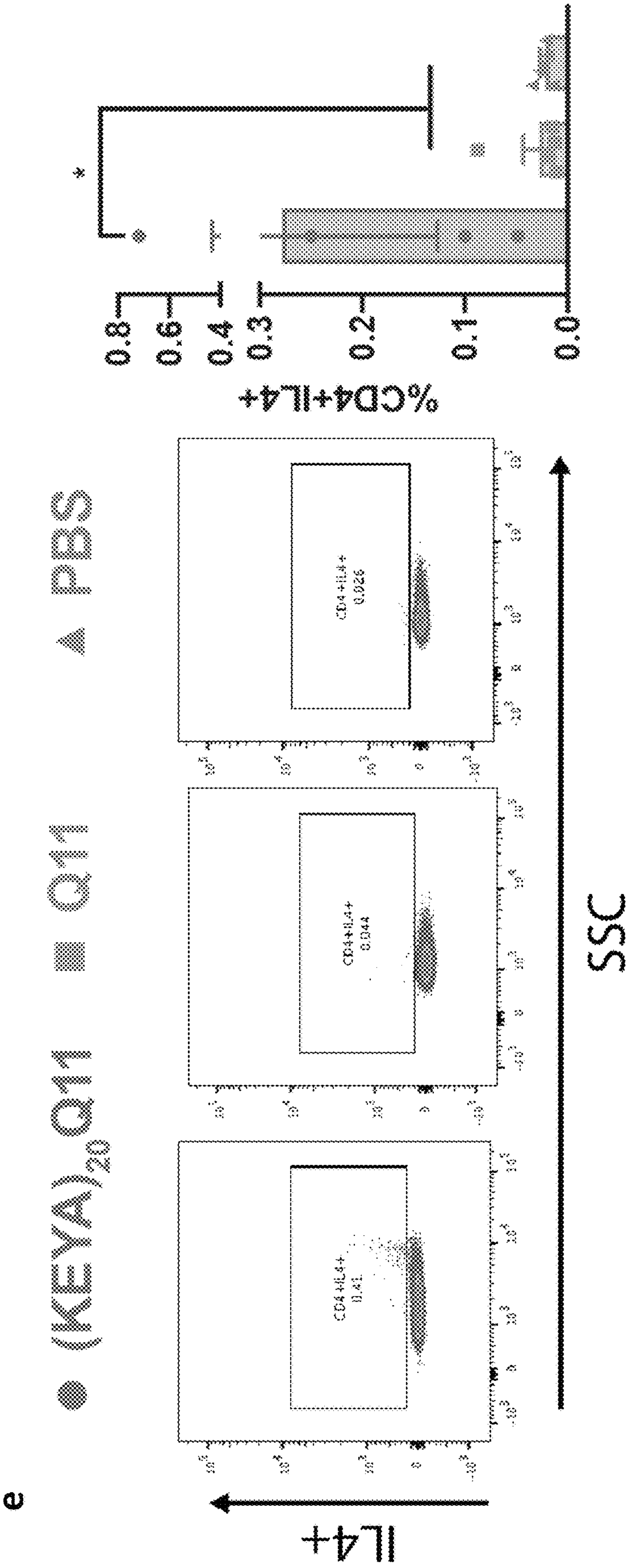
FIGURE 8-continued

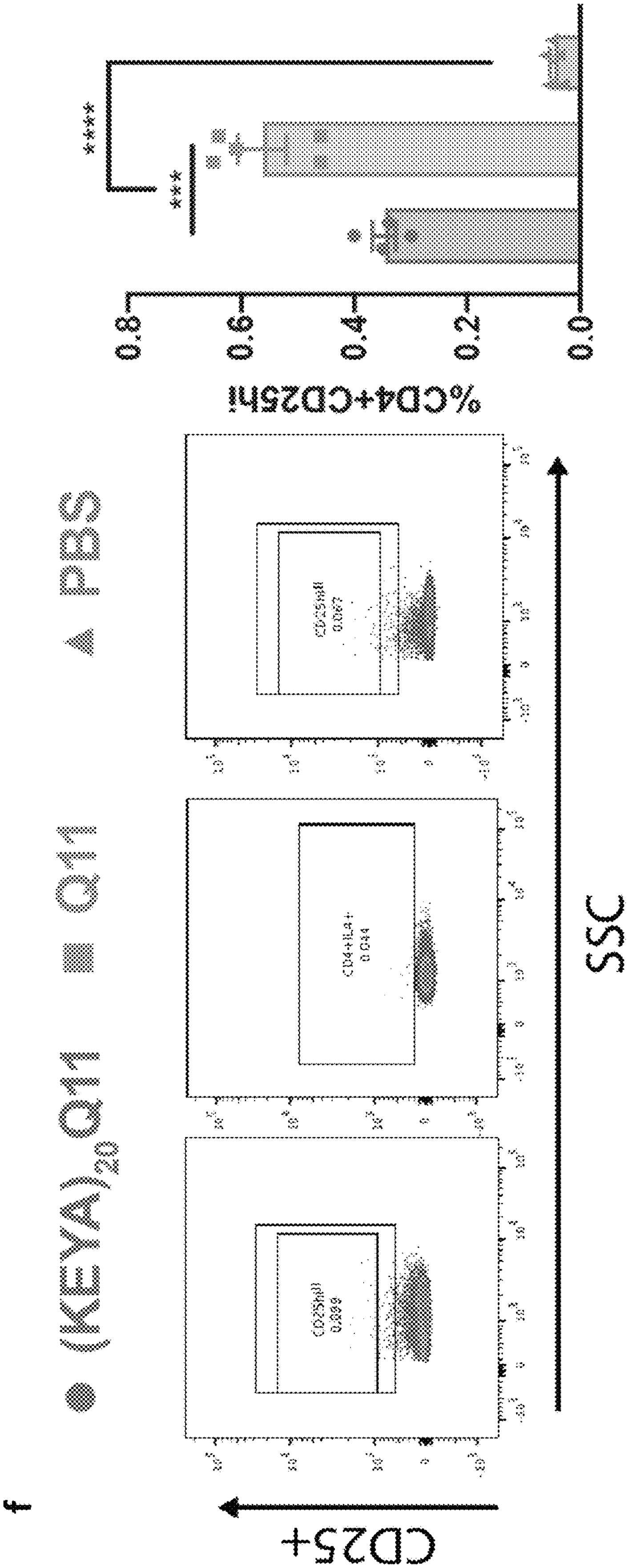
FIGURE 8-continued

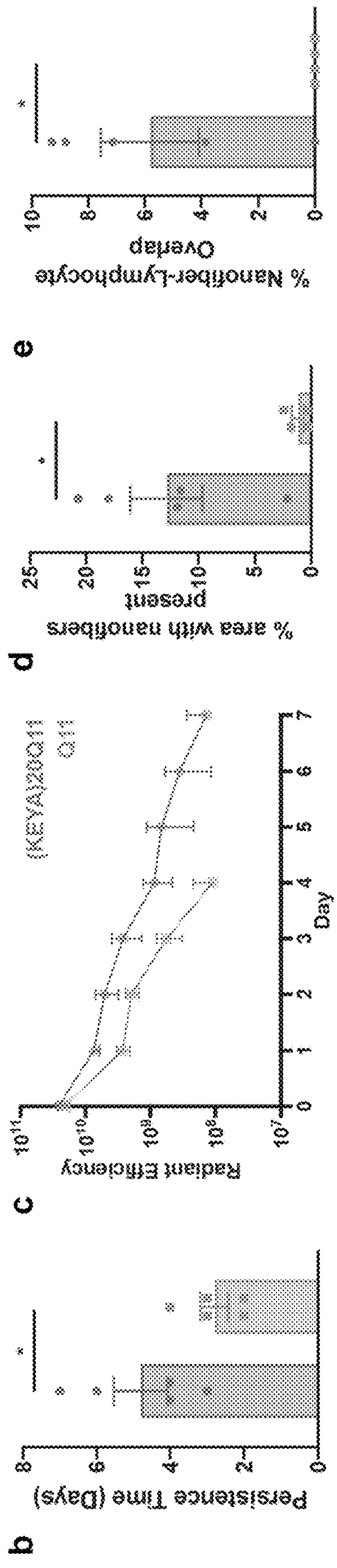
FIGURE 9-continued

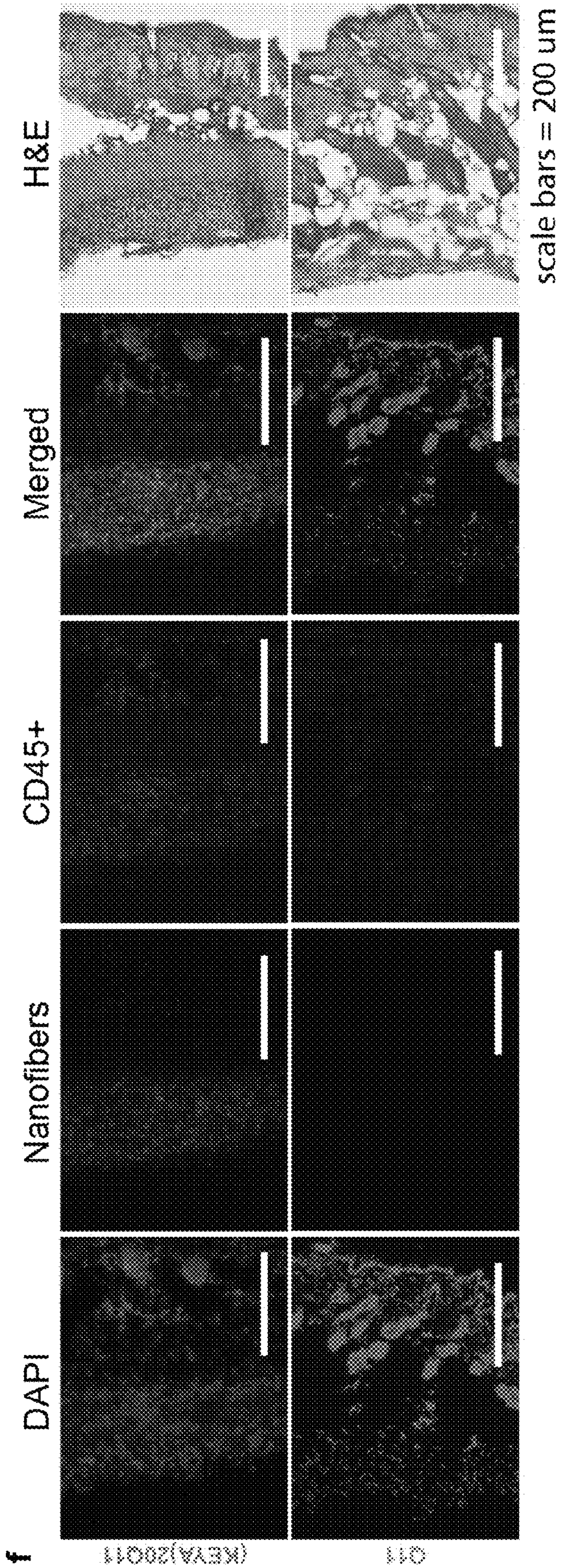
FIGURE 9-continued a

```
function [ K, E, Y, A ] = AAAmolarratios(k, e, y, a, F)
% To calculate molar ratios of K, E, Y, and A from Amino Acid Analysis
% e = E/Q combined, need to separate just E from Q11
% k also needs to be separated from Q11
% use F to determine molar amount of Q11 because it is not in KEYA
EQ = (7/3)*F;
molarE = e – EQ;
KQ = F/3;
molarK = k – KQ;
totalMoles = molarE + molarK + y + a;
K = molarK/totalMoles;
E = molarE/totalMoles;
Y  y/totalMoles;
A = a/totalMoles;
end
```

FIGURE 10

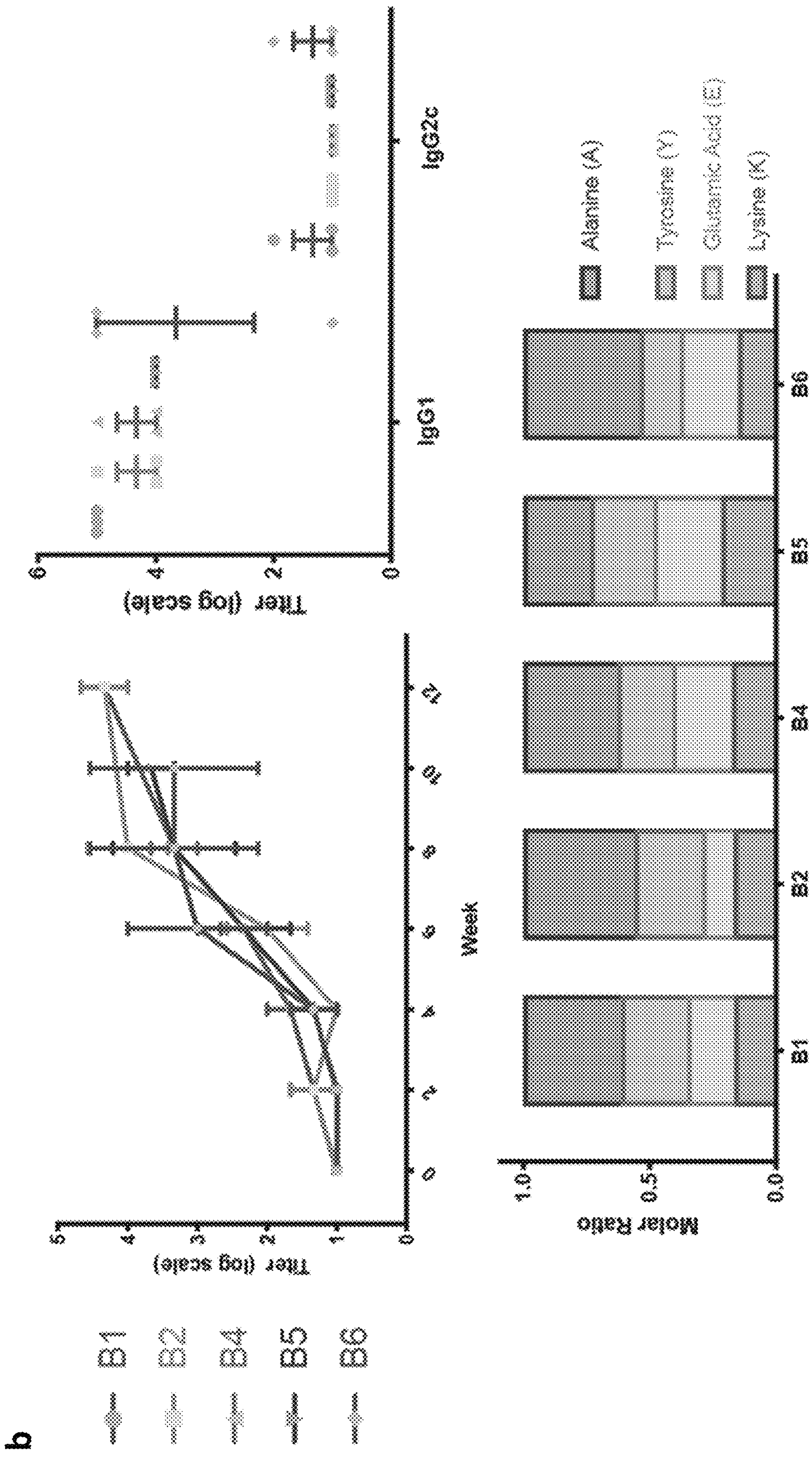
FIGURE 10-continued

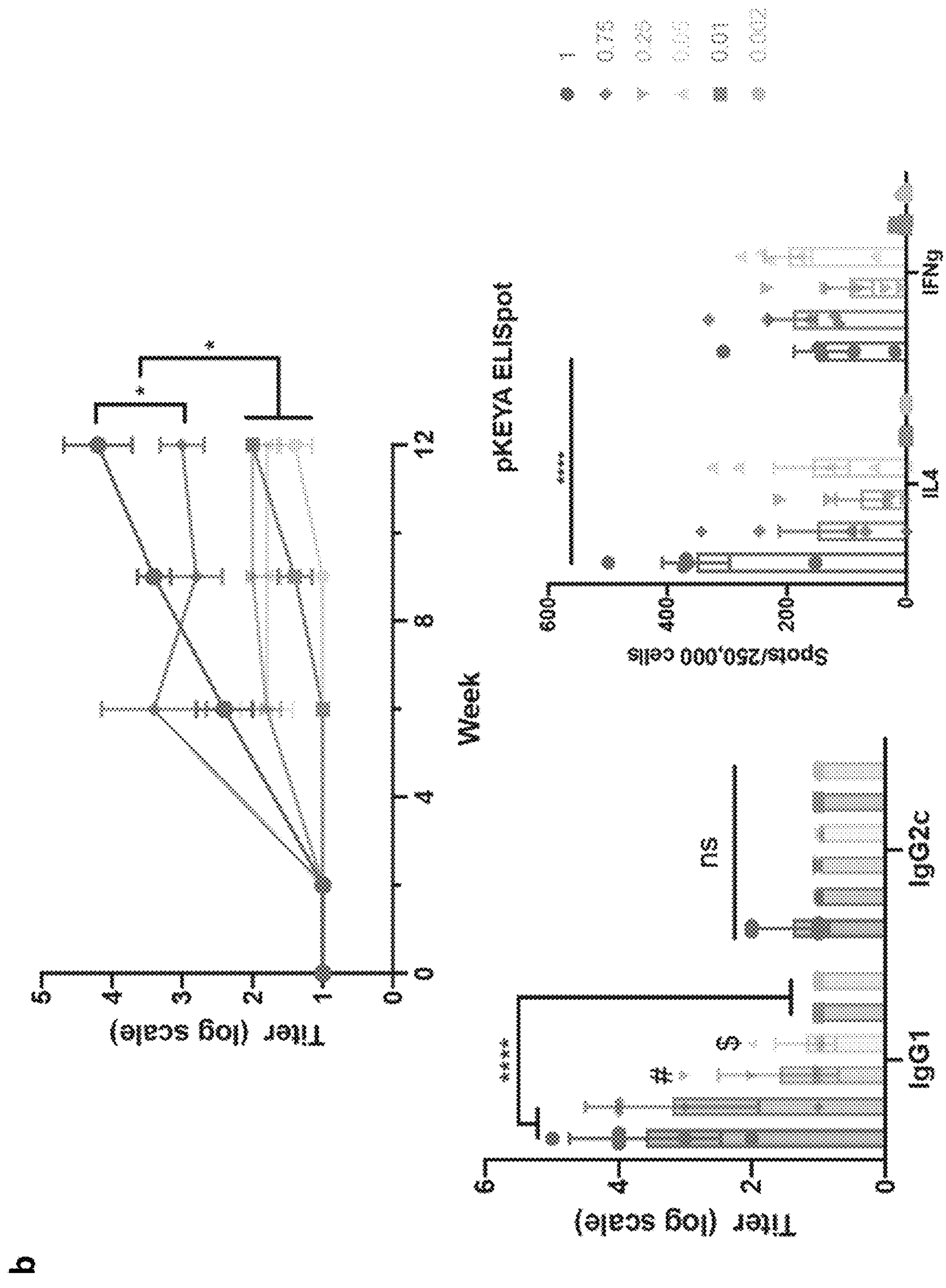
FIGURE 11-continued

Comparisons between $(KEYA)_{20}Q11$ and Glatiramoids

| | $(KEYA)_{20}Q11$ | Glatiramoids |
|---|---|---|
| Method of preparation | Solid phase peptide synthesis | Polymerization of the mixed amino acids, depolymerization and deprotection, and purification |
| Supramolecular assembly | Nanofiber, likely $\beta$-sheet | Possible aggregations |
| Mechanism of action | APC uptake and polarization, downstream T cell bias toward Th2 phenotype which suppresses inflammatory Th1 phenotype | APC uptake and polarization, downstream T cell bias toward Th2 phenotype which suppresses inflammatory Th1 phenotype |
| Number of required boosts | Mouse studies show injections every 2.5 weeks is sufficient to raise and maintain an immune response | FDA approved for daily or twice a week injections |
| Ability to be modified | Easily dry mix with any other epitope-Q11 to co-assemble factors into one nanofiber therapeutic | Difficult. Need to re-formulate from original amino acid mixture. |

FIGURE 13

SUPRAMOLECULAR POLYPEPTIDE COMPOSITIONS AND METHODS OF MAKING AND USING THE SAME

CROSS-REFERENCE TO RELATED APPLICATIONS

This patent application is a national stage filing under 35 U.S.C. § 371 of International Application No. PCT/US2020/031351 filed May 4, 2020, which claims the benefit of priority of U.S. Provisional Patent Application No. 62/841,972, filed May 2, 2019, both of which are incorporated herein by reference in their entirety.

STATEMENT REGARDING FEDERALLY SPONSORED RESEARCH

N/A

SEQUENCE LISTING

A Sequence Listing accompanies this application and is submitted as an ASCII text file named "155554_00622_ST25.txt", which is 25,189 bytes in size and was created on Sep. 27, 2024. The sequence listing is electronically submitted via Patent Center with the application and is incorporated herein by reference in its entirety.

BACKGROUND

Peptide-based therapeutics have received growing interest due to their ability to be highly specific while limiting off-target effects. This interest is especially high in vaccine design, where cellular and humoral peptide epitope-based vaccines are being explored against a variety of infectious diseases, cancers, or therapeutic targets. T cell vaccines targeting infectious diseases such as coronavirus[1], coccidioidomycosis[2], influenza[3], *H. pylori*[4], HIV[5], mononucleosis[6], and several others have achieved protection by activating epitope specific CD4+ and CD8+ T-cell populations. Cytotoxic T lymphocytes have further been the focus of many epitope-based vaccines targeting cancers[7-9], often triggering these responses through antigen presentation on major histocompatibility complex (MHC) I and II. Also, B-cell targeting vaccines being investigated for grass pollen allergy[10], influenza[3], HIV-1[11], mastitis[12], and a variety of cancers[9,13] have seen success through raising epitope specific IgG antibody responses. Most of these epitope-based vaccines, however, rely on epitope prediction software, repetition of sequences, adjuvants, and a mixture of multiple epitopes to create an effective therapeutic. Additionally, many of these diseases, including influenza, HIV, coronavirus, and most cancers, require a combination of cellular and humoral epitope targeting to raise protection, and active immunotherapies where a focused B-cell response is critical usually require both T-cell help and adjuvants. Strong adjuvants, while commonly used in conjunction with peptide therapeutics to combat the low immunogenicity of peptide epitopes, have been known to induce side effects such as swelling and pain at the injection site. Therefore, it is clear that the ability to co-deliver multiple epitopes while simultaneously and safely enhancing immune cell engagement is paramount. In response, work has been conducted to engineer peptide therapies to increase immunogenicity by designing nanomaterial platforms that provide co-delivered T-cell help. Relatively few universal T-cell epitopes have been developed, but some of the most widely used include PADRE[14] or VAC, from the vaccinia virus[15]. These T-cell epitopes have been useful in boosting the B-cell response in a variety of platforms but vary in the strength and breadth of induced immune responses, generally requiring laborious optimization. Moreover, most platforms are limited in the number of B-cell epitopes that can be attached and are therefore unable to maximize the therapeutic efficacy.

Thus, designing a universal T-cell epitope with the ability to target additional effector cell populations and boost responses to co-delivered antigens on a platform that maximizes available epitopes while maintaining a non-inflammatory immune response could greatly augment current peptide-based immunotherapies.

BRIEF SUMMARY OF THE INVENTION

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the discovery by the inventors of a supramolecular (self-assembling) peptide that comprises a plurality of randomized polyamino acids that self-assemble into nanofibers.

As used herein and throughout the specification and figures, the terms used and the naming of the random polypeptide contemplated herein to be used in the supramolecule peptides denoted "$(KEYA)_n$" or "$(KEYA)_x$" is understood to be equivalent to a peptide $X_n$, and refers to a polypeptide with a length of n amino acids (e.g., 5-60 amino acids) and wherein the sequence of amino acids is a random sequence of the amino acids K, E, Y, and A. For example, "$(KEYA)_{20}$"=$X_{20}$, a polypeptide with 20 amino acids, and each of the 20 "X" amino acids are randomly selected from the amino acids K, E, Y, and A. The order of "KEYA" denoted in the naming is for convenience only, and does not infer that the amino acids are arranged in that specific order or that all four amino acids are used in any particular peptide. Thus this designation encompasses any number of random amino acids selected from K, E, Y, and A including sequences that may only contain three of the four amino acids, (e.g., EEKY (SEQ ID NO: 89), EYAK (SEQ ID NO: 90), KKEY (SEQ ID NO: 91), AEKY (SEQ ID NO: 92), etc, as denoted in SEQ ID NO:83).

One aspect of the present disclosure provides a polypeptide molecule comprising, consisting of, or consisting essentially of a self-assembling polypeptide linked to a random polypeptide an optionally a spacer connecting the self-assembling peptide and the random polypeptide. The random polypeptide may be generated from a pool of four amino acids. The self-assembling polypeptide portion of the polypeptide molecule allows for self-assembly of a nanofiber when in contact with a saline or other isotonic solution.

In another aspect, the disclosure provides a polypeptide molecule comprising a self-assembling polypeptide at least four amino acids in length linked to a random polypeptide at least five amino acids in length. In one aspect, the self-assembling polypeptide is at least ten amino acids in length. In a further aspect, the random polypeptide is at least ten amino acids in length. In some aspects, the self-assembling polypeptide is capable of forming nanofibers in solution.

In a further aspect the disclosure provides a pharmaceutical composition comprising any one of the polypeptide molecules described herein and a pharmaceutically acceptable carrier or excipient.

In a further aspect, the disclosure provides a method of making the polypeptide molecule described herein, the method comprising: (a) creating a self-assembling polypeptide through solid phase peptide synthesis; (b) optionally linking a spacer onto the self-assembling polypeptide; (c) reacting at least three amino acids in equal parts to attach one of the at least three amino acids to the self-assembling polypeptide and optional spacer randomly; and (d) repeating step (c) to add up to the desired number of random amino acids to form the polypeptide molecule comprising the random polypeptide linked to the self-assembling polypeptide. A composition comprising the polypeptide molecule made by the method described herein is also contemplated.

In a further aspect, the disclosure provides a method of modulating an immune response in a subject comprising administering a therapeutically effective amount of a polypeptide molecule or the pharmaceutical composition described herein to modulate the immune response in the subject.

In yet another aspect, the disclosure provides a method of treating an inflammatory condition comprising administering a therapeutically effective amount of a polypeptide molecule or the pharmaceutical composition described herein to treat the inflammatory condition in the subject.

In yet another aspect, a kit comprising the polypeptide molecule or the pharmaceutical composition described herein and instructions for use are provided.

Another aspect of the present disclosure provides all that is described and illustrated herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and other features of the disclosure are explained in the following description, taken in connection with the accompanying drawings, herein:

FIG. 10. (a) Listing of MATLAB functions used to calculate molar ratios of K (lysine), E (glutamic acid), Y (tyrosine) and A (alanine) separate from those in the Q11 component. (b) Graphs demonstrate changing the amino acid composition has insignificant effects on antibody production and IgG1 polarization.

FIG. 13. Comparison chart of polypeptide molecules of the present invention and known glatiramoids.

DETAILED DESCRIPTION

Figure 1:
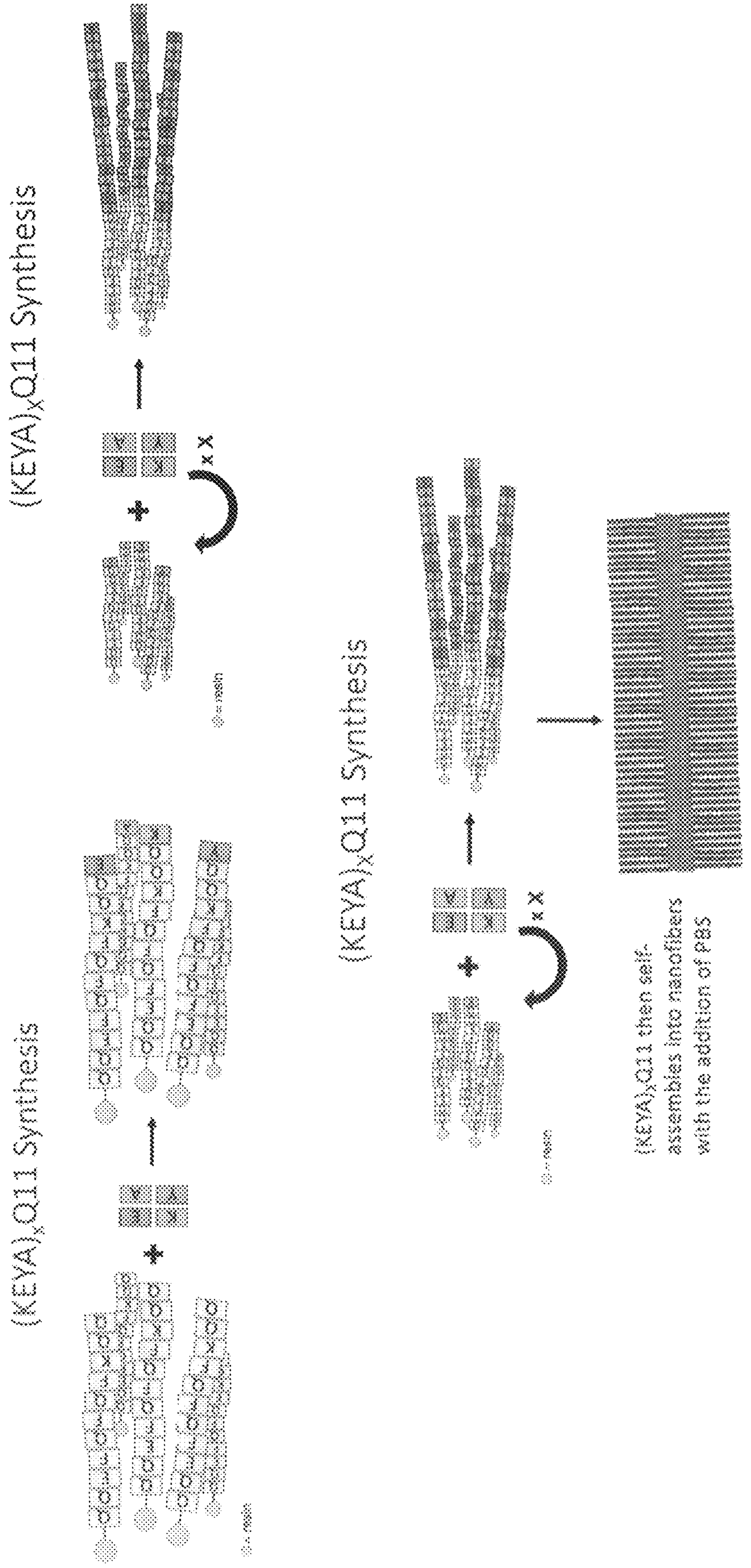
FIG. 1. A cartoon schematic showing the method of making a supramolecular polypeptide complex in accordance with one embodiment of the present disclosure. Amino acid residues randomly selected from lysine (K), glutamate (E), tyrosine (Y), and alanine (A) are added to the N-terminus of the KEYA Q11 peptide (SEQ ID NO:1) using solid phase peptide synthesis to form $(KEYA)_1$Q11 peptides of SEQ ID NO:86 (XQQKFQFQFEQQ, wherein X is randomly selected from K, E, Y, or A). Synthesis continues until 20 additional amino acids have been added, forming $(KEYA)_{20}$Q11 peptides of SEQ ID NO:87 XXXXXXQQKFQFQFEQQ, wherein X is randomly selected from K, E, Y, or A). The $(KEYA)_{20}$Q11 peptides are then self-assembled into nanofibers with the addition of PBS.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Polypeptide Molecules, Compositions and Supramolecular Complexes

The present disclosure is based, in part, on the discovery by the inventors of the ability to link self-assembling polypeptides that form β-sheet nanofibers to a random polypeptide sequence without compromising nanofiber formation. This forms a supramolecular (self-assembling) complex that comprises a plurality of randomized polyamino acids that self-assemble into nanofibers when placed into an isotonic solution. In one example, the self-assembling polypeptide comprises Q11 (SEQ ID NO:1). Other self-assembling peptides can be used as described in more detail below. The self-assembling peptides may form β-sheets, α-helices, or other amphiphiles capable of forming nanofibers. In some embodiments, the present disclosure provides a polypeptide molecule comprising a self-assembling polypeptide at least 10 amino acids in length linked to a random polypeptide at least 10 amino acids in length. These polypeptide molecules can be assembled via isotonic solution into nanofibers, or supramolecular complexes. One aspect of the present disclosure provides a supramolecular complex comprising, consisting of, or consisting essentially of a self-assembling β-sheet nanofiber and a peptide composed of repeated random polymerization of four amino acids. In one embodiment, the nanofiber is a β-sheet and comprises Q11.

The compositions and methods provided herein offer multiple advantages compared to previous soluble forms of random polypeptides, such as glatiramoids, including: 1) nanofiber form that enhances the uptake of the material by antigen-presenting cells and prolongs the persistence of the material; 2) the ability to co-assemble the randomized polypeptides along with other immune epitopes to form integrated materials; 3) the ability to control the charge, hydrophobicity, and other physical properties of the nanofibers by co-assembling other peptides into the nanofibers. These biophysical properties have long been suspected to be relevant to the efficacy of glatiramoids but cannot be easily adjusted in conventional randomized polypeptides.

These properties are important because the randomized polypeptides that constitute glatiramoids have not had these properties, limiting their ability to be tuned or optimized in various disease settings. We have found that the supramolecular complexes based on the randomized polypeptides linked to self-assembling peptides provided herein share properties with previous glatiramoids, including the ability to induce Th2 (non-inflammatory) T-cell responses and raise IgG1 antibodies. This is accomplished with less repetitive dosing compared to previous glatiramoids. The content of the random polypeptide component of the nanofibers can also be adjusted in the nanofibers, leaving considerable room for the integration of other factors, epitopes, or ligands within the nanofibers.

As used herein, the "self-assembling polypeptide" or "self-assembling domain" refers to a polypeptide that is able to spontaneously associate and form stable structures in solution, preferably a stable β-sheet. The self-assembling peptide comprises a C-terminal and an N-terminal end, each of which can be linked to the random peptide.

A β-sheet (or β-pleated sheet) is a secondary structure of a polypeptide. The sheet like structure is created by a series of hydrogen bonds (e.g., at least two or three backbone hydrogen bonds) between residues in different polypeptide chains or between residues in different sections of a folded polypeptide to create a generally twisted, pleated sheet. Typically, adjacent polypeptide chains in β-pleated sheets are antiparallel, in other words they run in opposite directions. However, in some structures adjacent chains may run parallel. In some examples, a number of polypeptides participate in the sheet formation, and the sheet is a rigid structure.

An α-helix is another secondary structure of polypeptides. The α-helical structure is created as a right-handed helical structure where each amino acid residue corresponds to a 100° turn in the helix such that the helix has about 3.6 residues per turn. Each of the backbone N—H groups hydrogen bonds to the backbone C═O group of the amino acid located three or four residues earlier along the amino acid sequence the α-helix is very tightly packed and the amino acid side chains are exposed on the outside of the helix.

Suitably, the self-assembling peptide is about 4 to about 40 amino acids in length, preferably about 10 to about 20 amino acids in length, and may include, for example, at least, at most, or exactly 4, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. In some embodiments, the self-assembling polypeptide has at least some alternating hydrophobic and hydrophilic amino acids. In some embodiments, the self-assembling polypeptides are capable of forming a β-sheet. Hydrophobic amino acids include, for example, Ala, Val, lie, Leu, Met, Phe, Tyr, Trp, Cys, and Pro. Hydrophillic amino acids include, for example, Arg, His, Lys, Asp, Glu, Ser, Thr, Asn, and Gln. In some embodiments, the self-assembling domain is glutamine-rich. A glutamine-rich self-assembling domain may comprise a polypeptide wherein at least about 50%, at least about 55%, at least about 60%, at least about 65%, at least about 70%, at least about 75%, at least about 80%, at least about 85%, or at least about 90% of the amino acids are glutamine. In some embodiments, the self-assembling polypeptides form an α-helix. Amino acids that prefer to adopt helical conformations in a polypeptide include methionine (M), alanine (A), leucine (L), glutamate (E) and lysine (K).

Suitable examples of self-assembling polypeptides, include, for example, those shown in Table 1. In some embodiments, the self-assembling domain includes a modification to the C-terminus, to the N-terminus, or to both the C-terminus and N-terminus. N-terminal modifications may include, for example biotin and acetyl. C-terminal modifications may include, for example, amino and amide. In some embodiments, modifications to the C-terminus and/or to the N-terminus include those shown in TABLE 1. In some embodiments, the self-assembling domain comprises a polypeptide selected from those listed in TABLE 1 but excluding an N-terminal and/or C-terminal modification shown in the table. Self-assembling polypeptides are also detailed in PCT/US2007/020754, PCT/US2017/025596, and are reviewed in Seroski and Hudalia, Self-Assembled Peptide and Protein Nanofibers for Biomedical Applications, Chapter 19 In Biomedical Applications of Functionalized Nanomaterials, (2018) 569-598, all of which are incorporated herein by reference. In addition, the self-assembling domain may be labeled with a detectable label such as a fluorescent molecule, detectable tag or enzyme capable of producing a detectable signal at either the N- or C-terminus. Such detectable labels are known to those of skill in the art and can be attached using routine methods including via a biotin-avidin linkage or amide bond formation.

TABLE 1 self-assembling polypeptides

| Name | Sequence | SEQ ID NO: |
|---|---|---|
| Q11 | QQKFQFQFEQQ | 1 |
| W-Q11 | WQQKFQFQFEQQ | 2 |
| EAK16-I | Ac-(AEAKAEAK)$_2$-$NH_2$ | 3 |
| EAK16-II | Ac-(AEAEAKAK)$_2$-$NH_2$ | 4 |
| EAK16-IV | Ac-AEAEAEAEAKKEAKKE-$NH_2$ | 5 |
| EMK16-II | Ac-(MEMEMKMK)-$NH_2$ | 6 |
| RAD16-1 | Ac-(RADARADA)$_2$-$NH_2$ | 7 |
| RAD16-II | Ac-(RARARDRD)$_2$-$NH_2$ | 8 |
| RAD16-IV | Ac-RARARARARDRDRDRD-$NH_2$ | 9 |
| DAR16-IV | Ac-ADADADADARARARAR-$NH_2$ | 10 |
| KLD16 | Ac-(KLDL)-$NH_2$ | 11 |
| FKFE2 | Ac-(FKFE)$_2$-$NH_2$ | 12 |
| EFK12 | Ac-(FKFE)-$NH_2$ | 13 |
| EFK16 | Ac-(FEFEFKFK)$_2$-$NH_2$ | 14 |
| MAX1 | $H_2N$-VKVKVKVK-$V^D$PPT-KVKVKVKV-$NH_2$ | 15 |
| MAX2 (V16T) | $H_2N$-VKVKVKVK-$V^D$PPT-KVKTKVKV-$NH_2$ | 16 |
| MAX3 (V7T) | $H_2N$-VKVKVKTK-$V^D$PPT-KVKTKVKV-$NH_2$ | 17 |

TABLE 1-continued

| self-assembling polypeptides | | |
|---|---|---|
| Name | Sequence | SEQ ID NO: |
| MAX4 | H$_2$N-KVKVKVKV-K$^{D}$PPS-VKVKVKVK-NH$_2$ | 18 |
| MAX5 (T12S) | H$_2$N-VKVKVKVK-V$^{D}$PPS-KVKVKVKV-NH$_2$ | 19 |
| MAX6 (V16E) | H$_2$N-VKVKVKVK-V$^{D}$PPT-KVKEKVKV-NH$_2$ | 20 |
| MAX7 (V16C) | H$_2$N-VKVKVKVK-V$^{D}$pPT-KVKCKVKV-NH$_2$ | 21 |
| MAX8 (K15E) | H$_2$N-VKVKVKVK-V$^{D}$PPT-KVEVKVKV-NH$_2$ | 22 |
| MAX9 (K2E) | H$_2$N-VEVKVKVK-V$^{D}$PPT-KVKVKVKV-NH$_2$ | 23 |
| MAX10 (K4E) | H$_2$N-VKVEVKVK-V$^{D}$PPT-KVKVKVKV-NH$_2$ | 24 |
| MAX11 (K6E) | H$_2$N-VKVKVEVK-V$^{D}$PPT-KVKVKVKV-NH$_2$ | 25 |
| MAX12 (K8E) | H$_2$N-VKVKVKVE-V$^{D}$PPT-KVKVKVKV-NH$_2$ | 26 |
| MAX13 (K13E) | H$_2$N-VKVKVKVK-V$^{D}$PPT-EVKVKVKV-NH$_2$ | 27 |
| MAX14 (K17E) | H$_2$N-VKVKVKVK-V$^{D}$PPT-KVKVEVKV-NH$_2$ | 28 |
| P11-1 | Ac-QQRQQQQQEQQ-NH$_2$ | 29 |
| P11-2 | Ac-QQRFQWQFEQQ-NH$_2$ | 30 |
| P11-3 | Ac-QQRFQWQFQQQ-NH$_2$ | 31 |
| P11-4 | Ac-QQRFEWEFEQQ-NH$_2$ | 32 |
| P11-5 | Ac-QQ0FOWOFQQQ-NH$_2$ | 33 |
| P11-7 | Ac-SSRFSWSFESS-NH$_2$ | 34 |
| P11-8 | Ac-QQRFOWOFEQQ-NH$_2$ | 35 |
| P11-9 | Ac-SSRFETEFESS-NH$_2$ | 36 |
| P11-12 | Ac-SSRFOWOFESS-NH$_2$ | 37 |
| P11-16 | Ac-NNRFOWOFEQQ-NH$_2$ | 38 |
| P11-18 | Ac-TTRFOWOFETT-NH$_2$ | 39 |
| P11-19 | Ac-QQRQOQOQEQQ-NH$_2$ | 40 |
| 1 | Ac-FEFEFKFKFEFEFKFK-NH$_2$ | 41 |
| 2 | Ac-FEFEAKFKFEFEFKFK-NH$_2$ | 42 |
| 3 | Ac-FEFEFKLKIEFEFKFK-NH$_2$ | 43 |
| 4 | Ac-FEAEVKLKIELEVKFK-NH$_2$ | 44 |
| 5 | Ac-GEAEVKLKIELEVKAK-NH$_2$ | 45 |
| 6 | Ac-GEAEVKIKIEVEAKGK-NH$_2$ | 46 |
| 7 | Ac-IEVEAKGKGEAEVKIK-NH$_2$ | 47 |
| 8 | Ac-IELEVKAKGEAEKLK-NH$_2$ | 48 |
| 9 | Ac-IELEVKAKAEAEVKLK-NH$_2$ | 49 |
| 10 | Ac-IEAEGKGKIEGEAKIK-NH$_2$ | 50 |
| 11 | Ac-KKQLQLQLQLQLQLKK-NH$_2$ | 51 |
| 12 | Ac-EQLQLQLQLQLQLE-NH$_2$ | 52 |
| 13 | Ac-KKSLSLSLSLSLSLKK-NH$_2$ | 53 |
| 14 | Ac-ESLSLSLSLSLSLE-NH$_2$ | 54 |
| 15 | Ac-ECLSLCLSLCLSLE-NH$_2$ | 55 |

TABLE 1-continued

| self-assembling polypeptides | | |
|---|---|---|
| Name | Sequence | SEQ ID NO: |
| 16 | IIIXGK-$NH_2$, wherein X is Q, S, N, G, L, or norvaline | 56 |
| KFE8 | Ac-FKFEFKFE-$NH_2$ | 57 |
| SLAC | KSLSLSLRGSLSLSLKGRGDS | 58 |
| Missing-tooth | KKSLSLSASLSLKK and KKSLSLSASASLSLKK together | 59 and 88 |
| CATCH (+) | Ac-QQKFKFKFKQQ-Am | 60 |
| CATCH (-) | Ac-EQEFEFEFEQE-Am | 61 |
| bQ13 | Ac-QQKFQFQFEQEQQ-Am | 62 |
| Coil29 | QARILEADAEILRAYARILEAHAEILRAQ | 63 |
| PA1 | $C_{16}H_{31}$O-AAAAGGGEIKVAV-COOH | 64 |
| PA | $C_{16}H_{31}$O-CCCCGGGXGGGRGD-COOH, wherein X is phosphoserine | 65 |
| 17 | QAKILEADAEILKAYAKILEAHAEILKAQ | 66 |
| 18 | ADAEILRAYARILEAHAEILRAQ | 67 |

In one embodiment, the present disclosure provides a polypeptide molecule comprising a self-assembling polypeptide at least 10 amino acids in length linked to a random polypeptide at least 10 amino acids in length and compositions comprising the same. In some embodiments, the self-assembling polypeptide comprises a polypeptide having an amino acid sequence of SEQ ID NO:1 (QQKFQFQFEQQ), or a polypeptide with at least 75%, at least 80%, at least 85%, at least 90%, at least 95%, at least 98%, or at least 99% identity thereto. In some embodiments, the self-assembling polypeptide is linked via a linker to the random peptide.

Figure 2:
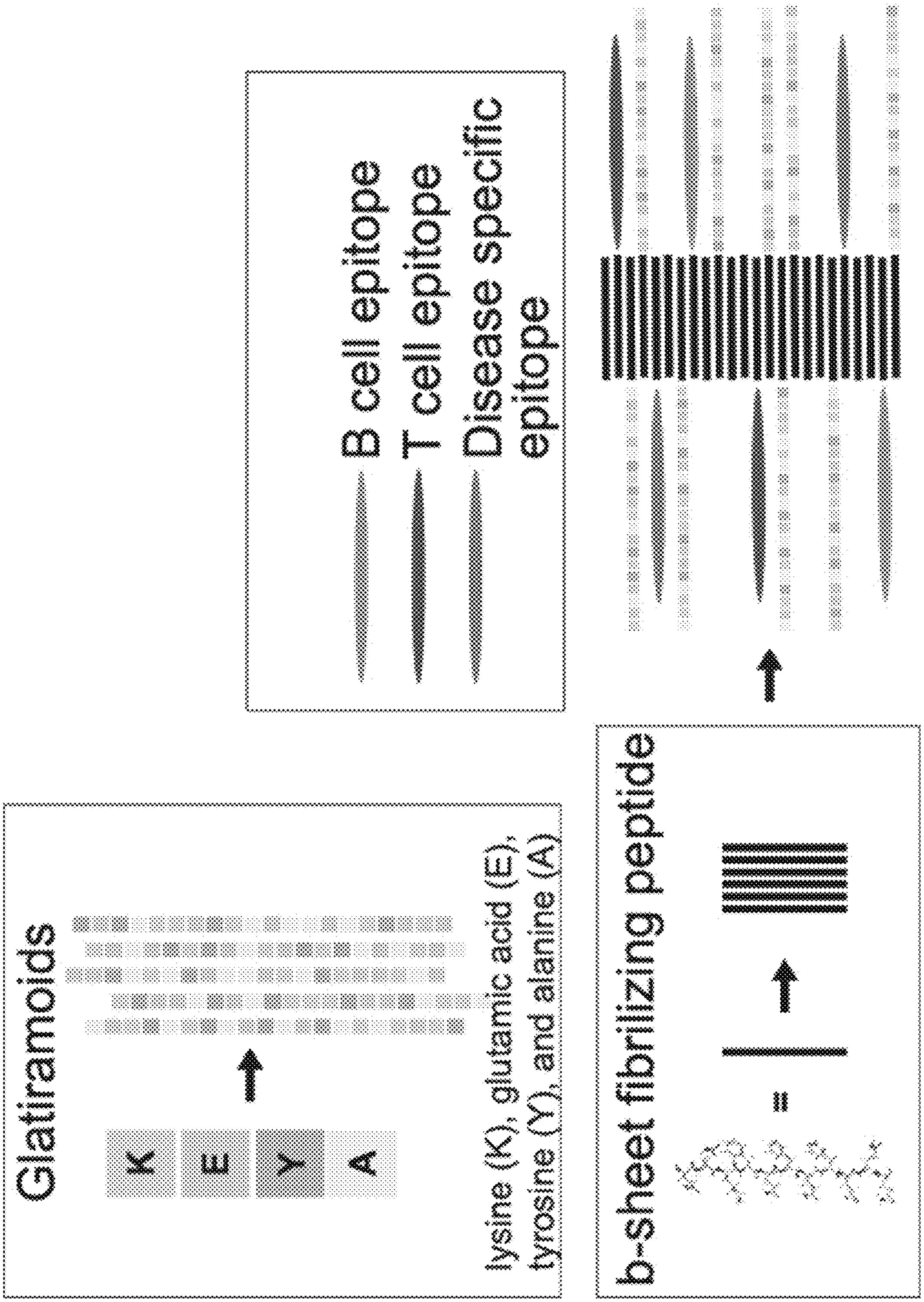
FIG. 2. A cartoon representation of the components of the compositions of the present disclosure, including the ability to be used with T cell epitopes, B cell epitopes and antigens (e.g., disease specific epitopes).
Figure 3:
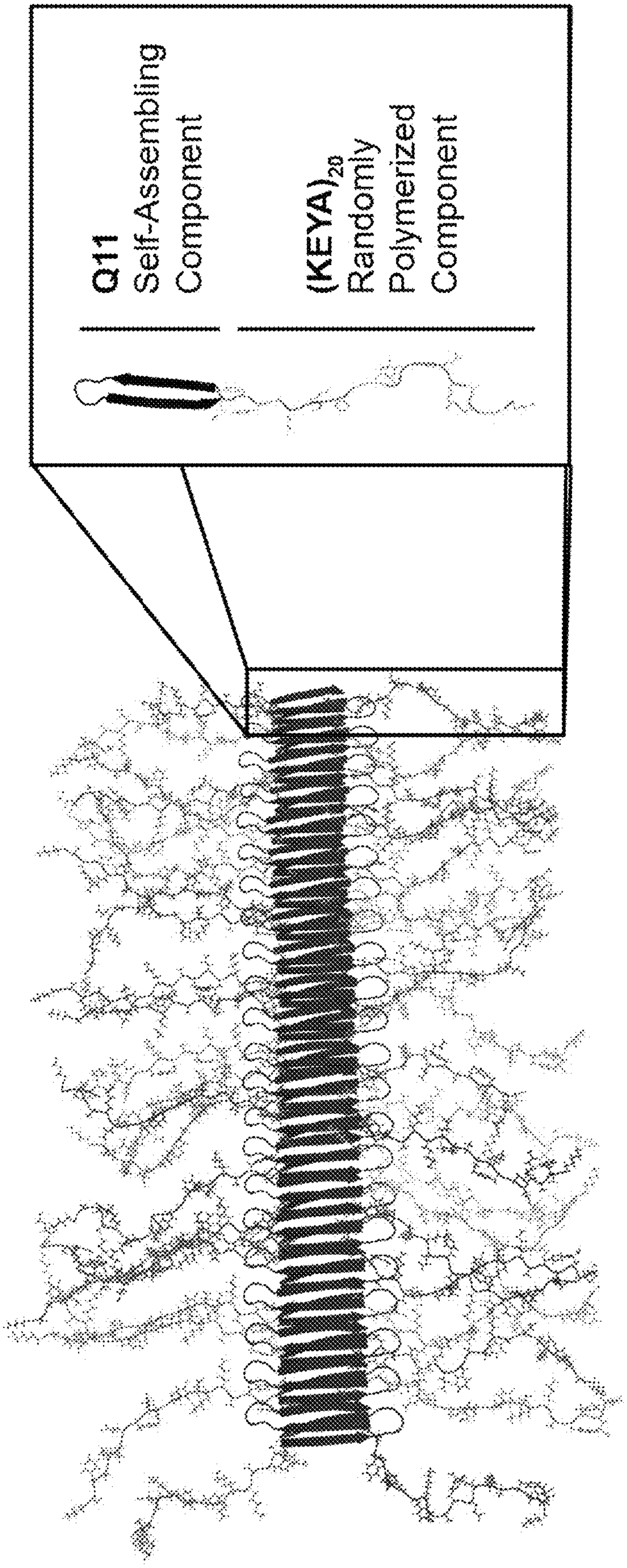
FIG. 3. Reproducible synthesis and characterization of $(KEYA)_{20}$Q11. (a) Hypothesized structure of $(KEYA)_{20}$Q11 self-assembled into a nanofiber. The variety of colors represent the $4^{20}$ possible $(KEYA)_{20}$ sequences. (b) MALDI mass spectrometry indicating a range of molecular weights between the lowest ($A_{20}$Q11: 3416 g/mol) and highest ($Y_{20}$Q11: 5258 g/mol) possible. (c) Amino acid composition of 3 batches from amino acid analysis. (d) ThT assay with β-sheet peak at 480, n=3 experimental replicates per group. (e) Representative atomic force micrograph of $(KEYA)_{20}$Q11 confirms nanofiber formation while peptide-$(KEYA)_{20}$ does not fibrillize. (f) Viability of DC2.4 dendritic cells and RAW264.7 macrophages after incubation with $(KEYA)_{20}$Q11 nanofibers with an alamar blue cell viability assay. *p<0.001, **p<0.0001 by 2way ANOVA with Tukey's post hoc test. Mean+/−s.e.m. shown. n=3 experimental replicates per group.

The self-assembling polypeptide used for the polypeptide molecule is capable of forming nanofibers in solution, e.g., self-assembling into nanofibers when placed in an isotonic solution, as described in more detail below and as depicted in FIGS. 1-3.

The random polypeptide linked to the self-assembling polypeptide (e.g., β-sheet or alpha helix) is preferably at least 5 amino acids in length, preferably at least 10 amino acids in length, and suitably may be any length that is capable of being synthesized (e.g. about 5 amino acids to about 60 amino acids), and include any lengths there between, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 . . . 55, 56, 57, 58, 59, 60, etc. Preferably, the random polypeptide is about 10 to about 30 amino acids in length. The random polypeptide is preferably randomly comprised of amino acids selected from lysine (K), glutamic acid (E), tyrosine (Y) and alanine (A). Suitable examples of peptides are found in SEQ ID NO:82-85 (e.g., $(X)_n$ wherein each X is randomly selected from K, E, Y, A, and n is an integer from 5-60 (SEQ ID NO:82), preferably 10-30, one suitable example is $X_n$, wherein n is 5 (SEQ ID NO:83), $X_n$ wherein n is 10 (SEQ ID NO:84), $X_n$ wherein n is 20 (SEQ ID NO:85). As described in the Examples, the sequence of the random polypeptide is random and the order, and the number of each of the four amino acids within each polypeptide does not alter the functionality of the polypeptide molecule or compositions described herein. Therefore, for example, for a 20 amino acid sequence, there are a diverse population of $4^{20}$ possible peptide sequences that maintain little variation in the overall amino acid composition, self-assemble into nanofibers when lined to the self-assembling peptide, and have no detrimental effect on the viability of classic antigen presenting cells.

In a further embodiment, the random polypeptides include polypeptides with a predetermined sequence as well as mixtures of polypeptides assembled from the four amino acids glutamic acid (E), alanine (A), lysine (K), and tyrosine (Y); from any three of the amino acids Y, E, A and K, i.e. YAK, YEK, YEA or EAK; or from three of the amino acids Y, E, A and K and a fourth amino acid. Examples of glatiramer acetate related polypeptides are disclosed in U.S. Pat. Nos. 6,514,938 A1, 7,299,172 B2, 7,560,100 and 7,655,221 B2 and U.S. Patent Application Publication No. US 2009-0191173 A1, the disclosures of which are hereby incorporated by reference in their entireties. In some embodiments, the four amino acids are selected from the group consisting of K, E, Y, and A.

In some embodiments, the self-assembling polypeptide is linked to the random polypeptide via a spacer. Suitably, the spacer may be any molecule that provides spacing distance between the self-assembling polypeptide and the random polypeptide such that the self-assembling polymer is able to self-assemble and form nanofibers in solution when linked to the random polypeptide. Suitably, in one embodiment, the spacer is a linker polypeptide, suitably a flexible linker polypeptide. The spacer, in some embodiments, is preferably at least three amino acids in length, in some embodiments; the spacer is at least three amino acids in length and less than 25 amino acids in length, preferably less than 10 amino acids in length. Suitable methods of attaching a spacer are known in the art, for example, via amino acid synthesis or via thiol reactive group in the linker. One skilled in the art would be able to develop a suitable spacer. Suitable spacer polypeptides include, but are not limited to, for example, SGSG (SEQ ID NO:68), GGGG (SEQ ID NO:69), GSGS (SEQ ID NO:70), EAAK (SEQ ID NO:71), EAAAK (SEQ ID NO:72), a poly serine (Sn, wherein n is an integer from 1-10), a poly glycine ($G_n$, where n is an integer from 1-10), poly alanine ($A_n$, where n is an integer 1-10), $(SGSG)_n$ (SEQ ID NO:73) wherein n is an integer from 1 to 10), SSSS (SEQ ID NO:74), GGGS (SEQ ID NO:75), GGC, GGS, (GGC) n wherein n is an integer from 1-10, $G_nS_n$, wherein n is an integer from 1-5, GGAAY (SEQ ID NO:76), a randomized Proline-Alanine-Serine (PAS) sequence, and combinations thereof. The peptide linker maybe cleavable by a protease. In some embodiments, the peptide linker comprises a polypeptide having an amino acid sequence of SGSG (SEQ ID NO: 68). In some embodiments, the conjugate includes more than one spacer. In other embodiments, the spacer may be a polymer such as polyethylene glycol (PEG).

In some embodiments of the polypeptide molecule and composition comprising the same, the random polypeptide is N-terminal to the self-assembling polypeptide. In other embodiments of the polypeptide molecule or composition comprising the same, the random polypeptide is C-terminal to the self-assembling polypeptide.

In one embodiment, the polypeptide molecule comprises $(X)_n$-spacer-self-assembling polypeptide wherein n is an integer from 5-60, preferably 10-30, e.g., 20. In one embodiment, the self-assembling peptide is a β-sheet. For example, the polypeptide molecule comprises the formula $(X)_n$-spacer-Q11, wherein n is an integer from 5-60, preferably 10-30, most preferably 10-20 and optionally the spacer is a two to ten amino acid linker polypeptide. In another embodiment, the composition comprises the formula $(X)_{20}$Q11, wherein each X is randomly selected for K, E, Y, or A (e.g., $(KEYA)_{20}$Q11)

In some embodiments, the polypeptide molecule or composition comprising the self-assembling polypeptide linked to the random polypeptide may be lyophilized (e.g., dried) and stored before use. Thus, the lyophilized polypeptide molecule or composition can be hydrated by the addition of a solution allowing for the self-assembling of the secondary structure and the formation of nanofibers in solution. Preferably, the solution is any solution containing salt, for example, an isotonic solution, such as phosphate buffered saline or other like salt solutions, culture medium, body fluids such as blood, serum, plasma, interstitial fluid, or combinations thereof. The formation in solution of the self-assembling polypeptide into nanofibers linking the individual polypeptide molecules described herein can form a supramolecular nanofiber complex. This supramolecular nanofiber complex comprises a plurality of polypeptide molecule (i.e. self-assembling polypeptide linked to the random polypeptide). The supramolecular complex may form at about pH 2-12, about pH 2-6, about pH 2-8, about pH 6-8, about pH 6-12, or about pH 8-12. In some embodiments, the supramolecular complex forms at physiological pH. In some embodiments, the supramolecular nanofiber complex forms at about pH 6 to about pH 8.

In some embodiments, the supramolecular complex forms by dissolving the peptide at a pH of 9-10 and neutralizing to pH 6-8 to form the nanofibers. These supramolecular complex or nanofibers and compositions comprising them can be used for the methods described herein for modulating an immune response and treatments. Methods of lyophilizing of the polypeptide molecule or compositions described herein are known in the art.

Figure 11:
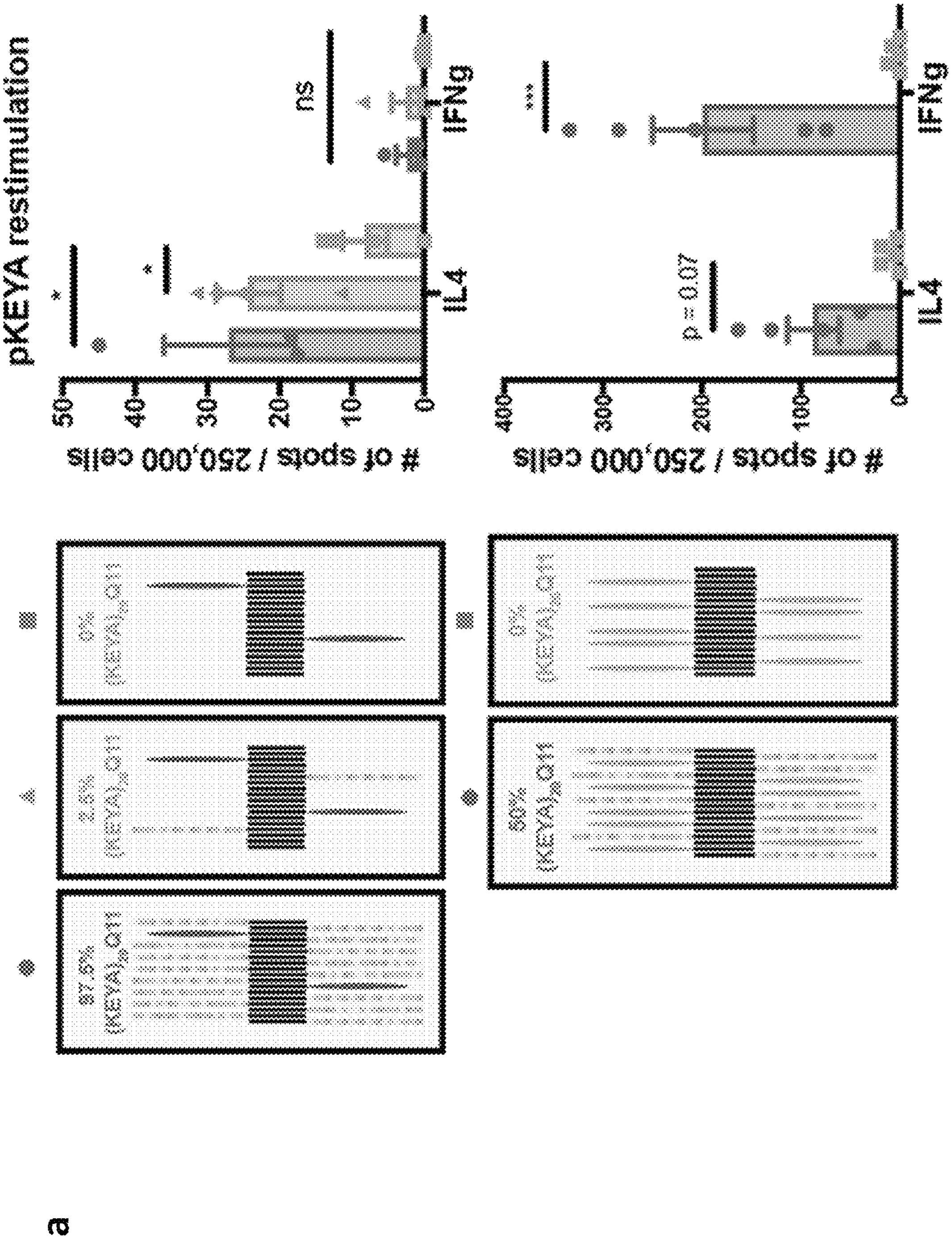
FIG. 11. Supplemental to FIG. 6. (a) T cell stimulation data shows the KEYA specific T-cell response maintains Th2 polarization (when co-assembled with PADRE and NP, respectively). (b) KEYA specific B- and T-cell responses maintain anti-inflammatory populations at high concentrations of KEYA (when co-assembled with TNF B-cell epitope).

In some embodiments, the disclosure provides compositions comprising the polypeptide molecule described herein. The supramolecular complex can be used in compositions comprising a variety of amounts of the supramolecular complex. As demonstrated in the Examples, as little as 1% $(X)_n$-self-assembling polypeptide can be used to increase uptake into antigen presenting cells and percentages as low as 2.5% $(X)_n$-self-assembling polypeptide was able to modulate the immune response and affect T cell responses, where each X is independently K, E, Y or A and n is an integer from 5-60, preferably 5-30. In some aspects, the composition may comprise a mixture of polypeptide molecules having different lengths of the random polypeptides. In other embodiments, the compositions may comprise a mixture of the polypeptide molecule described herein and the self-assembling polypeptide alone (e.g., $(KEYA)_n$ containing self-assembling polypeptide (e.g., Q11)) or the self-assembling polypeptide (e.g., Q11) linked to a peptide epitope, B-cell epitope, or T-cell epitope (e.g., a mixture comprising at least 30% $(KEYA)_n$-self-assembling polypeptide (e.g., Q11), the remainder of the mixture being Q11 or another polypeptide molecule comprising epitope-self-assembling polypeptide, see e.g., FIG. 11 for examples). In some embodiments, the mixture comprises from about 30% $(KEYA)_n$-self-assembling polypeptide (e.g., Q11) to 100% $(KEYA)_n$-self-assembling polypeptide (e.g., Q11). As demonstrated in the Examples, the ratio of $(KEYA)_n$-Q11 to Q11/epitope-Q11 can be altered and adjusted depending on the use without interfering with the ability of the nanofiber to modulate the immune response. Suitably, other polypeptide molecule using different self-assembling β-sheet polypeptides are contemplated to be able to be mixed in similar ways (e.g., 30%-100%) and are contemplated within the invention to produce compositions comprising the same (for example, as shown in FIG. 11). For example, the $(KEYA)_n$-Q11 can be used in combination with a B-cell epitope, a T-cell epitope, or peptide epitope (e.g., antigen epitope or the like) linked to the β-sheet polypeptide (e.g., FIG. 11).

Thus, in some embodiments, the compositions or supramolecular complex may include a plurality of different polypeptide molecules. In some embodiments, the composition comprises a plurality of non-identical polypeptide molecules (e.g., some attached to the random polypeptide, some attached to a peptide epitope, an antigen, a B-cell epitope, a T-cell epitope, or combinations thereof).

Pharmaceutical compositions comprising the polypeptide molecule described herein and mixtures thereof are further contemplated herein. The pharmaceutical composition can further comprise a pharmaceutically acceptable carrier or excipient. In some embodiments, the pharmaceutical composition comprising, consisting of, or consisting essentially of a supramolecular complex as provided herein and a pharmaceutically acceptable carrier and/or excipient. In one embodiment, the pharmaceutical composition comprising, consisting of, or consisting essentially of a supramolecular complex having the formula $(KEYA)_n$Q11 (e.g., $(KEYA)_{20}$Q11 both with and without a spacer) and a pharmaceutically acceptable carrier and/or excipient.

A "pharmaceutically acceptable carrier," "pharmaceutically acceptable excipient" or "diagnostically acceptable excipient" includes but is not limited to, saline, phosphate buffered solutions, amino acid-based buffers, or bicarbonate buffered solutions. Preferably, the pharmaceutically acceptable carrier or excipient is a saline solution or comprises adequate amount of saline for the self-assembly of the polypeptides into β-sheets.

Any pharmaceutically acceptable carrier may be used with the present invention. The term "pharmaceutically acceptable" means approved by a regulatory agency of the Federal or a state government or listed in the U.S. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

In some embodiments, the pharmaceutical composition comprises a pharmaceutically acceptable carrier or excipient is a saline or isotonic solution, and wherein the self-assembling β-sheet polypeptide linked to a random polypeptide form nanofiber in solution. Suitably the pharmaceutically acceptable carrier is a saline solution, for example, phosphate buffer saline and the like.

The pharmaceutical composition can further comprise a peptide epitope or antigen. In some embodiments, the epitope is a T cell epitope or a B cell epitope. In another embodiment, the peptide epitope is an antigen epitope.

In some embodiments, the polypeptide molecules can be combined with molecules comprising a peptide epitope, antigen, B-cell epitope, T-cell epitope, or combinations thereof. The peptide epitope may comprise a polypeptide of 3 to 50 amino acids. The peptide epitope may be linked to the N-terminal end or the C-terminal end of the self-assembling β-sheet polypeptide similar to the methods used to attach the random polypeptide described herein. In some embodiments, the peptide epitope is immunogenic. In some embodiments, the peptide epitope is antigenic. In some embodiments, the peptide epitope is a portion of a protein antigen. The peptide epitope or protein antigen can be any type of biologic molecule or a portion thereof. Full-length protein antigens can also be used in combination with the supramolecular polypeptides molecules described herein. For methods of incorporation of antigens into the supramolecular complexes and nanofibers described herein see e.g. U.S. Patent Publication No. US2014/0273148 and Hudalia et al. Nat. Mater. 2014:829-836, both of which are incorporated herein by reference. Suitable antigens include, but are not limited to, microbial antigens, including, viral antigens, bacterial antigens, fungal antigens, protozoa and other parasitic antigens; tumor antigens; antigens involved in autoimmune disease, allergy and graft rejection, and other miscellaneous antigens.

In other embodiments, the peptide epitope comprises an additional B cell epitope or T cell epitope. In some embodiments, the peptide epitope comprises a B cell epitope and a T cell epitope. In some embodiments, the peptide epitope comprises an autologous target or a portion thereof. In some embodiments, the peptide epitope comprises a cytokine, hormone or immunomodulatory protein (e.g. complement) or a portion thereof. These may include but are not limited to complement factors, TNF-α, IL-1B, IL-17, IL-6, IL-2.

B cell epitopes are solvent-exposed portions of an antigen that bind to secreted and cell bound immunoglobulins (i.e., antibodies). B cells recognize the antigens through antigen receptors, B cell receptors (BCR) which contain the membrane-bound immunoglobulins. Upon activation, B cells differentiate and secrete soluble antibodies which mediate humoral adaptive immunity. Antibodies upon binding their cognate antigens are activated, and carry out a number of functions, including neutralizing toxins and pathogens and labeling them for destruction by other cells. T cell epitopes are epitopes of antigens recognized by T cells via their surface a specific receptor, T cell receptor (TCR), which recognize antigens when displayed on the surface of antigen-presenting cells (APCs) bound to major histocompatibility complex (MHC) molecules. T cell epitopes are presented by class I (MHC I) and II (MHC II) MHC molecules that are recognized by two distinct subsets of T cells, CD8 and CD4 T-cells, respectively, and thus T cell epitopes comprise both CD8 and CD4 T cell epitopes. CD8 T cells become cytotoxic T lymphocytes (CTL) following T CD8 epitope recognition. CD4 T cells become helper (Th) or regulatory (Treg) T cells which recognizing their antigens. Th cells amplify the immune response. In a preferred embodiment herein, the T cell response is a Th2 response, e.g., amplify antibody-mediated immunity.

Suitable B-cell and T-cell epitopes may be to any suitable antigen described herein, and include any B-cell or T-cell epitope known in the art. For example, TNF is a disease specific B cell epitope demonstrated to reduce the amount of soluble and bound TNF.

The terms "epitope" and "antigenic determinant" may be used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen in well known assays to those of skill in the art such as ELISAs. T cells recognize continuous epitopes of about 9-11 amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996) or by cytokine secretion in assays that are well known to those of skill in the art and include ELISpots as used herein.

The term "antigen" refers to a molecule capable of being bound by an antibody or a T cell receptor and encompasses T cell epitopes and B cell epitopes. An antigen is additionally capable of being recognized by the immune system and/or being capable of inducing a humoral immune response and/or cellular immune response leading to the activation of B lymphocytes and/or T lymphocytes. In some embodiments, the antigen contains or is linked to a Th cell epitope. An antigen can have one or more epitopes (B cell epitopes and T cell epitopes). Antigens may include peptides, polypeptides, polynucleotides, carbohydrates, lipids, small molecules, and combinations thereof. Antigens may also be mixtures of several individual antigens. "Antigenicity" refers to the ability of an antigen to specifically bind to a T cell receptor or antibody and includes the reactivity of an antigen toward pre-existing antibodies in a subject. "Immunogenicity" refers to the ability of any antigen to induce an immune response and includes the intrinsic ability of an antigen to generate antibodies in a subject.

Suitable viral antigens are known to one skilled in the art and include, but are not limited to, for example, coronavirus (e.g., SARS-COV-1, SARS-COV-2, including spike protein, NP, among others), human immunodeficiency virus (HIV) antigens (e.g., such as gene products of the gag, pol, and env genes, the Nef protein, reverse transcriptase, among others); hepatitis viral antigens, including hepatitis A, B and C antigens (e.g., S, M, and L proteins of hepatitis B virus, the pre-S antigen of hepatitis B virus, hepatitis C viral RNA, among others); influenza viral antigens (e.g., hemagglutinin and neuraminidase, among others); measles viral antigens (e.g., measles virus fusion protein among others); rubella viral antigens (e.g., proteins E 1 and E2, among others); rotavirus antigens (e.g., VP7s, among others); cytomegalovirus antigens (e.g., envelope glycoprotein B, among others); respiratory syncytial viral antigens (e.g., RSV fusion protein, the M2 protein, among others); herpes simplex viral antigens (e.g., immediate early proteins, glycoprotein D, among others); varicella zoster viral antigens (e.g. gpl, gpl 1, among others); Japanese encephalitis viral antigens (e.g., proteins E, M-E, M-E-NS 1, NS 1, NS 1-NS2A, 80% E, among others); rabies viral antigens (e.g., rabies glycoprotein, rabies nucleoprotein, among others); and any fragment or portions thereof. See Fundamental Virology, Second Edition, e's. Fields, B. N. and Knipe, D. M. (Raven Press, New York, 1991) for additional examples of viral antigens.

Suitable bacterial antigens are known to one skilled in the art and include, but are not limited to, for example, pertussis bacterial antigens (e.g., pertussis toxin, filamentous hemagglutinin, pertactin, FIM2, FIM3, adenylate cyclase, among others); diptheria bacterial antigens (e.g., diptheria toxin or toxoid among others); tetanus bacterial antigens (e.g., tetanus toxin or toxoid among others); streptococcal bacterial antigens (e.g. M proteins among others); gram-negative bacilli bacterial antigens (e.g. lipopolysaccharides among others); *Mycobacterium tuberculosis* bacterial antigens (e.g., mycolic acid, heat shock protein 65 (HSP65), the 30 kDa major secreted protein, antigen 85A among others); *Helicobacter pylori* bacterial antigen components; pneumococcal bacterial antigens (e.g., pneumolysin, pneumococcal capsular polysaccharides among others); hemophilus influenza bacterial antigens (e.g., capsular polysaccharides among others); anthrax bacterial antigens (e.g., anthrax protective antigen among others); rickettsiae bacterial antigens (e.g., romps, among others), or any fragments or portions thereof. Also included with the bacterial antigens described herein are any other bacterial, mycobacterial, mycoplasmal, rickettsial or chlamydial antigens; or any fragments or portion thereof.

Suitable fungal antigens are known or understandable to one skilled in the art and include, but are not limited to, for example, candida fungal antigen components; histoplasma fungal antigens (e.g., heat shock protein 60 (HSP60)), cryptococcal fungal antigens, (e.g., capsular polysaccharides, among others); coccidiodes fungal antigens (e.g. spherule antigens, among others); and tinea fungal antigens (e.g., trichophytin, among others); or any fragments or portions thereof.

Examples of protozoa and other parasitic antigens are known in the art and may include, but are not limited to, for example, *Plasmodium falciparum* antigens (e.g., merozoite surface antigens, sporozoite surface antigens, circumsporozoite antigens, gametocyte/gamete surface antigens, blood-stage antigen pf 1 55/RESA, among others); toxoplasma antigens (e.g., SAG-1, p30, among others); schistosomae antigens (e.g., glutathione-S-transferase, paramyosin among others); *Leishmania major* and other leishmaniae antigens (e.g., gp63, lipophosphoglycan and its associated protein, among others); and *Trypanosoma cruzi* antigens (e.g., the 75-77 kDa antigen, the 56 kDa antigen among others; or a portion thereof.

Examples of tumor antigens are known in the art and depend on the type of tumor to be targeted. Tumor antigens may include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotropin, calcitoni, tyrosinase, papillomavirus antigens, gangliosides or other carbohydrate-containing components of melanoma or other tumor cells; or any fragment or portions thereof. It is contemplated that antigens from any type of tumor cell can be used in the compositions and methods described herein.

Numerous tumor antigens are known in the art, including, but not limited to, for example, (i) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (ii) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triose phosphate isomerase, KIA 0205, CDC-27, and LDLR-FUT, (iii) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1

(associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (iv) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (v) prostate associated antigens such as PAP, PSA, PSMA, PSH-P1, PSM-P1, PSM-P2, associated with e.g., prostate cancer, (vi) immunoglobulin idiotypes (associated with myeloma and B cell lymphomas, for example), and other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), etc. Additional tumor antigens which are known in the art include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

In some embodiments, the peptide epitope is a fragment or portion of an antigen involved in autoimmune diseases, allergy, and graft rejection. For example, an antigen involved in any one or more of the following autoimmune diseases or disorders can be used: diabetes mellitus, arthritis (including rheumatoid arthritis, juvenile rheumatoid arthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves opthalmopathy, sarcoidosis, primary biliary cirrhosis, uveitis posterior, and interstitia lung fibrosis. Examples of antigens involved in autoimmune disease include, but are in no way limited to, for example, glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy may include, for example, pollen antigens such as Japanese cedar pollen antigens, ragweed pollen antigens, rye grass pollen antigens, animal derived antigens such as dust mite antigens and feline antigens, histocompatibility antigens, penicillin, and other therapeutic drugs. Examples of antigens involved in graft rejection may include antigenic components of the graft to be transplanted into the graft recipient such as heart, lung, liver, pancreas, kidney, and neural graft components. An antigen can also be an altered peptide ligand useful in treating an autoimmune disease.

Further examples of miscellaneous antigens which can be can be used in the compositions and methods include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody; or a portion thereof.

The peptide epitope or protein antigen may be linked or coupled to a self-assembling β-sheet polypeptide by any means known in the art, including, for example, click chemistry, Spytag/Spycatcher, oxime ligation, condensation reactions. The linkage may be a covalent bond. In some embodiments, the peptide epitope or protein antigen is attached through a thiol reactive group.

The nanofibers may be produced that may include the same or a plurality of different peptide epitopes or protein antigens.

In some embodiments, the nanofibers formed have a length of 50 nm to 50,000 nm. The nanofibers may have uniform width. In some embodiments, the nanofibers have a width of 5-100 nm.

"Percentage of sequence similarity" or "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (Karlin and Altschul, 1990, *Proc. Natl. Acad. Sci. USA* 87:2267-2268; Altschul et al., 1997, *Nucl. Acids Res.* 25:3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user. The term "substantial identity" of amino acid sequences for purposes of this invention normally means polypeptide sequence identity of at least 40%.

Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

Methods of Making

Another aspect of the present invention provides a method of making the polypeptide molecule described herein. The method comprises: (a) creating a self-assembling polypeptide through solid phase peptide synthesis; (b) optionally linking a spacer onto the self-assembling polypeptide through solid phase peptide synthesis; (c) reacting four amino acids in equal parts to attach one of the four amino acids to the self-assembling β-sheet polypeptide and optional spacer randomly; and (d) repeating step (c) to add up to the desired number of random amino acids to form the polypeptide molecule comprising the random polypeptide linked to the self-assembling β-sheet. In some embodiments, step (b) the spacer is a polypeptide sequence, and the method further comprises synthesizing a flexible linker onto the self-assembling β-sheet polypeptide. Preferably, the self-assembling β-sheet polypeptide comprises at least 10 amino acids, for example, but not limited to, SEQ ID NO:1 (Q11).

Preferably, the at least three amino acids (e.g., four amino acids) used in step (c) are lysine, glutamic acid, tyrosine and alanine, and the four amino acids are added at a desired molar ratio. In one embodiment the molar ratios for each amino acid are the same molar concentration. In another embodiment, lysine was 14-17%, glutamic acid was 10-15%, tyrosine was 24-31% and alanine was 44-45%. These ratios may be varied depending on the use and can readily be determined by those of skill in the art.

The method further comprises repeating step (d) sequentially to add at least 10 amino acids, preferably at least 20 amino acids to the self-assembling β-sheet polypeptide. In some methods, the polypeptide molecule is lyophilized for later use and reconstitution into the nanofibers. Methods of lyophilization are known in the art. The method further comprises severing the polypeptide molecule from the resin used in the solid phase synthesis and deprotecting the side chains of the amino acids. The polypeptides are then lyophilized for storage.

In further embodiments, the method further comprises: (e) adding a saline solution to the composition to allow the self-assembling-sheet polypeptide linked to a random polypeptide to self-assemble into nanofibers. The nanofibers can then be stored for later use. Alternatively, the polypeptide molecules are stored lyophilized, and mixed with a saline solution prior to use.

In some embodiments, polypeptide molecules having different characteristics (e.g., different lengths of the random polypeptide, attached to or combined with different peptide epitopes) are mixed together as dry components and reconstituted in a saline solution to provide a composition having mixed polypeptide molecules, e.g., comprising B-cell or T-cell epitopes interspersed with $(KEYA)_n$-Q11 polypeptide molecules.

The polypeptides described can be chemically synthesized using standard chemical synthesis techniques. In some embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides described herein. Techniques for solid phase synthesis are well known to those of skill in the art and are described, for example, by Barany and Merrifield (1 963) Solid-Phase Peptide Synthesis; pp. 3-284 in The Peptides: Analysis, Synthesis, Biology. Vol. 2: Special Methods in Peptide Synthesis, Part A.; Merrifield et al. (1 963) J. Am. Chem. Soc, 85: 2 149-21 56, and Stewart et al. (1 984) Solid Phase Peptide Synthesis, 2nd ed. Pierce Chem. Co., Rockford, III. In some embodiments, the self-assembling peptide is synthesized by a solid phase peptide synthesis. The peptide and antigens described herein may be produced recombinantly according to techniques known to those of skill in the art.

Compositions comprising the polypeptide molecule made by the method described herein are also contemplated.

In another embodiment, the disclosure provides a method of making a supramolecular randomly polymerized polypeptide complex as provided herein. As shown in FIG. 1, the method comprises, consists of, or consists essentially of (a) creating a Q11 peptide through solid phase peptide synthesis; (b) optionally synthesizing a flexible linker onto the Q11; (c) reacting four amino acids in equal parts to attach one of the four amino acids to the flexible linker-Q11 randomly; (d) repeating step (c) to add up to the desired number of amino acids; and (e) adding PBS to allow the newly created supramolecular glatiramoid to self-assemble into nanofibers.

Another aspect of the present disclosure comprises a method of making a supramolecular randomly polymerized polypeptide complex comprising the formula $(KEYA)_{20}$Q11. The method comprising, consisting of, or consisting essentially of: (a) creating a Q11 peptide through solid phase peptide synthesis; (b) optionally synthesizing a flexible linker onto the Q11; (c) reacting four amino acids in equal parts to attach one of the four amino acids to the flexible linker-Q11 randomly; (d) repeating step (c) to add up to at least 20 amino acids; and (e) adding PBS to allow the newly created polypeptide to self-assemble into nanofibers. In one embodiment, the flexible linker comprises SGSG (SEQ ID NO:68). In another embodiment, the four amino acids are selected from the group consisting of K, E, Y and A.

Methods of Treatment

The present polypeptide molecules and compositions comprising the same described herein are capable of modulating an immune response in a subject in need thereof. The present polypeptide molecules and compositions comprising the same provide additional benefits of being able to be adjusted to modulate an immune response depending on the application, subject and circumstances.

In one embodiment, the invention provides a method of modulating an immune response in a subject comprising administering a therapeutically effective amount of a polypeptide molecule described herein or the pharmaceutical composition described herein to modulate the immune response in the subject. Specifically, the polypeptide molecules and compositions described herein are able to modulate a T-cell response, preferably a Th2 phenotype (e.g., adaptive immunity involving B cells and antibodies). In some embodiments, the modulation of the T cell response is accompanied by an increase in production of IL-4, IL-5 or a combination thereof as compared to a subject not administered the composition. IL-4 and IL5 are anti-inflammatory cytokines and are often co-expressed in Th2 cells. These cytokines are linked to the proliferation and differentiation of T and B cells, thus supporting that the polypeptide molecules (e.g., $(KEYA)_{20}$Q11) can be used as a non-inflammatory immune modulatory or vaccine carrier to increase an adaptive immune response with the ability to stimulate IL4 and IL5 production in vivo.

The immune modulation can include, for example, augmentation of T cell and B cell responses to a specific antigen, increase in Th2 response of T cells, an increase in antibody production against an antigen, and improved immune response to an antigen (for example, as seen by an increase in the antigen-specific antibodies being produced).

Further, the polypeptide molecules and compositions thereof (including $(KEYA)_{20}Q11$) in nanofiber formulations have the ability to enhance the response to co-assembled T cell epitopes, while simultaneously producing a response to $(KEYA)_{20}Q11$. Additionally, $(KEYA)_{20}Q11$ can be used as a T cell epitope for a disease specific TNF B cell epitope while augmenting the response with an additional $(KEYA)_{20}Q11$ specific B cell response and a robust anti-inflammatory response. Thus, in some embodiments, $(KEYA)_{20}Q11$ may be used in a role similar to adjuvants in vaccines to augment the response to specific epitopes with the added benefits of not altering the phenotype of the epitope response and while still inducing a $(KEYA)_{20}Q11$ specific Type 2 immune response. As demonstrated in the examples, the polypeptide molecule nanofibers were shown to be maintained at the site of injection for longer than nanofibers without the random polypeptide (e.g. $(KEYA)_nQ11$). Thus, not to be bound by any theory, but the polypeptide molecules and compositions thereof may be maintained longer at the site of injection and within the subject allowing for a more robust immune response to form.

Accordingly, one aspect of the present disclosure provides a method of modulating T cells in a subject comprising, consisting of, consisting essentially of administering to a subject a therapeutically effective amount of a supramolecular nanofiber containing a randomly polymerized polypeptide component such that the T cells are modulated in the subject. In some embodiments, the T cell modulation comprises promoting Th2 T cell polarization.

In another aspect, the present disclosure provides a method of modulating T cells in a subject comprising, consisting of, consisting essentially of administering to a subject a therapeutically effective amount of a supramolecular nanofiber containing a randomly polymerized polypeptides complex such that the T cells are modulated in the subject. In some embodiments, the T cell modulation comprises promoting Th2 T cell polarization. It should also be noted that any T cell epitope combined with the nanofibers described herein will maintain its nature T cell bias.

The polypeptide molecule and supramolecular nanofiber containing a randomly polymerized polypeptides described herein can be administered to a subject, either alone or in combination with a pharmaceutically acceptable excipient and/or carrier, in an amount sufficient to induce an appropriate immune response (e.g., immunomodulatory response). The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

In another aspect, the disclosure provides a method of treating an inflammatory condition comprising administering a therapeutically effective amount of a polypeptide molecule or the pharmaceutical composition described herein to treat the inflammatory condition in the subject. Not to be bound by any theory, but the polypeptide molecules and combinations thereof promote an anti-inflammatory immune response, and thus administration modulates the immune response to reduce the inflammatory condition or disorder.

Suitable inflammatory conditions that can be treated by the methods described herein include, but are not limited to, for example, a graft rejection, wound healing, inflammatory diseases, infectious diseases, autoimmune diseases, pharmaceutical side effects causing inflammation, and combinations thereof.

As used herein, the term "autoimmune disorder" (also referred to as "autoimmune disease") refers to those conditions that are caused by a subject's immune system attacking the subjects own, normal body tissue. Suitable autoimmune disorders that can be treated by the methods described herein are known in the art and include, for example, diabetes mellitus, arthritis (including rheumatoid arthritis, juvenile rheumatoid arthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, alopecia areata, Crohn's disease, cutaneous lupus erythematosus, scleroderma, autoimmune uveitis, aplastic anemia, pure red cell anemia, idiopathic thrombocytopenia, polychondritis, Wegener's granulomatosis, Graves opthalmopathy, sarcoidosis, primary biliary cirrhosis, uveitis posterior, among others. In preferred embodiments, the autoimmune disease that can be treated by the methods described herein include, but are not limited to, for example, inflammatory bowel disease (IBD), multiple sclerosis, rheumatoid arthritis, Huntington's disease, psoriasis, systemic lupus erythematosus, and type I diabetes, among others.

Methods of eliciting an immune response to a peptide epitope in a subject are also provided. The method may include administering to the subject an effective amount of the polypeptide molecule or compositions described herein including a peptide epitope. In some embodiments, the immune response is an antigen-specific immune response. In some embodiments, the antigen-specific immune response is an adaptive immune response that occurs upon subsequent encounter with an antigenic determinant. In some embodiments, the immune response comprises lgG1 antibody isotypes response. In some embodiments, lgG1 antibody isotypes are significantly more in relation to the other antibody isotypes in the immune response. In some embodiments, the titer of lgG1 is at least 1, 1.5, 2, 2.5, or 3 log 10 units higher than other isotypes.

Method of immunizing a subject against an antigen or pathogen are also provided. The method may include administering to the subject an effective amount of the polypeptide molecule or compositions described herein, as detailed herein in combination with an antigen, an antigenic epitope, or combinations thereof. In some embodiments, the polypeptide molecule or composition described herein is co-administered with an antigen, adjuvant or other immune-modulatory molecule.

Further, the polypeptide molecules, compositions and supramolecular nanofiber containing a randomly polymerized polypeptide complexes as provided herein are also useful in treating anti-inflammatory conditions in a subject. As used herein, the term "anti-inflammatory conditions" refer to those conditions characterized by the present of an inflammatory response in a subject. Examples include, but are not limited to, graft rejection, wound healing, inflammatory diseases, and autoimmune disease. Accordingly, another aspect of the present disclosure provides a method of treating an anti-inflammatory condition in a subject, the method comprising, consisting of, or consisting essentially of administering to the subject a therapeutically effective amount of a supramolecular glatiramoid as provided herein such that the anti-inflammatory condition is treated. In some embodiments, the supramolecular nanofiber containing a randomly polymerized polypeptide comprises the formula $(KEYA)_{20}Q11$.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. For example, the term encompasses reducing or inhibiting one or more symptom of the disease or condition.

The method and mode of administration will be determined depending on the method of use. The term "administration" or "administering," as used herein, refers to providing, contacting, and/or delivery of an agent by any appropriate route to achieve the desired effect. Suitable routes or administration include, but are not limited to, orally, nasally, intradermal, intramuscular, intraperitoneal, intravenous, intranasal, epidural, subcutaneous, topically, as aerosols, suppository, and may be used in combination.

Effective amounts of polypeptide molecule or supramolecular nanofiber containing a randomly polymerized polypeptides can be determined by a physician with consideration of individual differences in age, weight, tumor size, extent of infection or metastasis, and condition of the patient (subject). For example, in an injectable form, the dosage may comprise 1 mg/ml, 2 mg/ml, 3 mg/ml, 4 mg/ml, 5 mg/ml, 6 mg/ml, 7, mg/ml, 8 mg/ml, 9 mg/ml, 10, mg/ml, 15 mg/ml, 20 mg/ml, 25 mg/ml, 30 mg/ml, 35 mg/ml, 40 mg/ml, 45 mg/ml, 50 mg/ml. The optimal dosage and treatment regime for a particular patient can readily be determined by one skilled in the art of medicine by monitoring the patient for signs of disease and adjusting the treatment accordingly.

An effective amount of the polypeptide molecule, composition or supramolecular nanofiber containing a randomly polymerized polypeptides described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

An effective amount for a particular subject/patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are possible examples of cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The polypeptide molecules, compositions or supramolecular nanofiber containing a randomly polymerized polypeptides according to the present disclosure may also be administered with one or more additional therapeutic agents. Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Co-administration need not refer to administration at the same time in an individual, but rather may include administrations that are spaced by hours or even days, weeks, or longer, as long as the administration of multiple therapeutic agents is the result of a single treatment plan. The co-administration may comprise administering the polypeptide molecules, compositions or supramolecular nanofiber containing a randomly polymerized polypeptides of the present disclosure before, after, or at the same time as the additional therapeutic(s). In one treatment schedule, the polypeptide molecules, compositions or supramolecular nanofiber containing a randomly polymerized polypeptides of the present disclosure may be given as an initial dose in a multi-day protocol, with one or more additional therapeutic agents given on later administration days; or the one or more additional therapeutic agents given as an initial dose in a multi-day protocol, with the polypeptide molecules, compositions or supramolecular nanofiber containing a randomly polymerized polypeptides of the present disclosure given on later administration days. On another hand, one or more additional therapeutic agents and the polypeptide molecules, compositions or supramolecular nanofiber containing a randomly polymerized polypeptides of the present disclosure may be administered on alternate days in a multi-day protocol. In still another example, a mixture of one or more additional therapeutic agents and the polypeptide molecules, compositions or supramolecular nanofiber containing a randomly polymerized polypeptides of the present disclosure may be administered to modulate the immune response. This is not meant to be a limiting list of possible administration protocols.

An effective amount of a one or more therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of the one or more therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The present disclosure further provides a kit comprising the polypeptide molecule described herein or pharmaceutical composition described herein and instructions for use. Kits may be used for carrying out the methods as described above. For example, the kit may be used for modulating an immune response in a subject, eliciting an immune response within the subject, or treating one or more diseases or disorders associated with an immune response in a subject.

Yet another aspect of the present disclosure provides all that is disclosed and illustrated herein.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result, and refers to an amount+/−10%.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The following Examples are provided by way of illustration and not by way of limitation.

EXAMPLES

Example 1: Supramolecular Assemblies Containing Randomized Polypeptides for Eliciting Minimally Inflammatory B Cell and T Cell Responses The success of immunotherapies commonly hinges on eliciting a specified and optimized phenotype of the immune response, including the T-effector population.

Previous vaccines and immunotherapies based on supramolecular peptides and proteins have been shown to raise strong B-cell and T-cell responses without adjuvant, but that is dependent on the quality of the selected epitope. Strategies to broadly increase these responses or adjust the character of the immune response raised have been minimally explored outside commonly used adjuvants.

This Example demonstrates the use of self-assembling randomized polypeptides inspired by glatiramoids, a class of randomly polymerized polyamino acids, to raise B cell responses along with non-inflammatory Th2 type T cell responses, in the absence of additional adjuvant. The inventors sought to add glatiramoid-like behavior to peptide self-assemblies currently under investigation towards a range of immunotherapies, hypothesizing that self-assemblies bearing randomized polypeptides would specifically engage non-inflammatory T cell populations compared with unmodified nanofibers and would strengthen responses to co-assembled peptide epitopes. We developed a method for synthesizing self-assembling peptides terminated with libraries of peptides containing Lys, Glu, Tyr, and Ala (termed KEYA) of various lengths with good batch-to-batch reproducibility. These peptides formed regular nanofibers, and KEYA sequences longer than 10 amino acids raised strong antibody responses without adjuvants. The KEYA modifications dramatically enhanced uptake of peptide nanofibers in vitro by various antigen-presenting cells and served as strong B-cell and T-cell epitopes in vivo, enhancing the non-inflammatory phenotypes. KEYA modifications also increased IL-4 production and decreased overall T cell expansion compared to unmodified nanofibers, further indicating maintenance of a Th2 T cell population. The inventors hypothesize that the immunological properties of KEYA modifications were due in part to multiple different T cell epitopes and a longer persistence at the injection site compared to unmodified nanofibers. Addition of the KEYA component augments the immunostimulatory capacity of self-assembling supramolecular peptides and produces non-inflammatory T and B cell populations.

The present example provides a peptide epitope to be incorporated within a supramolecular nanomaterial platform acting as a nano-adjuvant while simultaneously targeting non-inflammatory effector populations. The inventors took inspiration from a developing class of materials termed glatiramoids. Glatiramoids, classified as non-biologic complex drugs, are colloid-forming polypeptides created by random combinations of lysine, glutamic acid, tyrosine, and alanine and range in size from 4-12 kD. The first glatiramoid, glatiramer acetate[16] (trade name Copaxone), was approved for reducing the frequency of relapses in MS in 1995[17] with 3 injections per week. It has been shown to act on antigen-presenting cells (APCs)[18-21], bias non-inflammatory helper T cell (Th2) polarization of CD4+ T cells[19-24], and induce regulatory T cells (Tregs)[25]. Additionally, it is believed that glatiramoids act as universal altered peptide ligands (APL) to create the observed anti-inflammatory and Th2 immune cell populations[20]. APLs are epitopes with 1-2 key amino acid mutations creating an altered binding efficiency with the targeted immune cell[26], and this generally lower binding efficiency favors production of anti-inflammatory populations. A therapeutic containing an immense number of different polypeptide sequences, like glatiramoids, is therefore highly likely to have multiple APLs to autologous targets in both a variety of species and genetic backgrounds. This makes glatiramoid-like antigens potentially useful as a universal T-cell epitope in a co-delivered peptide therapeutic. Glatiramoids continue to be actively investigated and optimized for the treatment of other autoimmune diseases such as Inflammatory bowel disease[27], Huntington's Disease[28], Alzheimer's Disease[29], and macular degeneration[30]; however, no clear strategies exist to modify, optimize, or direct glatiramoids toward specific immune phenotypes tailored to distinct diseases because their complex mechanism of action and heterogeneous composition preclude systematic engineering.

With these motivations, the inventors created an immunomodulatory peptide material inspired by the randomized nature of glatiramoids in a supramolecular system. Supramolecular peptide therapeutics can co-deliver a variety of B- and T-cell epitopes to create specific responses (see, e.g., FIG. 2), and the modular design allows for tuning of relevant physical parameters. We hypothesized that supramolecular nanofibers could be a way to combine the properties of glatiramoids with one or more B cell epitopes and the already self-adjuvanting properties that peptide nanofibers have previously been found to exhibit. Capitalizing on the high aspect ratio of nanofiber assembly, we chose to design our glatiramoid-like epitope on the Q11 platform to maximize simultaneous display of different epitope sequences on one nanofiber. Q11 (QQKFQFQFEQQ (SEQ ID NO:1)) is a self-assembling peptide that acts as a non-inflammatory immunogenic structure for carrying B- and T-cell epitopes[31-34]. Moreover, Q11 is chemically defined and stable in both lyophilized powder and nanofiber form and predictably forms nanofibers even when epitopes are attached at either terminus. Epitopes synthesized on the termini of Q11 can therefore be precisely co-assembled together, allowing for multi-epitope formulations and the modulation of antigen-specific immune responses. By creating a glatiramoid-like peptide library integrated within self-assembling nanofibers, numerous antigens can be presented simultaneously along the nanofibers for maximum cellular uptake. It is expected that this will lead to increased immunogenicity of co-assembled epitopes while also creating an epitope-specific non-inflammatory response to the randomized component.

Here, the inventors successfully synthesize Q11 with a glatiramoid analog, termed $(KEYA)_n$Q11 (e.g., $(KEYA)_{20}$Q11), and demonstrate its capacity to activate immune responses. The supramolecular peptide nanofiber $(KEYA)_{20}$Q11 is composed of randomly polymerized polypeptides from lysine (K), glutamic acid (E), tyrosine (Y), and alanine (A), for a total of 20 amino acid additions, and a self-assembling fibrillizing peptide, Q11. $(KEYA)_{20}$Q11 increases engagement with APCs, creates Th2 T cell and non-inflammatory B cell populations, and amplifies the response to co-assembled epitopes. These results suggest a new strategy for augmenting immune responses to peptide-based therapeutics. Randomly polymerized polypeptides can be included in a variety of nanomaterial platforms to increase the immunogenicity of co-assembled epitopes while stimulating anti-inflammatory effector cell populations. We believe their potential is maximized when used in a peptide nanofiber platform due to the sheer number of available epitopes decorating a single nanofiber strand. Finally, because $(KEYA)_{20}$Q11 raises a sustained and non-inflammatory immune response, this peptide epitope-based therapeutic could be an effective treatment in several applications including inflammatory autoimmune diseases, wound healing, and graft rejection.

Characterization of randomly polymerized nanofibers. We generated a heterogeneous population of peptide sequences via the random and simultaneous incorporation of the selected four amino acids during synthesis. This allowed for the creation of a single batch of diverse peptide sequences rather than several different sequences that would later require physical mixing. Because of this chosen method, it was imperative to verify the reproducible production of an assortment of amino acid sequences. MALDI mass spectrometry was used to quantify a range of possible molecular weights corresponding to a diverse sequence population. Mass spectrometry is classically used to confirm the molecular weight of a peptide by exhibiting a single peak at a specific m/z value, but the variety of amino acid sequences instead creates a broad curve (FIG. 3*b*). The lowest possible molecular weight, 3416 g/mol, corresponds to the sequence (A) 20Q11 and the highest, 5258 g/mol, to $(Y)_{20}$Q11. These values define the molecular weight range possible, as indicated with blue bars (FIG. 3*b*). The curve trends toward the lower range of the molecular weights, potentially indicating an aversion to the bulkier tyrosine side chains during the random amino acid polymerization. This is additionally evident in the total amino acid composition breakdown in three batches (FIG. 3*c*). The total molar amount of each amino acid was determined by amino acid analysis, and after subtraction of Lys and Glu residues contributing to Q11, the percentages of Lys, Glu, Tyr, and Ala were calculated using a MATLAB function (FIG. 10(*a*)).

The inventors characterized the extent of batch-to-batch variability using amino acid analysis, because they believed it crucial to synthesize batches of consistent amino acid composition for reproducibility in further experiments. The amount of alanine was almost identical between batches while the largest variability was between tyrosine in batches 2 and 3 (FIG. 3*c*). All batches had comparable antibody titers and T cell responses even when the ratios between the amino acids were purposefully altered (FIG. 10(*b*)), indicating that batches were immunologically similar to each other. Additionally, it was confirmed that the addition of the $(KEYA)_{20}$ random component to Q11 did not disrupt β-sheet supramolecular organization both by a Thioflavin T (ThT) binding assay (FIG. 3*d*) and by visualizing nanofibers with AFM (FIG. 3*e*). The randomly polymerized peptide $p(KEYA)_{20}$ has no nanofiber formation until appended to Q11, termed $(KEYA)_{20}$Q11, which self-assembles into nanofibers in physiological conditions.

Previous studies have found size- and composition-dependent cytotoxicity for various other nanomaterials,[35] so ruling out such a consideration was an important early step towards utilizing these nanomaterials in vitro or in vivo. $(KEYA)_{20}$Q11 was determined to have no effect on cell viability at all working concentrations in vitro. Briefly, an alamarBlue dye was added to cells stimulated with $(KEYA)_{20}$Q11 or DMSO after which it becomes a fluorescent red color in the reducing environment of a healthy cell but remains blue in unhealthy cells. Stimulation with $(KEYA)_{20}$Q11 had no effect on the health of the dendritic cells or macrophages (FIG. 3*f*) at concentrations between 0.2-200 μM when compared to untreated cells. Conversely, stimulation with DMSO had a dose dependent cytotoxic response in both cell types.

In summation, the characterization of $(KEYA)_{20}$Q11 indicates it can be synthesized to create a diverse population of $4^{20}$ possible peptide sequences that maintain little variation in the overall amino acid composition, self-assemble into β-sheet nanofibers, and have no effect on the viability of classic antigen presenting cells.

Optimization of epitope length and nanofiber composition. Before using $(KEYA)_{20}$Q11 as a co-assembled nano-adjuvant, we first sought to maximize the $(KEYA)_{20}$Q11-specific immune responses. Glatiramoids found in the literature are about 4.7-11 kD[21], too long to accurately synthesize on Q11. Therefore, we first had to determine an effective randomized component length. Various lengths of the randomly polymerized component from 1-20 additions to the Q11 nanofiber were synthesized, and their molecular weight spreads were visualized with MALDI mass spectrometry (FIG. 4*a*). The three distinct peaks from $(KEYA)_1$Q11 correspond to A-Q11, K/E-Q11 (the molecular weights of Lys and Glu are too similar to separate), and Y-Q11, and amino acid analysis indicates it is primarily composed of E-Q11 (FIG. 4*b*). For $(KEYA)_5$Q11, $(KEYA)_{10}$Q11, and $(KEYA)_{20}$Q11, the MALDI shows increasingly broad curves rather than distinct peaks due to the large variety in molecular weight (FIG. 4*a*), and their amino acid composition slowly changes from a high Glu content to a high Ala content with increasing randomly polymerized additions (FIG. 4*b*). Mice were immunized with the four $(KEYA)_n$Q11 lengths and boosted every 2.5 weeks for the duration of the 14-week experiment (FIG. 4*c*). Mice produced high $(KEYA)_n$-specific IgG antibodies for 10-20 additions as well as a transient response against $(KEYA)_5$Q11, but no humoral response to $(KEYA)_1$Q11 was elicited (FIG. 4*c*). We hypothesize this is due to the requirement of an epitope length between 8-16 amino acids[36] to fit into MHCII binding pockets. Previous reports indicate induction of antigen specific antibody responses to 12-19mer epitopes[31,33,34], and no humoral response to unmodified Q11[31]. Additionally, IgG antibody titers were dominated by the IgG1 subclass when compared to IgG2c (FIG. 4*d*). IgG1 and IgG2c antibodies are markers for non-inflammatory Th2 and inflammatory Th1 T cell responses, respectively[37], signifying the production of a strong Th2 response to $(KEYA)_{10}$Q11 and $(KEYA)_{20}$Q11.

To confirm this observation, the inventors examined T cell responses to $(KEYA)_1$Q11, $(KEYA)_5$Q11, $(KEYA)_{10}$Q11, and $(KEYA)_{20}$Q11 to compare to the antibody responses. Draining lymph nodes were harvested at week 14 and the purified lymphocytes were re-stimulated with their immunizing peptide in an ELISpot. Cytokines released from lymphocytes upon peptide re-stimulation are captured on the plate and developed into spots which correlates to the magnitude of the T cell response. Counting the cytokine spots indicates the polarization of the lymphocyte population, with IL4 and IFNγ production correlating to a Type 2 and Type 1 T cell phenotype, respectively. $(KEYA)_{20}$Q11 stimulated significantly higher IL4 production by T cells than $(KEYA)_1$Q11 or $(KEYA)_5$Q11, while all of the groups had low IFNγ production (FIG. 4*e*). The T cell results were consistent with the antibody responses in that $(KEYA)_1$Q11 and $(KEYA)_5$Q11 were ineffective at inducing immune responses while $(KEYA)_{10}$Q11 and $(KEYA)_{20}$Q11 induced strong antibody and T cell responses. Taking this data together, the inventors chose to move forward using $(KEYA)_{20}$Q11 because it could be reproducibly synthesized and stimulated both an IgG1 antibody response and Type 2 biased T cell production.

Highlighting an advantage of the Q11 platform, the inventors easily modulated $(KEYA)_{20}$Q11 concentration in the Q11 system by co-assembling varying amounts of Q11 and $(KEYA)_{20}$Q11. It was important to investigate what molecular concentrations of the randomized $(KEYA)_{20}$ component within the Q11 nanofiber formulation would be successful at engaging with antigen presenting cells as up to this point all experiments were done with 100% (KEYA)×Q11, making co-assembly with other epitopes impossible. Helper T cell activation is contingent on antigen presenting cells internalizing, processing, and presenting antigen on class II major histocompatibility molecules (MHCII) on their surface to T and B cells. The inventors first hypothesized that maximizing the uptake of nanofibers into APCs was necessary for maximal humoral and cellular immunity. Dendritic cells were stimulated with Q11 nanofibers containing 0% $(KEYA)_{20}$Q11 (unmodified Q11), 1% $(KEYA)_{20}$Q11, 10% $(KEYA)_{20}$Q11, or 100% $(KEYA)_{20}$Q11) for 0.5-24 hours (FIG. 5*a*). Concentrations of 10% and 100% $(KEYA)_{20}$Q11, which correspond to 20 and 200 μM $(KEYA)_{20}$Q11 in a 200 μM total formulation respectively, have increased uptake as early as 2 hours and almost all cells had taken up the nanofiber by 24 hours. In macrophages, a similar trend is apparent (FIG. 5*a*), but with extremely rapid uptake of 100% $(KEYA)_{20}$Q11. After only 10 minutes, nanofibers containing 100% $(KEYA)_{20}$Q11 are uptaken into almost 100% of macrophages indicating prompt innate immune cell engagement possibly due to a thresholding or clustering of the $(KEYA)_{20}$Q11 epitope.

Nanofiber presence inside the cells was visually confirmed with confocal microscopy on dendritic cells (FIG. 5*b*). Representative images show Q11 minimally internalized after 24 hours (FIG. 5*b*, closed arrow) while $(KEYA)_{20}$Q11 is abundantly present both inside (FIG. 5*b*, closed arrow) and decorating the surface of cells (FIG. 5*b*, open arrow). Moreover, mice administered fluorescently tagged $(KEYA)_{20}$Q11 or Q11 i.p. for 2 hours experience uptake of the nanofibers into almost 100% of the local macrophages (FIG. 5*c*). Dendritic cells also took up $(KEYA)_{20}$Q11 nanofibers into about 60% of their population while Q11 was uptaken in about 25% of the population, mirroring the in vitro studies. Clearly, $(KEYA)_{20}$Q11 improved both the speed and extent of nanofiber uptake into antigen-presenting cells.

Expanding upon our hypothesis, mice were immunized with Q11 nanofibers containing 1-50% $(KEYA)_{20}$Q11 and boosted every 2.5 weeks to determine how the APC uptake corresponded to the humoral and cellular responses. The percentages shown in the legend (FIG. 5*d*) represent the molar concentration of $(KEYA)_{20}$Q11 in the total formulation. For example, 10% is 0.2 mM $(KEYA)_{20}$Q11 and 1.8 mM Q11 in a total 2 mM formulation. Mice exhibited a threshold for $(KEYA)_{20}$-specific IgG antibodies: 33% $(KEYA)_{20}$Q11 or higher was necessary to stimulate a humoral response (FIG. 5*d*). This suggests $(KEYA)_{20}$Q11 is capable of acting as a B cell epitope at high but not low concentrations, consistent with APC uptake and again hinting at the important role of epitope clustering on the nanofibers to engage B cells. Closely examining the IgG subclasses from week 16 serum reveals strong IgG1 biasing from the mice that produced high total IgG titers (FIG. 5*e*), consistent with Type 2 immune responses. Lymphocytes harvested from the spleen at week 16 were processed and re-stimulated ex vivo with $p(KEYA)_{20}$ in an ELISpot. All groups produced high numbers of IL4 spots, but the number of IFNγ spots was significantly lower in the 50%, 33%, and 1% $(KEYA)_{20}$Q11 groups (FIG. 5*f*), suggesting that $(KEYA)_{20}$Q11 is a successful Type 2 T cell epitope at all concentrations. With this information, the inventors can titrate the amount of $(KEYA)_{20}$Q11 in the nanofiber formulations to include or exclude an anti-inflammatory humoral response while maintaining a strong Type 2 cellular response at all concentrations. It is important to note that the ELISpot assay does not have an inherent IL4 biasing as an IFNγ bias can be evoked by adding CpG to the $(KEYA)_{20}$Q11 formulation (FIG. 11(*a*)).

The inventors experimentally uncovered two important thresholding responses with these nanomaterials: a required epitope length and a required epitope concentration within nanofibers, both important for subsequent implementation. $(KEYA)_{20}$Q11 is successful at enhancing uptake into antigen presenting cells which is critical for downstream adaptive immune engagement, as evidenced in s.c. mouse immunizations that can produce strong B and T cell responses sustained over the course of 3 months and preferentially stimulate production of a Type 2 immune response.

Enhancement of co-assembled T and B cell epitopes. Having characterized $(KEYA)_{20}$Q11 and the subsequent humoral and cellular responses, the inventors tested the hypothesis that co-assembling $(KEYA)_{20}$Q11 with other epitopes may enhance the response to the co-assembled epitope. Previous work has established a method for ensuring co-assembly of multiple epitopes onto a single nanofiber[38]. Highlighting an advantage of the Q11 system, we were able to systematically add and titrate co-assembled $(KEYA)_{20}$Q11 with a variety of T and B cell epitopes to investigate the resulting magnitude of immune responses. Due to the ability of $(KEYA)_{20}$Q11 to stimulate T cell responses even at low concentrations, we hypothesized $(KEYA)_{20}$Q11 would have the greatest effect on other T cell epitopes and first combined $(KEYA)_{20}$Q11 with a strong and weak T cell epitope. Mice were immunized and boosted once with co-assembled $(KEYA)_{20}$Q11 and a synthetic T cell epitope termed PADREQ11 (PADRE: aKXVAAWTLKAa, where X=cyclohexylalanine; a=D-Alanine; SEQ ID NO:77), previously used to raise strong T cell responses[34]. All groups included 2.5% PADREQ11, previously determined to be the most effective concentration[34], and either 97.5%, 2.5%, or 0% $(KEYA)_{20}$Q11 calculated as noted above (FIG. 6*a*). As high concentrations of $(KEYA)_{20}$Q11 include an antibody component and low concentrations only stimulate T cell responses, we simultaneously explored the effectiveness of $(KEYA)_{20}$Q11 as a nano-adjuvant and the importance of B cell help by including formulations with 97.5% $(KEYA)_{20}$Q11 and 2.5% $(KEYA)_{20}$Q11. Lymphocyte populations were purified from spleens harvested at 3.5 weeks and all groups were re-stimulated with both pPADRE (FIG. 6*a*) and $p(KEYA)_{20}$ (supplement) in an ELISpot assay. Upon re-stimulation with pPADRE, the immunizations containing $(KEYA)_{20}$Q11 exhibit statistically higher production of IL4 than the immunization without $(KEYA)_{20}$Q11 (FIG. 6*a*). This implies the addition of $(KEYA)_{20}$Q11 can enhance the response to PADREQ11 when co-assembled. Upon re-stimulation with $p(KEYA)_{20}$, we observed that mice immunized with $(KEYA)_{20}$Q11 maintained their Type 2 T cell bias with statistically higher production of IL4 than IFNγ FIG. 11(*b*)).

$(KEYA)_{20}$Q11 was next combined with a weaker T cell epitope specific for inducing CD4+ T cell responses against a novel flu epitope, here termed NP-Q11 (unpublished, Lucas Shores; NH2-QVYSLIRPNENPAHK-Am; SEQ ID NO:78; NP-Q11: NH2-QVYSLIRPNENPAHK SGSG QQKFQFQFEQQ-Am; SEQ ID NO:79).

Unpublished work has shown NP-Q11 stimulates IFNγ biased T cell responses and provides help for a flu B cell epitope to raise low antibody titers, optimized at 50% NP-Q11. However, unpublished studies thus far have indicated NP-Q11 does not raise strong enough responses to be protective against an influenza challenge, highlighting the need to enhance the response to the flu epitope. Mice were immunized and boosted once with nanofiber formulations containing 50% NP-Q11 and either 50% $(KEYA)_{20}$Q11 or 0% $(KEYA)_{20}$Q11 (FIG. 6*b*). Again, spleens were harvested at week 3.5 and purified lymphocyte populations were used for an ELISpot. Lymphocytes were re-stimulated with pNP (FIG. 6*b*) and $p(KEYA)_{20}$ (FIG. 11(*c*)). Strikingly, the addition of $(KEYA)_{20}$Q11 significantly enhanced the T cell response to pNP without altering the balance between IL4 and IFNγ production (FIG. 6*b*). Mice immunized with the formulation containing $(KEYA)_{20}$Q11 additionally produced a strong response to re-stimulation with $p(KEYA)_{20}$ T cells (FIG. 11(*c*)). Overall these findings present a strong argument for the use of $(KEYA)_{20}$Q11 as a nano-adjuvant to enhance the capabilities of T cell epitopes without altering their native phenotype production.

Figure 5:
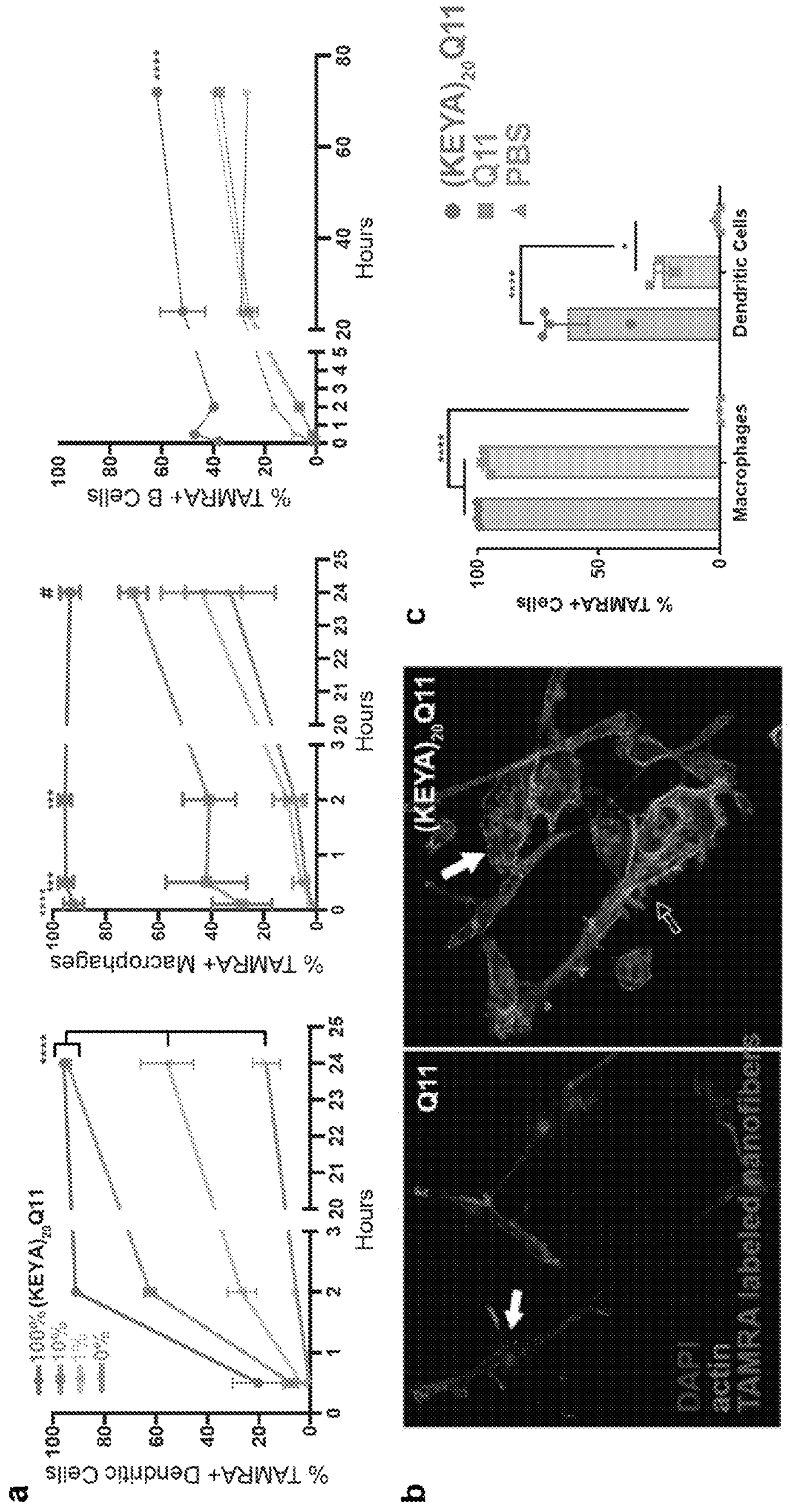

An important function of an effective T cell epitope is to provide help stimulating B cells to produce antibodies. In peptide nanofibers, B cell epitopes require co-assembled T cell epitopes to break tolerance[39]. The inventors hypothesized $(KEYA)_{20}$Q11 could act as an universal T cell epitope to any co-assembled B cell epitope to stimulate antibody production against the B cell epitope. To evaluate the ability of $(KEYA)_{20}$Q11 in this scenario, the inventors titrated the amount of $(KEYA)_{20}$Q11 in a co-assembled fiber with 50% TNF-Q11 (FIG. 6*c*). TNF-Q11 is a peptide epitope for the soluble version of the TNF protein ($TNF_{4-23}$: (SSQNSSDKPVAHVVANHQVE); SEQ ID NO:80 and TNF-Q11: (SSQNSSDKPVAHVVANHQVE-SGSG-QQKFQFQFEQQ); SEQ ID NO:81) and shown to effectively reduce inflammation when a strong B cell response is raised[34]. Mice were immunized and boosted thrice with a final boost done 6 days before sacrifice (FIG. 6*c*). Formulations including 37.5% or 50% $(KEYA)_{20}$Q11 raise pTNF-specific antibodies by week 5 that remain stable for the duration of the 3-month experiment (FIG. 6*d*). Antibodies were likewise raised against the $p(KEYA)_{20}$ epitope from the highest two concentrations of $(KEYA)_{20}$Q11 (FIG. 11(*d*)). The anti-TNF antibody IgG subclasses indicate a polyclonal population production of both IgG1 and IgG2c from the groups with high total IgG titers (FIG. 6*e*) while the antibody IgG subclasses against p$(KEYA)_{20}$ remain IgG1 polarized (FIG. 11(*d*)). Surprisingly, the low concentrations of $(KEYA)_{20}$Q11 no longer raised immune responses, inconsistent with earlier findings (FIG. 5). We believe this could be due to interference with the B cell epitope, decreasing engagement with T cells by relegating the $(KEYA)_{20}$Q11 epitope as subdominant.]

In summation, including $(KEYA)_{20}$Q11 in nanofiber formulations has the ability to enhance the response to co-assembled T cell epitopes, while simultaneously producing a response to $(KEYA)_{20}$Q11. Additionally, $(KEYA)_{20}$Q11 can be used as a T cell epitope for a disease specific TNF B cell epitope while augmenting the response with an additional $(KEYA)_{20}$Q11 specific B cell response and a robust anti-inflammatory response. These findings indicate potential for $(KEYA)_{20}$Q11 to be used similarly to adjuvants to augment the response to specific epitopes with the added benefits of not altering the phenotype of the epitope response and while still inducing a $(KEYA)_{20}$Q11 specific Type 2 immune response.

Figure 4:
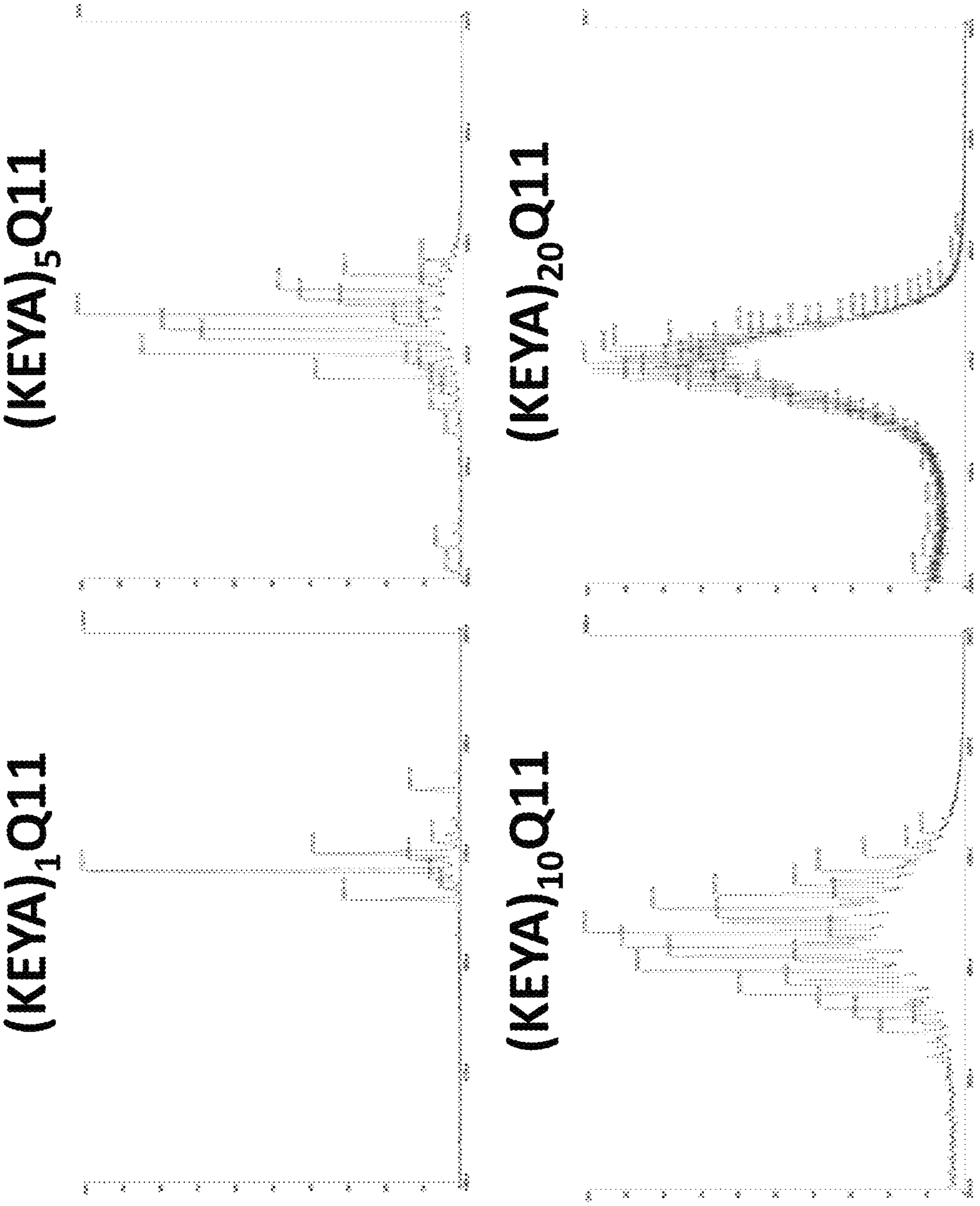
FIG. 4. A 10-20 mer $(KEYA)_x$ epitope length is required for immune engagement. (a) MALDI mass spectrometry graphs for four $(KEYA)_x$ lengths with their amino acid compositions in each box to the right. $(KEYA)_1$Q11 is represented in yellow (far left) for the following graphs, $(KEYA)_5$Q11 in blue, $(KEYA)_{10}$Q11 in green, and $(KEYA)_{20}$Q11 in red (far right). (b) A graph showing the percent of each of the amino acids incorporated into the indicated KEYA peptides. (c) Cartoon indicating the boosting schedule and graph of the anti-immunizing peptide IgG antibody titers. (d) Graph showing the anti-immunizing peptide IgG1 and IgG2c isotype titers for week 14. (e) ELISpot on draining lymph nodes collected at week 14 and restimulated with the immunizing peptide. *p<0.05, p<0.01, *p<0.001, **p<0.0001 by 2way ANOVA with Tukey's post hoc test. Mean+/−s.e.m. shown. n=5 experimental replicates per group FIG. 5**. Titration of $(KEYA)_{20}$ component modulates the strength of engagement with APCs and humoral immunity while maintaining a Type 2 T cell phenotype. Uptake of TAMRA labeled $(KEYA)_{20}$Q11 in (a) DC2.4 dendritic cells, RAW264.7 macrophages, and B-LCL human B cells stimulated for 0.1, 0.5, 2, 24, and 72 (B cells only) hours measured by flow cytometry. 100% refers to the molar percent of $(KEYA)_{20}$ incorporated into a 2 mM Q11 nanofiber. 10% indicates 10% $(KEYA)_{20}$Q11 and 90% Q11, while 0% indicates the entire nanofiber contains only Q11. All groups included 2.5% fluorescent TAMRA-Q11. (b) Representative confocal images of fluorescent Q11 and $(KEYA)_{20}$Q11 stimulated DC2.4 cells. Nanofibers seen in red, cell nuclei in blue, and cell borders in green. Closed arrows show internalization of nanofibers, open arrow shows surface presentation of nanofibers. (c) Populations of mouse APCs containing nanofibers collected 12 hours after i.p. injection. (d) Cartoon indicating the boosting schedule and graph of the anti-p$(KEYA)_{20}$ IgG antibody titers. 50% $(KEYA)_{20}$ is represented darkest red, 33% $(KEYA)_{20}$ in the second darkest, 10% $(KEYA)_{20}$ in the second lightest, and 1% $(KEYA)_{20}$ in the lightest color. Week 16 IgG1 and IgG2c isotypes are shown in (e), $(KEYA)_{20}$ only produces an IgG1 response when at 33% and 50%. (f) ELISpot results show restimulated T cells collected from draining lymph nodes produce a strong IL4 response. *p<0.05, p<0.01, *p<0.001, ****p<0.0001 by 2way ANOVA with (a) Dunnett's multiple comparison test (#=100% significantly different from 2% and 0%) or (e-f) Tukey's post hoc test. Mean+/−s.e.m. shown. n=3-5 experimental replicates per group.
Figure 6:
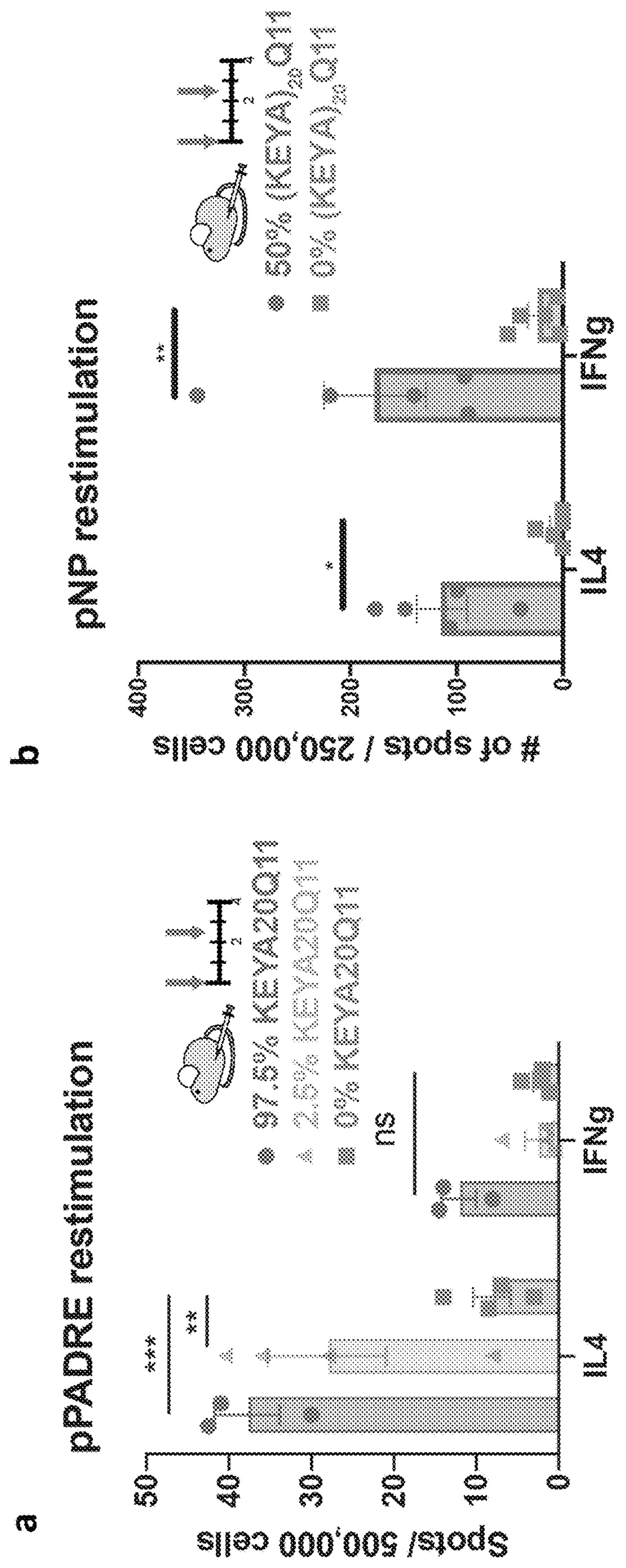
FIG. 6. $(KEYA)_{20}$Q11 can enhance the T cell stimulatory capabilities of other T and B cell epitopes. (a) ELISpot from mice immunized and boosted with nanofiber formulations containing 2.5% PADREQ11 and either 97.5% (dark red), 2.5% (light red), or 0% (gray) $(KEYA)_{20}$Q11 co-assembled with Q11 into a 2 mM nanofiber. The ELISpot shows the spot count from cells restimulated with peptide-PADRE. (b) ELISpot from mice immunized and boosted with nanofiber formulations containing 50% NPQ11 and either 50% (red), or 0% (gray) $(KEYA)_{20}$Q11 co-assembled with Q11 into a 2 mM nanofiber. The ELISpot shows the spot count from cells restimulated with peptide-NP. (c) Cartoon of immunization schedule for figures (d) and (e). All groups contained 50% TNFQ11 (d) anti-TNF IgG antibody titers for groups described in (c). (e) anti-TNF IgG1 and IgG2c antibodies. *p<0.05, p<0.01, *p<0.001 by 2way ANOVA with Sidak's post hoc test. Mean+/−s.e.m. shown. n=3-5 experimental replicates per group.
Figure 7:
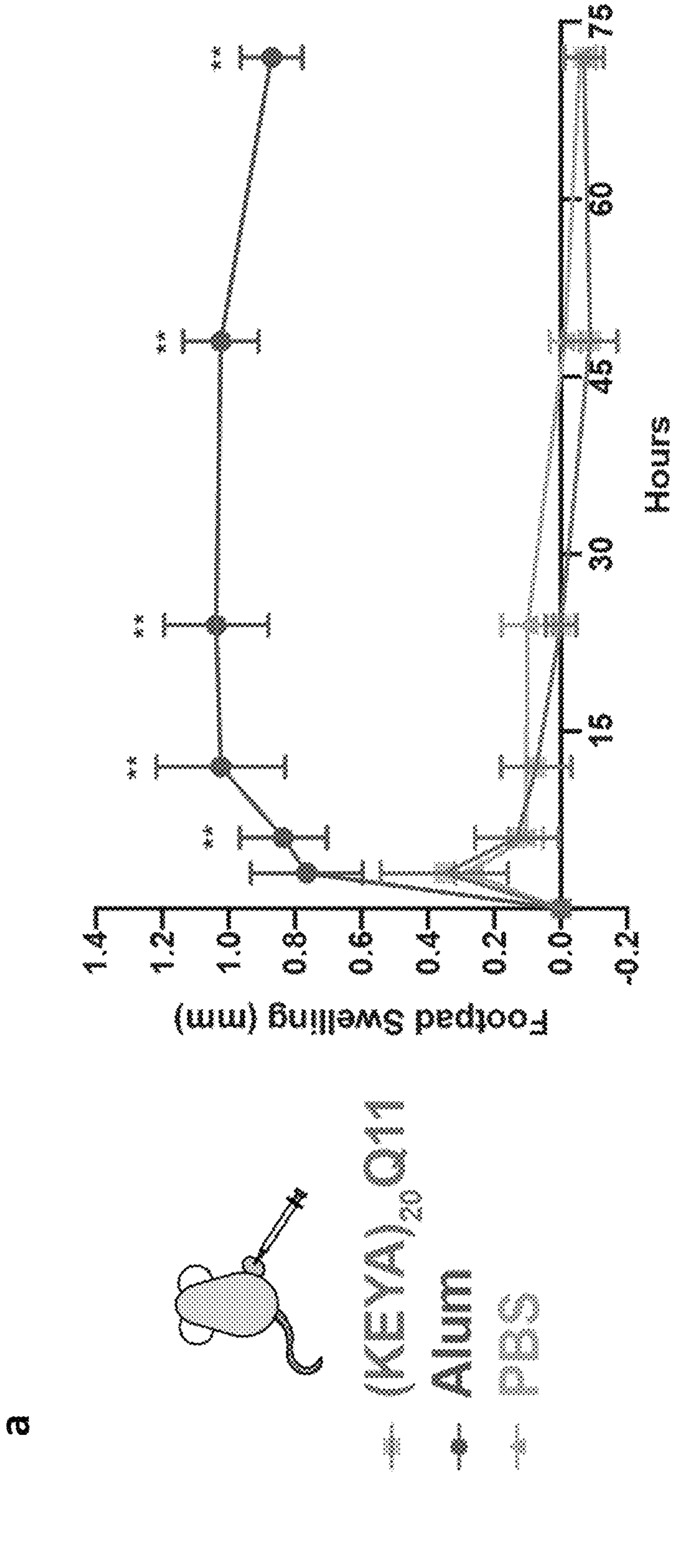
FIG. 7. $(KEYA)_{20}Q11$ does not cause injection site inflammation or increase production of inflammatory cytokines. (a) Footpad swelling measured 3, 6, 12, 24, 48, and 72 hours following a single footpad injection of $(KEYA)_{20}Q11$ (red), Alum (dark gray), or PBS (light gray) and subtracted from baseline measurements. (b) Schematic for 2— or 12-hour i.p. stimulation and lavage with $(KEYA)_{20}Q11$ (red), Q11 (blue), PBS (light gray), PBS+LPS (dark gray). (c) Inflammatory cytokine production following 2-hour i.p. stimulation. (d) Non-inflammatory cytokine production following 12-hour i.p. stimulation. *p<0.05, p<0.01, *p<0.001, ****p<0.0001 by 2way ANOVA with Sidak's post hoc test. Mean+/−s.e.m. shown. n=3-5 experimental replicates per group.
Figure 8:
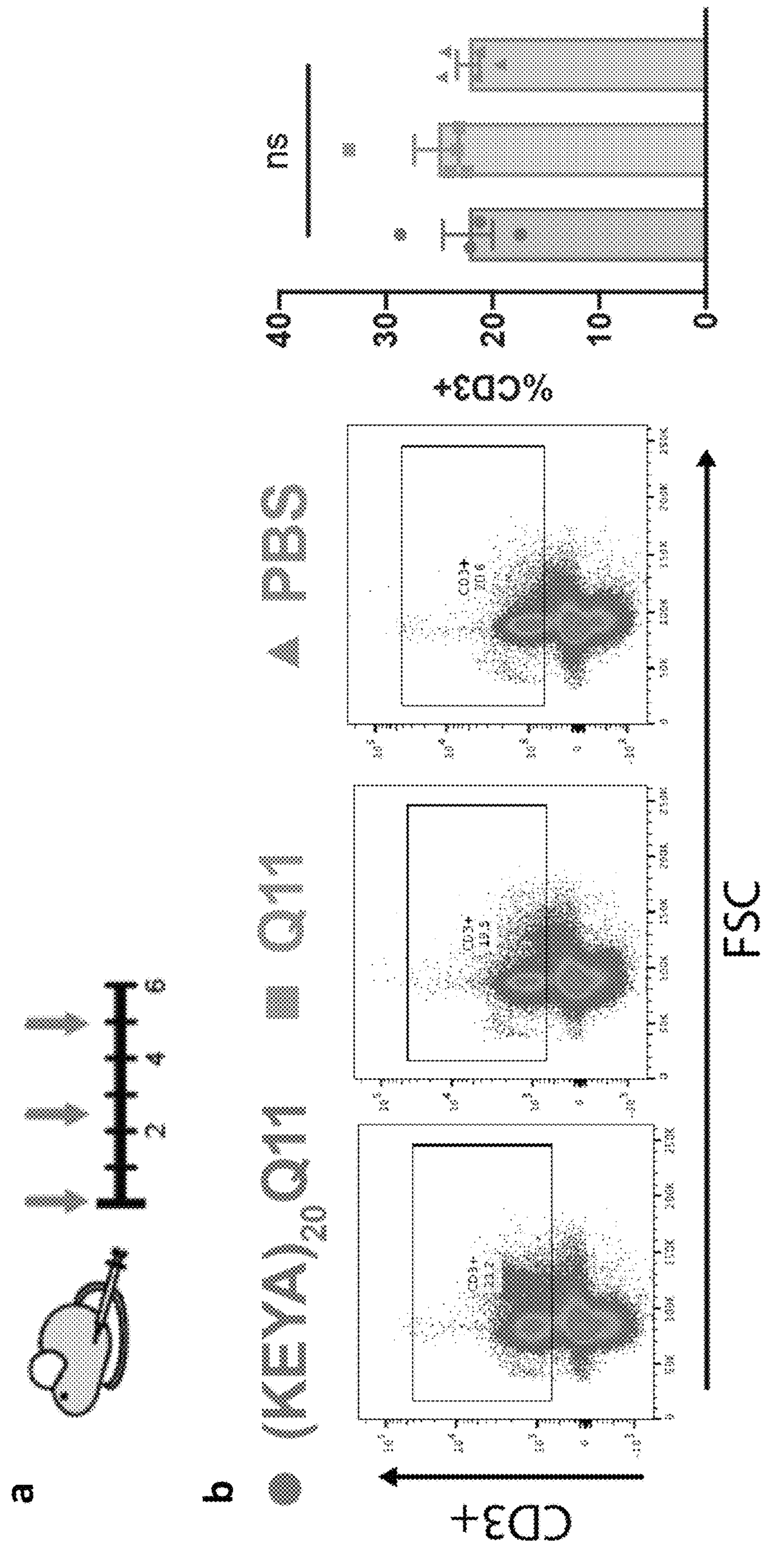
FIG. 8. Immunizations with $(KEYA)_{20}Q11$ lead to increased IL4 production in CD4+ T cells. (a) Cartoon of s.c. immunization schedule with either $(KEYA)_{20}Q11$ (red), Q11 (blue), PBS (gray). Spleens were harvested at week 6. Percent of (b) CD3+ cells and (c) CD3+IL4+ cells from total number of live cells. Percent of (d) CD4+ cells and (e) CD4+IL4+ cells from total number of CD3+ cells. (f) Percent of CD4+CD25 hi cells from total number of CD3+ cells.*p<0.05, *p<0.001, **p<0.0001 by 2way ANOVA with Tukey's post hoc test. Mean+/−s.e.m. shown. n=4-5 experimental replicates per group.
Figure 12:
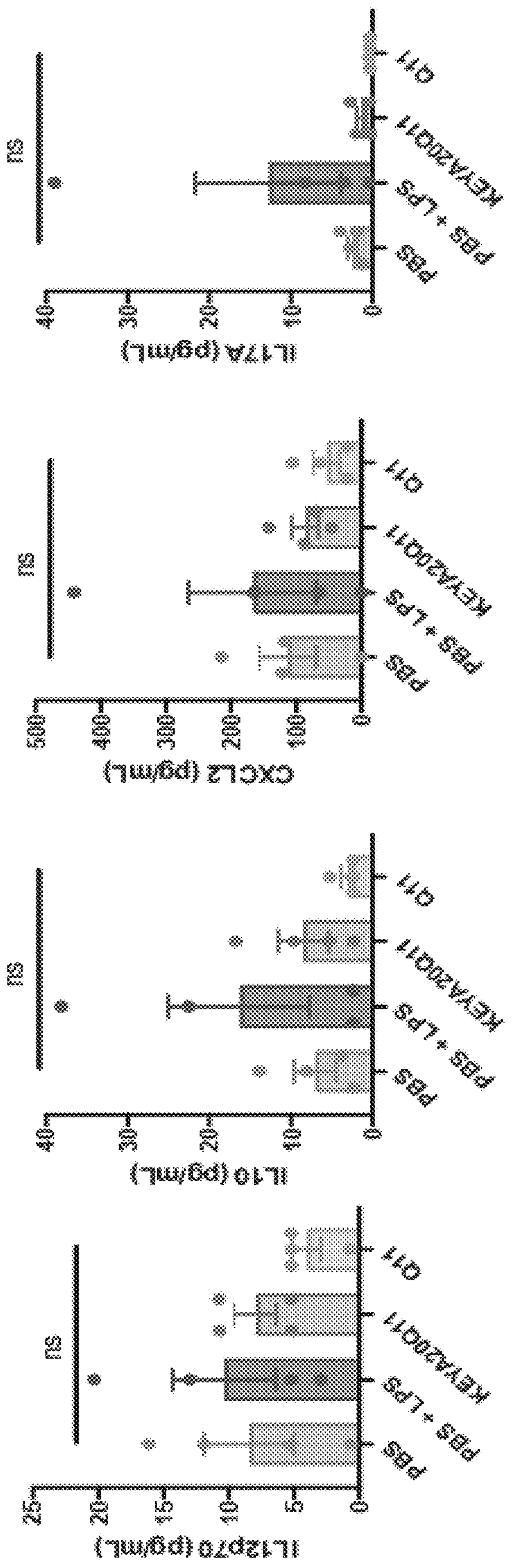
FIG. 12. Graphs showing cytokines examined in the multiplex were not significantly different from PBS.

Immune activation is not mediated by inflammation. To further elucidate why $(KEYA)_{20}$Q11 is an effective immunomodulatory nanomaterial the inventors investigated the potential of inflammation mediated immune engagement. While many adjuvants target local APCs and active the innate immune system by causing inflammation[40], the inventors hypothesized $(KEYA)_{20}$Q11 would not cause inflammation as it has been previously reported that Q11 injections are not inflammatory[32]. Mice were injected subdermally on the back-right footpad with $(KEYA)_{20}$Q11, Alum, or PBS to determine extent of inflammation caused by the nanomaterial (FIG. 7*a*). Alum is a commonly used adjuvant associated with Type 2 immune responses, activate complement, eosinophils, and macrophages but can cause local reactions and inflammation[41]. Footpad swelling was measured over the course of 72 hours and normalized to a pre-injection footpad thickness measurement. An increase in footpad diameter was noticed in all groups at 3 hours and is likely due to remnants of liquid from the injection (FIG. 7*a*). Once the injection volume dissipated, it becomes clear that Alum causes significantly larger swelling in the footpad and that the inflammation is sustained over the course of the experiment (FIG. 7*a*). There is no distinguishable swelling caused by the $(KEYA)_{20}$Q11 injection when compared to the PBS injection (FIG. 7*a*). Delving further into the potential inflammatory response, mice were injected i.p. with $(KEYA)_{20}$Q11, Q11, PBS, or PBS+LPS, an adjuvant that activates innate immunity by displaying pathogen associated molecular patterns, and a multiplex cytokine analysis was performed on the lavage fluid (FIG. 7*b*). Inflammatory cytokines IL1B, IL6, and IFNγ are elevated in response to an LPS injection but remain indistinguishable from PBS after a $(KEYA)_{20}$Q11 or Q11 injection (FIG. 7*c*). Interestingly, anti-inflammatory cytokines IL4 and IL5 were significantly elevated only after a $(KEYA)_{20}$Q11 injection compared to PBS (FIG. 7*d*). IL4 and IL5 are often co-expressed in Th2 cells and are linked to the proliferation and differentiation of T and B cells[42]. The remaining cytokines examined in the multiplex were not significantly different from PBS (FIG. 12). Taken together, the evidence supports the use of $(KEYA)_{20}$Q11 as a non-inflammatory adjuvant with the ability to stimulate IL4 and IL5 production in vivo. Elevated IL4 production after $(KEYA)_{20}$Q11 immunizations. Having established that $(KEYA)_{20}$Q11 does not mediate immune responses through inflammation, the inventors then investigated the effect of $(KEYA)_{20}$Q11 on T cell activation and proliferation as well as the IL4 production of different effector T cell populations. Mice were immunized and boosted twice with $(KEYA)_{20}$Q11, Q11, or PBS (FIG. 68*a*) and their spleens were harvested 5 days after the last boost. After the splenocytes were stimulated overnight with their immunizing peptide, cells were stained and taken to flow cytometry for analysis. The data shows no difference in the total percent of CD3+ cells between groups (FIG. 8*b*), but the cells stimulated with $(KEYA)_{20}$Q11 produced a significantly higher percent of IL4+CD3+ cells (FIG. 8*c*). This indicates that $(KEYA)_{20}$Q11 has no effect on the general proliferation of T cells but instead activates the maturing populations to differentiate into IL4 producing T cells. Moreover, there is a slight reduction in CD4+ T cells after $(KEYA)_{20}$Q11 stimulation (FIG. 8*d*), but again, an increase in the percent of IL4+CD4+ T cells (FIG. 8*e*). The CD4+ T effector population trend is comparable to the CD3+ T cell population in terms of total T cell production and IL4 producing T cells. This indicates that $(KEYA)_{20}$Q11 is potentially only stimulating the expansion of specific IL4 producing T cell populations, theoretically at the expense of other T cell populations. This data is also consistent with the previous ELISpot findings of strong IL4 production from $(KEYA)_{20}$Q11 stimulated lymphocytes (FIGS. 4, 5, 6). Additionally, it is apparent that the Q11 platform significantly increases production of CD4+CD25 hi T cells (FIG. 8*f*), classically considered to be regulatory T cells (Tregs). This detailed analysis of the T cell populations activated by the nanofibers is further evidence for $(KEYA)_{20}$Q11 as a strong Type 2, and specifically, a Th2 T cell polarizing nanomaterial. Moreover, it is clear that $(KEYA)_{20}$Q11 does not influence expansion of T cell populations, potentially beneficial in cases of inflammation. $(KEYA)_{20}$Q11 polarizes the population toward a Th2 T cell phenotype and increases the production of Tregs over PBS immunizations.

Figure 9:
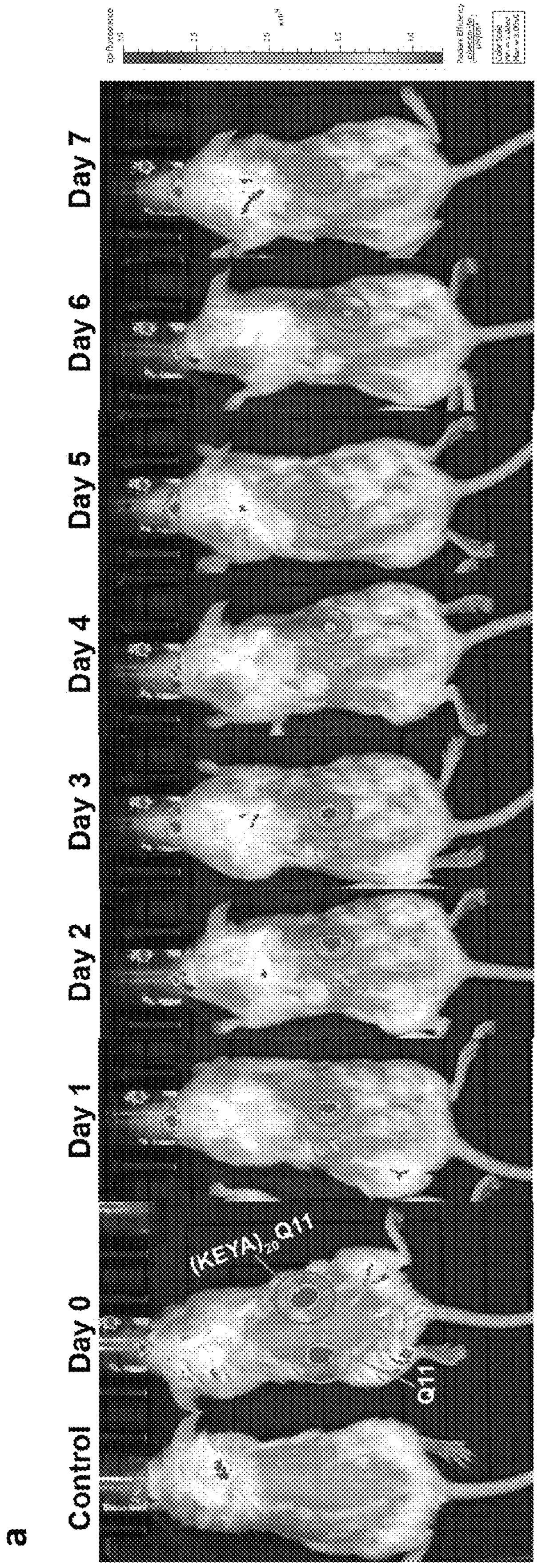
FIG. 9. $(KEYA)_{20}Q11$ persists at the injection site and maintains immunogenicity for up to 7 days. Mice injected with TAMRA labeled Q11 on the left flank and $(KEYA)_{20}Q11$ on the right were (a) measured with IVIS immediately after injection and daily for 7 days. (b) The number of days the fluorescence was detected was graphed to compare the persistence between the two groups. (c) The radiant efficiency was calculated from the images collected and graphed on a log 10 scale. (d) Total amount of remaining nanofiber and (e) overlap between nanofibers and CD45+ cells calculated from confocal images. (f) Representative confocal images from injection site skin collected on Day 7.

Persistence at the injection site. T cell activation hinges on uptake and presentation of nanofiber components by APCs, so we hypothesized that high levels of APC uptake (FIG. 5*a*) of $(KEYA)_{20}$Q11 are responsible for the strong T and B cell response observed above. Uptake by APCs occurs primarily at the s.c. injection site, so we used IVIS to image mice injected with fluorescently labeled nanofibers over the course of a week. Mice were injected with Q11 on their left flank and $(KEYA)_{20}$Q11 on their right (FIG. 9*a*) and images were taken daily to measure the retention of each nanomaterial at the injection site. $(KEYA)_{20}$Q11 persisted an average of 5 days while Q11 was no longer measurable after an average of 3 days (FIG. 9*b*). The more intense radiant efficiency (FIG. 9*c*) also indicates greater amounts of $(KEYA)_{20}$Q11 were retained at the site than Q11 alone. Skin sections were taken of the injection site on day 7 and stained with CD45, a common lymphocyte marker, and DAPI, a common cell nuclei stain (FIG. 9*d-f*). Total amount of nanofiber remaining was quantified by exclusively analyzing the injection site area (FIG. 9*d*), and it was confirmed that more $(KEYA)_{20}$Q11 remained at the injection site when compared to Q11. Moreover, about 6% of the nanofibers overlapped with lymphocytes (FIG. 9*e*), hinting that primed lymphocytes returned to the injection site to be activated. Representative images are shown with their corresponding H&E stained section (FIG. 9*f*) demonstrate full cellular infiltration of the injection site material signifying little to no capsule formation around the injected material. Furthermore, evidence of CD45+ cells at the injection site indicate maintained immunogenicity of $(KEYA)_{20}$Q11 over the course of a week. Clearly, the addition of the randomized $(KEYA)_{20}Q11$ component to the nanofibers dramatically increases retention time at the injection site, critical for maximum APC uptake and downstream immunomodulation. Moreover, a lack of capsule formation allows for full infiltration of the injected material allowing $(KEYA)_{20}Q11$ to continue to interact with lymphocytes and maintain immunogenicity for an extended period of time.

REFERENCES

1. Oany A, Pervin T, Emran A. Design of an epitope-based peptide vaccine against spike protein of human coronavirus: an in silico approach. *DDDT*. August 2014:1139-11. doi:10.2147/DDDT.S67861.
2. Hurtgen B J, Hung C-Y, Ostroff G R, Levitz S M, Cole G T. Construction and Evaluation of a Novel Recombinant T Cell Epitope-Based Vaccine against Coccidioidomycosis. Deepe G S Jr., ed. *Infect Immun.* 2012; 80(11):3960-3974. doi:10.1128/IAI.00566-12.
3. Adar Y, Singer Y, Levi R, et al. A universal epitope-based influenza vaccine and its efficacy against H5N1. *Vaccine.* 2009; 27(15):2099-2107. doi:10.1016/j.vaccine.2009.02.011.
4. Li H-B, Zhang J-Y, He Y-F, et al. Systemic immunization with an epitope-based vaccine elicits a Th1-biased response and provides protection against *Helicobacter pylori* in mice. *Vaccine.* 2012; 31(1):120-126. doi:10.1016/j.vaccine.2012.10.091.
5. Jin X, Newman M J, De-Rosa S, et al. A novel HIV T helper epitope-based vaccine elicits cytokine-secreting HIV-specific CD4+ T cells in a Phase I clinical trial in HIV-uninfected adults. *Vaccine.* 2009; 27(50):7080-7086. doi:10.1016/j.vaccine.2009.09.060.
6. Elliott S L, Suhrbier A, Miles J J, et al. Phase I Trial of a CD8+ T-Cell Peptide Epitope-Based Vaccine for Infectious Mononucleosis. *JVI.* 2008; 82(3):1448-1457. doi:10.1128/JVI.01409-07.
7. Zhang L. The Immunogenicity and Immunoprotection of VBP3 Multi-epitope Vaccine Targeting Angiogenesis and Tumor Inhibition in Lung Cancer-Bearing Mice. *International Journal of Peptide Research and Therapeutics.* 2019; 25(1):215-225. doi:10.1007/s10989-017-9667-4.
8. Onodi F, Maherzi-Mechalikh C, Mougel A, et al. High Therapeutic Efficacy of a New Survivin LSP-Cancer Vaccine Containing CD4+ and CD8+ T-Cell Epitopes. *Front Oncol.* 2018; 8:15-15. doi:10.3389/fonc.2018.00517.
9. Mahdavi M, Moreau V, Kheirollahi M. Identification of B and T cell epitope based peptide vaccine from IGF-1 receptor in breast cancer. *Journal of Molecular Graphics and Modelling.* 2017; 75:316-321. doi:10.1016/j.jmgm.2017.06.004.
10. Zieglmayer P, Focke-Tejkl M, Schmutz R, et al. Mechanisms, safety and efficacy of a B cell epitope-based vaccine for immunotherapy of grass pollen allergy. *EBIOM.* 2016; 11 (C): 43-57. doi:10.1016/j.ebiom.2016.08.022.
11. Xu K, Acharya P, Kong R, et al. Epitope-based vaccine design yields fusion peptide-directed antibodies that neutralize diverse strains of HIV-1. *Nat Med.* June 2018:1-19. doi:10.1038/s41591-018-0042-6.
12. Xu H, Hu C, Gong R, et al. Evaluation of a Novel Chimeric B Cell Epitope-Based Vaccine against Mastitis Induced by Either *Streptococcus agalactiae* or *Staphylococcus aureus* in Mice. *Clin Vaccine Immunol.* 2011; 18(6):893-900. doi:10.1128/CVI.00066-11.
13. Grandi A, Fantappiè L, Irene C, et al. Vaccination With a FAT1-Derived B Cell Epitope Combined With Tumor-Specific B and T Cell Epitopes Elicits Additive Protection in Cancer Mouse Models. *Front Oncol.* 2018; 8:207-214. doi:10.3389/fonc.2018.00481.
14. Alexander J, Sidney J, Southwood S, et al. Development of High Potency Universal DR-Restricted Helper Epitopes by Modification of High Affinity DR-Blocking Peptides. *Immunity.* 1994; 1:751-761.
15. Moutaftsi M, Bui H-H, Peters B, et al. Vaccinia virus-specific CD4+ T cell responses target a set of antigens largely distinct from those targeted by CD8+ T cell responses. *The Journal of Immunology.* 2007; 178(11): 6814-6820. doi:10.4049/jimmunol.178.11.6814.
16. Teitelbaum D, Meshorer A, Hirshfeld T, Arnon R, Sela M. Suppression of experimental allergic encephalomyelitis by a synthetic polypeptide. *Eur J Immunol.* 1971; 1(4):242-248. doi:10.1002/eji.1830010406.
17. Weber M S, Hohlfeld R, Zamvil S S. Mechanism of action of glatiramer acetate in treatment of multiple sclerosis. *Neurotherapeutics.* 2007; 4(4):647-653. doi:10.1016/j.nurt.2007.08.002.
18. Teitelbaum D, Brenner T, Abramsky O, Aharoni R, Sela M, Arnon R. Antibodies to glatiramer acetate do not interfere with its biological functions and therapeutic efficacy. *Mult Scler.* 2003; 9(6):592-599. doi:10.1191/1352458503ms963oa.
19. Vieira P L, Heystek H C, Wormmeester J, Wierenga E A, Kapsenberg M L. Glatiramer Acetate (Copolymer-1, Copaxone) Promotes Th2 Cell Development and Increased IL-10 Production Through Modulation of Dendritic Cells. *The Journal of Immunology.* 2003; 170(9): 4483-4488. doi:10.4049/jimmunol.170.9.4483.
20. Aharoni R. The mechanism of action of glatiramer acetate in multiple sclerosis and beyond. *Autoimmunity Reviews.* 2013; 12(5):543-553. doi:10.1016/j.autrev.2012.09.005.
21. Blanchette F, Neuhaus O. Glatiramer Acetate. *J Neurol.* 2008; 255(S1):26-36. doi:10.1007/s00415-008-1005-5.
22. Weber M S, Prod'homme T, Youssef S, et al. Type II monocytes modulate T cell-mediated central nervous system autoimmune disease. *Nat Med.* 2007; 13(8):935-943. doi:10.1038/nm1620.
23. Neuhaus O, Farina C, Yassouridis A, et al. Multiple sclerosis: Comparison of copolymer-1-reactive T cell lines from treated and untreated subjects reveals cytokine shift from T helper 1 to T helper 2 cells. *Proc Natl Acad Sci USA.* 2000; 97(13):7452-7457.
24. Duda P W, Schmied M C, Cook S L, Krieger J I, Hafler D A. Glatiramer acetate (Copaxone®) induces degenerate, Th2-polarized immune responses in patients with multiple sclerosis. *J Clin Invest.* 2000; 105(7):967-976. doi:10.1172/JCI8970.
25. Aharoni R, Eilam R, Stock A, et al. Glatiramer acetate reduces Th-17 inflammation and induces regulatory T-cells in the CNS of mice with relapsing-remitting or chronic EAE. *Journal of Neuroimmunology.* 2010; 225 (1-2):100-111. doi:10.1016/j.jneuroim.2010.04.022.
26. Sloan-Lancaster J, Allen P M. ALTERED PEPTIDE LIGAND-INDUCED PARTIAL T CELL ACTIVATION: Molecular Mechanisms and Role in T Cell Biology. *Annu Rev Immunol.* 1996; 14:1-27.
27. Aharoni R. Immunomodulatory Therapeutic Effect of Glatiramer Acetate on Several Murine Models of Inflammatory Bowel Disease. *Journal of Pharmacology and Experimental Therapeutics.* 2006; 318(1):68-78. doi:10.1124/jpet. 106.103192.

28. Reick C PhD, M D G E, PhD T T, et al. Expression of brain-derived neurotrophic factor in astrocytes-Beneficial effects of glatiramer acetate in the R6/2 and YAC128 mouse models of Huntington's disease. Experimental Neurology. 2016; 285(Part A): 12-23. doi:10.1016/j.expneurol.2016.08.012.
29. Butovsky O, Koronyo-Hamaoui M, Kynis G, et al. Glatiramer acetate fights against Alzheimer's disease by inducing dendritic-like microglia expressing insulin-like growth factor 1. *PNAS.* 2006; 103(31):11784-11789.
30. Landa G, Butovsky O, Shoshani J, Schwartz M, Pollack A. Weekly Vaccination with Copaxone (Glatiramer Acetate) as a Potential Therapy for Dry Age-Related Macular Degeneration. *Current Eye Research.* 2009; 33(11-12):1011-1013. doi:10.1080/02713680802484637.
31. Rudra J S, Tian Y F, Jung J P, Collier J H. A self-assembling peptide acting as an immune adjuvant. *Proc Natl Acad Sci USA.* 2010; 107(2):622-627. doi:10.1073/pnas.0912124107.
32. Chen J, Pompano R R, Santiago F W, et al. The use of self-adjuvanting nanofiber vaccines to elicit high-affinity B cell responses to peptide antigens without inflammation. *Biomaterials.* 2013; 34(34):8776-8785. doi:10.1016/j.biomaterials.2013.07.063.
33. Pompano R R, Chen J, Verbus E A, et al. Titrating T-Cell Epitopes within Self-Assembled Vaccines Optimizes CD4+ Helper T Cell and Antibody Outputs. *Adv Healthcare Mater.* 2014; 3(11):1898-1908. doi:10.1002/adhm.201400137.
34. Mora-Solano C, Wen Y, Han H, et al. Active immunotherapy for TNF-mediated inflammation using self-assembled peptide nanofibers. *Biomaterials.* 2017; 149:1-11. doi:10.1016/j.biomaterials.2017.09.031.
35. Sohaebuddin S K, Thevenot P T, Baker D, Eaton J W, Tang L. Nanomaterial cytotoxicity is composition, size, and cell type dependent. *Particle and Fibre Toxicology.* 2010; 7(22).
36. Fremont D H, Hendrickson W A, Marrack P, Kappler J. Structures of an MHC Class II molecule with covalently bound single peptides. Science. 1996; 272(5264).
37. Mountford A P, Fisher A, Wilson R A. The profile of IgG1 and IgG2a antibody responses in mice exposed to *Schistosoma mansoni*. Parasite Immunology. 1994; 16:521-527.
38. Gasiorowski J Z, Collier J H. Directed Intermixing in Multicomponent Self-Assembling Biomaterials. *Biomacromolecules.* 2011; 12(10):3549-3558. doi:10.1021/bm200763y.
39. Hengartner H, Zinkernagel R M. The Influence of Antigen Organization on B Cell Responsiveness. *Science.* 1993; 262(5138):1448-1451.
40. OHagan D T, MacKichan M L, Singh M. Recent developments in adjuvants for vaccines against infectious diseases. *Biomolecular Engineering.* 2001; 18:69-75.
41. Gupta R K. Aluminum compounds as vaccine adjuvants. *Advanced Drug Delivery Reviews.* 1998; 32:155-172.
42. Lee J S, Campbell H D, Kozak C A, Young I G. The IL-4 and IL-5 Genes are Closely Linked and Are Part of a Cytokine Gene Cluster on Mouse Chromosome 11. 1989; 15(2):142-152.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

We claim:

1. A polypeptide molecule consisting of a self-assembling polypeptide consisting of SEQ ID NO:1 (Q11) linked to a random polypeptide at least ten amino acids in length, wherein each amino acid in the random polypeptide is independently selected from lysine, glutamic acid, tyrosine, and alanine; and optionally wherein the self-assembling polypeptide is linked to the random polypeptide via a spacer, wherein the spacer is a polypeptide and is at least three amino acids in length and less than 10 amino acids in length.

2. The polypeptide molecule of claim 1, wherein the self-assembling polypeptide is capable of forming nanofibers in solution.

3. The polypeptide molecule of claim 1, wherein the self-assembling polypeptide assembles to form a β-sheet or an α-helix.

4. The polypeptide molecule of claim 1, wherein the random polypeptide is at least 20 amino acids in length.

5. The polypeptide molecule of claim 1, wherein the self-assembling polypeptide is linked to the random polypeptide via a spacer, wherein the spacer is a polypeptide and is at least three amino acids in length and less than 10 amino acids in length.

6. The polypeptide molecule of claim 5, wherein the spacer is a polypeptide is selected from the group consisting of SGSG (SEQ ID NO:68), GGGG (SEQ ID NO: 69), GSGS (SEQ ID NO:70), EAAK (SEQ ID NO:71), EAAAK (SEQ ID NO:72), a poly serine sequence, a poly glycine sequence, a poly alanine sequence, and combinations thereof.

7. The polypeptide molecule of claim 1, wherein at least one of the at least ten amino acids in the random polypeptide is tyrosine.

8. The polypeptide molecule of claim 1, wherein in the random polypeptide at least one of the at least ten amino acids is lysine, at least one of the at least ten amino acids is glutamic acid, at least one of the at least ten amino acids is tyrosine, and at least one of the at least ten amino acids is alanine.

9. A pharmaceutical composition, comprising the polypeptide molecule of claim 1 and a pharmaceutically acceptable carrier or excipient.

10. The pharmaceutical composition of claim 9, further comprising a second polypeptide molecule consisting of a self-assembling peptide consisting of SEQ ID NO: 1 linked to a peptide epitope or antigen.

11. A kit comprising the polypeptide molecule of claim 1 and instructions for use.

12. The pharmaceutical composition of claim 9, wherein the pharmaceutically acceptable carrier or excipient is an isotonic solution, and wherein the self-assembling polypeptide linked to a random polypeptide forms nanofibers in solution.

13. A method of making the polypeptide molecule of claim 1, the method comprising:

(a) creating a self-assembling polypeptide through solid phase peptide synthesis;

(b) optionally linking a spacer onto the self-assembling polypeptide;

(c) creating a random polypeptide by reacting at least three amino acids in equal parts to attach one of the at least three amino acids to the self-assembling polypeptide and optional spacer randomly; and (d) repeating step (c) to add at least 10 amino acids independently selected from lysine, glutamic acid, tyrosine, and alanine to form the polypeptide molecule comprising the random polypeptide linked to the self-assembling polypeptide.

* * * * *

SEQUENCE LISTING

```
<160> NUMBER OF SEQ ID NOS: 92

<210> SEQ ID NO 1
<211> LENGTH: 11
<212> TYPE: PRT
<213> ORGANISM: Artificial Sequence
<220> FEATURE:
<223> OTHER INFORMATION: Synthetic- KEYA Q11

<400> SEQUENCE: 1

Gln Gln Lys Phe Gln Phe Gln Phe Glu Gln Gln
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Synthetic- W-Q11

<400> SEQUENCE: 2
```

```
Trp Gln Gln Lys Phe Gln Phe Gln Phe Glu Gln Gln
1               5                   10


<210> SEQ ID NO 3
<211> LENGTH: 8
<212> TYPE: PRT
<213> ORGANISM: Artificial Sequence
<220> FEATURE:
<223> OTHER INFORMATION: Synthetic- EAK16-I

<400> SEQUENCE: 3

Ala Glu Ala Lys Ala Glu Ala Lys
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic- EAK16-II

<400> SEQUENCE: 4

Ala Glu Ala Glu Ala Lys Ala Lys
1               5


<210> SEQ ID NO 5
<211> LENGTH: 16
<212> TYPE: PRT
<213> ORGANISM: Artificial Sequence
<220> FEATURE:
<223> OTHER INFORMATION: Synthetic- EAK16-IV

<400> SEQUENCE: 5

Ala Glu Ala Glu Ala Glu Ala Glu Ala Lys Lys Glu Ala Lys Lys Glu
1               5                   10                  15


<210> SEQ ID NO 6
<211> LENGTH: 8
<212> TYPE: PRT
<213> ORGANISM: Artificial Sequence
<220> FEATURE:
<223> OTHER INFORMATION: Synthetic- EMK16-II

<400> SEQUENCE: 6

Met Glu Met Glu Met Lys Met Lys
1               5


<210> SEQ ID NO 7
<211> LENGTH: 8
<212> TYPE: PRT
<213> ORGANISM: Artificial Sequence
<220> FEATURE:
<223> OTHER INFORMATION: Synthetic- RAD 16- 1

<400> SEQUENCE: 7

Arg Ala Asp Ala Arg Ala Asp Ala
1               5


<210> SEQ ID NO 8
<211> LENGTH: 8
<212> TYPE: PRT
<213> ORGANISM: Artificial Sequence
<220> FEATURE:
<223> OTHER INFORMATION: Synthetic- RAD16-II

<400> SEQUENCE: 8

Arg Ala Arg Ala Arg Asp Arg Asp
```

1 5

<210> SEQ ID NO 9
<211> LENGTH: 16
<212> TYPE: PRT
<213> ORGANISM: Artificial Sequence
<220> FEATURE:
<223> OTHER INFORMATION: Synthetic- RAD16-IV

<400> SEQUENCE: 9

Arg Ala Arg Ala Arg Ala Arg Ala Arg Asp Arg Asp Arg Asp Arg Asp
1 5 10 15

<210> SEQ ID NO 10
<211> LENGTH: 16
<212> TYPE: PRT
<213> ORGANISM: Artificial Sequence
<220> FEATURE:
<223> OTHER INFORMATION: Synthetic- DAR16-IV

<400> SEQUENCE: 10

Ala Asp Ala Asp Ala Asp Ala Asp Ala Arg Ala Arg Ala Arg Ala Arg
1 5 10 15

<210> SEQ ID NO 11
<211> LENGTH: 4
<212> TYPE: PRT
<213> ORGANISM: Artificial Sequence
<220> FEATURE:
<223> OTHER INFORMATION: Synthetic- KLD16

<400> SEQUENCE: 11

Lys Leu Asp Leu
1

<210> SEQ ID NO 12
<211> LENGTH: 4
<212> TYPE: PRT
<213> ORGANISM: Artificial Sequence
<220> FEATURE:
<223> OTHER INFORMATION: Synthetic- FKFE2

<400> SEQUENCE: 12

Phe Lys Phe Glu
1

<210> SEQ ID NO 13
<211> LENGTH: 4
<212> TYPE: PRT
<213> ORGANISM: Artificial Sequence
<220> FEATURE:
<223> OTHER INFORMATION: Synthetic- EFK12

<400> SEQUENCE: 13

Phe Lys Phe Glu
1

<210> SEQ ID NO 14
<211> LENGTH: 8
<212> TYPE: PRT
<213> ORGANISM: Artificial Sequence
<220> FEATURE:
<223> OTHER INFORMATION: Synthetic- EFK16

<400> SEQUENCE: 14

Phe Glu Phe Glu Phe Lys Phe Lys
1 5

```
<210> SEQ ID NO 15
<211> LENGTH: 20
<212> TYPE: PRT
<213> ORGANISM: Artificial Sequence
<220> FEATURE:
<223> OTHER INFORMATION: Synthetic- MAX1
<220> FEATURE:
<221> NAME/KEY: MISC_FEATURE
<222> LOCATION: (9)..(9)
<223> OTHER INFORMATION: D-valine

<400> SEQUENCE: 15

Val Lys Val Lys Val Lys Val Lys Val Pro Pro Thr Lys Val Lys Val
1               5                   10                  15

Lys Val Lys Val
            20


<210> SEQ ID NO 16
<211> LENGTH: 21
<212> TYPE: PRT
<213> ORGANISM: Artificial Sequence
<220> FEATURE:
<223> OTHER INFORMATION: Synthetic- MAX2 (V16T)
<220> FEATURE:
<221> NAME/KEY: MISC_FEATURE
<222> LOCATION: (9)..(9)
<223> OTHER INFORMATION: D-valine

<400> SEQUENCE: 16

Val Lys Val Lys Val Lys Val Lys Val Asp Pro Pro Thr Lys Val Lys
1               5                   10                  15

Thr Lys Val Lys Val
            20


<210> SEQ ID NO 17
<211> LENGTH: 20
<212> TYPE: PRT
<213> ORGANISM: Artificial Sequence
<220> FEATURE:
<223> OTHER INFORMATION: Synthetic- MAX3 (V7T)
<220> FEATURE:
<221> NAME/KEY: MISC_FEATURE
<222> LOCATION: (9)..(9)
<223> OTHER INFORMATION: D-valine

<400> SEQUENCE: 17

Val Lys Val Lys Val Lys Thr Lys Val Pro Pro Thr Lys Val Lys Thr
1               5                   10                  15

Lys Val Lys Val
            20


<210> SEQ ID NO 18
<211> LENGTH: 20
<212> TYPE: PRT
<213> ORGANISM: Artificial Sequence
<220> FEATURE:
<223> OTHER INFORMATION: Synthetic- MAX4
<220> FEATURE:
<221> NAME/KEY: MISC_FEATURE
<222> LOCATION: (9)..(9)
<223> OTHER INFORMATION: D-lysine

<400> SEQUENCE: 18

Lys Val Lys Val Lys Val Lys Val Lys Pro Pro Ser Val Lys Val Lys
1               5                   10                  15

Val Lys Val Lys
```

```
            20


<210> SEQ ID NO 19
<211> LENGTH: 20
<212> TYPE: PRT
<213> ORGANISM: Artificial Sequence
<220> FEATURE:
<223> OTHER INFORMATION: Synthetic- MAX5 (T12S)
<220> FEATURE:
<221> NAME/KEY: MISC_FEATURE
<222> LOCATION: (9)..(9)
<223> OTHER INFORMATION: D-valine

<400> SEQUENCE: 19

Val Lys Val Lys Val Lys Val Lys Val Pro Pro Ser Lys Val Lys Val
1               5                   10                  15

Lys Val Lys Val
            20


<210> SEQ ID NO 20
<211> LENGTH: 20
<212> TYPE: PRT
<213> ORGANISM: Artificial Sequence
<220> FEATURE:
<223> OTHER INFORMATION: Synthetic- MAX6 (V16E)
<220> FEATURE:
<221> NAME/KEY: MISC_FEATURE
<222> LOCATION: (9)..(9)
<223> OTHER INFORMATION: D-valine

<400> SEQUENCE: 20

Val Lys Val Lys Val Lys Val Lys Val Pro Pro Thr Lys Val Lys Glu
1               5                   10                  15

Lys Val Lys Val
            20


<210> SEQ ID NO 21
<211> LENGTH: 20
<212> TYPE: PRT
<213> ORGANISM: Artificial Sequence
<220> FEATURE:
<223> OTHER INFORMATION: Synthetic- MAX7 (V16C)
<220> FEATURE:
<221> NAME/KEY: MISC_FEATURE
<222> LOCATION: (9)..(9)
<223> OTHER INFORMATION: D-valine

<400> SEQUENCE: 21

Val Lys Val Lys Val Lys Val Lys Val Pro Pro Thr Lys Val Lys Cys
1               5                   10                  15

Lys Val Lys Val
            20


<210> SEQ ID NO 22
<211> LENGTH: 20
<212> TYPE: PRT
<213> ORGANISM: Artificial Sequence
<220> FEATURE:
<223> OTHER INFORMATION: Synthetic- MAX8 (K15E)
<220> FEATURE:
<221> NAME/KEY: MISC_FEATURE
<222> LOCATION: (9)..(9)
<223> OTHER INFORMATION: D-valine

<400> SEQUENCE: 22

Val Lys Val Lys Val Lys Val Lys Val Pro Pro Thr Lys Val Glu Val
1               5                   10                  15
```

Lys Val Lys Val
20

<210> SEQ ID NO 23
<211> LENGTH: 20
<212> TYPE: PRT
<213> ORGANISM: Artificial Sequence
<220> FEATURE:
<223> OTHER INFORMATION: Synthetic- MAX9 (K2E)
<220> FEATURE:
<221> NAME/KEY: MISC_FEATURE
<222> LOCATION: (9)..(9)
<223> OTHER INFORMATION: D-valine

<400> SEQUENCE: 23

Val Glu Val Lys Val Lys Val Lys Val Pro Pro Thr Lys Val Lys Val
1 5 10 15

Lys Val Lys Val
20

<210> SEQ ID NO 24
<211> LENGTH: 20
<212> TYPE: PRT
<213> ORGANISM: Artificial Sequence
<220> FEATURE:
<223> OTHER INFORMATION: Synthetic- MAX10 (K4E)
<220> FEATURE:
<221> NAME/KEY: MISC_FEATURE
<222> LOCATION: (9)..(9)
<223> OTHER INFORMATION: D-valine

<400> SEQUENCE: 24

Val Lys Val Glu Val Lys Val Lys Val Pro Pro Thr Lys Val Lys Val
1 5 10 15

Lys Val Lys Val
20

<210> SEQ ID NO 25
<211> LENGTH: 20
<212> TYPE: PRT
<213> ORGANISM: Artificial Sequence
<220> FEATURE:
<223> OTHER INFORMATION: Synthetic- MAX11 (K6E)
<220> FEATURE:
<221> NAME/KEY: MISC_FEATURE
<222> LOCATION: (9)..(9)
<223> OTHER INFORMATION: D-valine

<400> SEQUENCE: 25

Val Lys Val Lys Val Glu Val Lys Val Pro Pro Thr Lys Val Lys Val
1 5 10 15

Lys Val Lys Val
20

<210> SEQ ID NO 26
<211> LENGTH: 20
<212> TYPE: PRT
<213> ORGANISM: Artificial Sequence
<220> FEATURE:
<223> OTHER INFORMATION: Synthetic- MAX12 (K8E)
<220> FEATURE:
<221> NAME/KEY: MISC_FEATURE
<222> LOCATION: (9)..(9)
<223> OTHER INFORMATION: D-valine

<400> SEQUENCE: 26

Val Lys Val Lys Val Lys Val Glu Val Pro Pro Thr Lys Val Lys Val
1 5 10 15

Lys Val Lys Val
20

<210> SEQ ID NO 27
<211> LENGTH: 20
<212> TYPE: PRT
<213> ORGANISM: Artificial Sequence
<220> FEATURE:
<223> OTHER INFORMATION: Synthetic- MAX13 (K13E)
<220> FEATURE:
<221> NAME/KEY: MISC_FEATURE
<222> LOCATION: (9)..(9)
<223> OTHER INFORMATION: D-valine

<400> SEQUENCE: 27

Val Lys Val Lys Val Lys Val Lys Val Pro Pro Thr Glu Val Lys Val
1 5 10 15

Lys Val Lys Val
20

<210> SEQ ID NO 28
<211> LENGTH: 20
<212> TYPE: PRT
<213> ORGANISM: Artificial Sequence
<220> FEATURE:
<223> OTHER INFORMATION: Synthetic- MAX14 (K17E)
<220> FEATURE:
<221> NAME/KEY: MISC_FEATURE
<222> LOCATION: (9)..(9)
<223> OTHER INFORMATION: D-valine

<400> SEQUENCE: 28

Val Lys Val Lys Val Lys Val Lys Val Pro Pro Thr Lys Val Lys Val
1 5 10 15

Glu Val Lys Val
20

<210> SEQ ID NO 29
<211> LENGTH: 11
<212> TYPE: PRT
<213> ORGANISM: Artificial Sequence
<220> FEATURE:
<223> OTHER INFORMATION: Synthetic- P11-1

<400> SEQUENCE: 29

Gln Gln Arg Gln Gln Gln Gln Gln Glu Gln Gln
1 5 10

<210> SEQ ID NO 30
<211> LENGTH: 11
<212> TYPE: PRT
<213> ORGANISM: Artificial Sequence
<220> FEATURE:
<223> OTHER INFORMATION: Synthetic- P11-2

<400> SEQUENCE: 30

Gln Gln Arg Phe Gln Trp Gln Phe Glu Gln Gln
1 5 10

<210> SEQ ID NO 31
<211> LENGTH: 11
<212> TYPE: PRT
<213> ORGANISM: Artificial Sequence
<220> FEATURE:
<223> OTHER INFORMATION: Synthetic- P11-3

<400> SEQUENCE: 31

```
Gln Gln Arg Phe Gln Trp Gln Phe Gln Gln Gln
1               5                   10


<210> SEQ ID NO 32
<211> LENGTH: 11
<212> TYPE: PRT
<213> ORGANISM: Artificial Sequence
<220> FEATURE:
<223> OTHER INFORMATION: Synthetic- P11-4

<400> SEQUENCE: 32

Gln Gln Arg Phe Glu Trp Glu Phe Glu Gln Gln
1               5                   10


<210> SEQ ID NO 33
<211> LENGTH: 11
<212> TYPE: PRT
<213> ORGANISM: Artificial Sequence
<220> FEATURE:
<223> OTHER INFORMATION: Synthetic- P11-5
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 33

Gln Gln Xaa Phe Xaa Trp Xaa Phe Gln Gln Gln
1               5                   10


<210> SEQ ID NO 34
<211> LENGTH: 11
<212> TYPE: PRT
<213> ORGANISM: Artificial Sequence
<220> FEATURE:
<223> OTHER INFORMATION: Synthetic- P11-7

<400> SEQUENCE: 34

Ser Ser Arg Phe Ser Trp Ser Phe Glu Ser Ser
1               5                   10


<210> SEQ ID NO 35
<211> LENGTH: 11
<212> TYPE: PRT
<213> ORGANISM: Artificial Sequence
<220> FEATURE:
<223> OTHER INFORMATION: Synthetic- P11-8
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 35

Gln Gln Arg Phe Xaa Trp Xaa Phe Glu Gln Gln
1               5                   10


<210> SEQ ID NO 36
<211> LENGTH: 11
```

<212> TYPE: PRT
<213> ORGANISM: Artificial Sequence
<220> FEATURE:
<223> OTHER INFORMATION: Synthetic- P11-9

<400> SEQUENCE: 36

Ser Ser Arg Phe Glu Trp Glu Phe Glu Ser Ser
1 5 10

<210> SEQ ID NO 37
<211> LENGTH: 11
<212> TYPE: PRT
<213> ORGANISM: Artificial Sequence
<220> FEATURE:
<223> OTHER INFORMATION: Synthetic- P11-12
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 37

Ser Ser Arg Phe Xaa Trp Xaa Phe Glu Ser Ser
1 5 10

<210> SEQ ID NO 38
<211> LENGTH: 11
<212> TYPE: PRT
<213> ORGANISM: Artificial Sequence
<220> FEATURE:
<223> OTHER INFORMATION: Synthetic- P11-16
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 38

Asn Asn Arg Phe Xaa Trp Xaa Phe Glu Gln Gln
1 5 10

<210> SEQ ID NO 39
<211> LENGTH: 11
<212> TYPE: PRT
<213> ORGANISM: Artificial Sequence
<220> FEATURE:
<223> OTHER INFORMATION: Synthetic- P11-18
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 39

Thr Thr Arg Phe Xaa Trp Xaa Phe Glu Thr Thr
1 5 10

<210> SEQ ID NO 40
<211> LENGTH: 11
<212> TYPE: PRT
<213> ORGANISM: Artificial Sequence
<220> FEATURE:

<223> OTHER INFORMATION: Synthetic- P11-19
<220> FEATURE:
<221> NAME/KEY: MISC_FEATURE
<222> LOCATION: (5)..(5)
<223> OTHER INFORMATION: X is hydroxyproline
<220> FEATURE:
<221> NAME/KEY: MISC_FEATURE
<222> LOCATION: (7)..(7)
<223> OTHER INFORMATION: X is hydroxyproline

<400> SEQUENCE: 40

Gln Gln Arg Gln Xaa Gln Xaa Gln Glu Gln Gln
1 5 10

<210> SEQ ID NO 41
<211> LENGTH: 16
<212> TYPE: PRT
<213> ORGANISM: Artificial Sequence
<220> FEATURE:
<223> OTHER INFORMATION: Synthetic- 1

<400> SEQUENCE: 41

Phe Glu Phe Glu Phe Lys Phe Lys Phe Glu Phe Glu Phe Lys Phe Lys
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic- 2

<400> SEQUENCE: 42

Phe Glu Phe Glu Ala Lys Phe Lys Phe Glu Phe Glu Phe Lys Phe Lys
1 5 10 15

<210> SEQ ID NO 43
<211> LENGTH: 16
<212> TYPE: PRT
<213> ORGANISM: Artificial Sequence
<220> FEATURE:
<223> OTHER INFORMATION: Synthetic- 3

<400> SEQUENCE: 43

Phe Glu Phe Glu Phe Lys Leu Lys Ile Glu Phe Glu Phe Lys Phe Lys
1 5 10 15

<210> SEQ ID NO 44
<211> LENGTH: 16
<212> TYPE: PRT
<213> ORGANISM: Artificial Sequence
<220> FEATURE:
<223> OTHER INFORMATION: Synthetic- 4

<400> SEQUENCE: 44

Phe Glu Ala Glu Val Lys Leu Lys Leu Glu Leu Glu Val Lys Phe Lys
1 5 10 15

<210> SEQ ID NO 45
<211> LENGTH: 16
<212> TYPE: PRT
<213> ORGANISM: Artificial Sequence
<220> FEATURE:
<223> OTHER INFORMATION: Synthetic- 5

<400> SEQUENCE: 45

Gly Glu Ala Glu Val Lys Leu Lys Ile Glu Leu Glu Val Lys Ala Lys
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: Synthetic- 6

<400> SEQUENCE: 46

Gly Glu Ala Glu Val Lys Ile Lys Ile Glu Val Glu Ala Lys Gly Lys
1 5 10 15

<210> SEQ ID NO 47
<211> LENGTH: 16
<212> TYPE: PRT
<213> ORGANISM: Artificial Sequence
<220> FEATURE:
<223> OTHER INFORMATION: Synthetic- 7

<400> SEQUENCE: 47

Ile Glu Val Glu Ala Lys Gly Lys Gly Glu Ala Glu Val Lys Ile Lys
1 5 10 15

<210> SEQ ID NO 48
<211> LENGTH: 15
<212> TYPE: PRT
<213> ORGANISM: Artificial Sequence
<220> FEATURE:
<223> OTHER INFORMATION: Synthetic- 8

<400> SEQUENCE: 48

Ile Glu Leu Glu Val Lys Ala Lys Gly Glu Ala Glu Lys Leu Lys
1 5 10 15

<210> SEQ ID NO 49
<211> LENGTH: 16
<212> TYPE: PRT
<213> ORGANISM: Artificial Sequence
<220> FEATURE:
<223> OTHER INFORMATION: Synthetic- 9

<400> SEQUENCE: 49

Ile Glu Leu Glu Val Lys Ala Lys Ala Glu Ala Glu Val Lys Leu Lys
1 5 10 15

<210> SEQ ID NO 50
<211> LENGTH: 16
<212> TYPE: PRT
<213> ORGANISM: Artificial Sequence
<220> FEATURE:
<223> OTHER INFORMATION: Synthetic- 10

<400> SEQUENCE: 50

Ile Glu Ala Glu Gly Lys Gly Lys Ile Glu Gly Glu Ala Lys Ile Lys
1 5 10 15

<210> SEQ ID NO 51
<211> LENGTH: 16
<212> TYPE: PRT
<213> ORGANISM: Artificial Sequence
<220> FEATURE:
<223> OTHER INFORMATION: Synthetic- 11

<400> SEQUENCE: 51

Lys Lys Gln Leu Gln Leu Gln Leu Gln Leu Gln Leu Gln Leu Lys Lys
1 5 10 15

<210> SEQ ID NO 52
<211> LENGTH: 14
<212> TYPE: PRT
<213> ORGANISM: Artificial Sequence
<220> FEATURE:
<223> OTHER INFORMATION: Synthetic- 12

<400> SEQUENCE: 52

Glu Gln Leu Gln Leu Gln Leu Gln Leu Gln Leu Gln Leu Glu
1 5 10

<210> SEQ ID NO 53
<211> LENGTH: 16
<212> TYPE: PRT
<213> ORGANISM: Artificial Sequence
<220> FEATURE:
<223> OTHER INFORMATION: Synthetic- 13

<400> SEQUENCE: 53

Lys Lys Ser Leu Ser Leu Ser Leu Ser Leu Ser Leu Ser Leu Lys Lys
1 5 10 15

<210> SEQ ID NO 54
<211> LENGTH: 14
<212> TYPE: PRT
<213> ORGANISM: Artificial Sequence
<220> FEATURE:
<223> OTHER INFORMATION: Synthetic- 14

<400> SEQUENCE: 54

Glu Ser Leu Ser Leu Ser Leu Ser Leu Ser Leu Ser Leu Glu
1 5 10

<210> SEQ ID NO 55
<211> LENGTH: 14
<212> TYPE: PRT
<213> ORGANISM: Artificial Sequence
<220> FEATURE:
<223> OTHER INFORMATION: Synthetic- 15

<400> SEQUENCE: 55

Glu Cys Leu Ser Leu Cys Leu Ser Leu Cys Leu Ser Leu Glu
1 5 10

<210> SEQ ID NO 56
<211> LENGTH: 6
<212> TYPE: PRT
<213> ORGANISM: Artificial Sequence
<220> FEATURE:
<223> OTHER INFORMATION: Synthetic- 16
<220> FEATURE:
<221> NAME/KEY: misc_feature
<222> LOCATION: (4)..(4)
<223> OTHER INFORMATION: X is Q, S, N, G, L or norvaline

<400> SEQUENCE: 56

Ile Ile Ile Xaa Gly Lys
1 5

<210> SEQ ID NO 57
<211> LENGTH: 8
<212> TYPE: PRT
<213> ORGANISM: Artificial Sequence
<220> FEATURE:
<223> OTHER INFORMATION: Synthetic- KFE8

<400> SEQUENCE: 57

Phe Lys Phe Glu Phe Lys Phe Glu
1 5

<210> SEQ ID NO 58
<211> LENGTH: 21
<212> TYPE: PRT
<213> ORGANISM: Artificial Sequence
<220> FEATURE:
<223> OTHER INFORMATION: Synthetic- SLAC

<400> SEQUENCE: 58

Lys Ser Leu Ser Leu Ser Leu Arg Gly Ser Leu Ser Leu Ser Leu Lys
1 5 10 15

Gly Arg Gly Asp Ser
20

<210> SEQ ID NO 59
<211> LENGTH: 14
<212> TYPE: PRT
<213> ORGANISM: Artificial Sequence
<220> FEATURE:
<223> OTHER INFORMATION: Synthetic- Missing-tooth sequence 1

<400> SEQUENCE: 59

Lys Lys Ser Leu Ser Leu Ser Ala Ser Leu Ser Leu Lys Lys
1 5 10

<210> SEQ ID NO 60
<211> LENGTH: 11
<212> TYPE: PRT
<213> ORGANISM: Artificial Sequence
<220> FEATURE:
<223> OTHER INFORMATION: Synthetic- CATCH (+)

<400> SEQUENCE: 60

Gln Gln Lys Phe Lys Phe Lys Phe Lys Gln Gln
1 5 10

<210> SEQ ID NO 61
<211> LENGTH: 11
<212> TYPE: PRT
<213> ORGANISM: Artificial Sequence
<220> FEATURE:
<223> OTHER INFORMATION: Synthetic- CATCH (-)

<400> SEQUENCE: 61

Glu Gln Glu Phe Glu Phe Glu Phe Glu Gln Glu
1 5 10

<210> SEQ ID NO 62
<211> LENGTH: 13
<212> TYPE: PRT
<213> ORGANISM: Artificial Sequence
<220> FEATURE:
<223> OTHER INFORMATION: Synthetic- bQ13

<400> SEQUENCE: 62

Gln Gln Lys Phe Gln Phe Gln Phe Glu Gln Glu Gln Gln
1 5 10

<210> SEQ ID NO 63
<211> LENGTH: 29
<212> TYPE: PRT
<213> ORGANISM: Artificial Sequence
<220> FEATURE:
<223> OTHER INFORMATION: Synthetic- Coil29

<400> SEQUENCE: 63

Gln Ala Arg Ile Leu Glu Ala Asp Ala Glu Ile Leu Arg Ala Tyr Ala
1 5 10 15

Arg Ile Leu Glu Ala His Ala Glu Ile Leu Arg Ala Gln
20 25

<210> SEQ ID NO 64
<211> LENGTH: 13
<212> TYPE: PRT
<213> ORGANISM: Artificial Sequence
<220> FEATURE:
<223> OTHER INFORMATION: Synthetic- PA1

<400> SEQUENCE: 64

Ala Ala Ala Ala Gly Gly Gly Glu Ile Lys Val Ala Val
1 5 10

<210> SEQ ID NO 65
<211> LENGTH: 14
<212> TYPE: PRT
<213> ORGANISM: Artificial Sequence
<220> FEATURE:
<223> OTHER INFORMATION: Synthetic- PA
<220> FEATURE:
<221> NAME/KEY: MISC_FEATURE
<222> LOCATION: (8)..(8)
<223> OTHER INFORMATION: X is phosphoserine

<400> SEQUENCE: 65

Cys Cys Cys Cys Gly Gly Gly Xaa Gly Gly Gly Arg Gly Asp
1 5 10

<210> SEQ ID NO 66
<211> LENGTH: 29
<212> TYPE: PRT
<213> ORGANISM: Artificial Sequence
<220> FEATURE:
<223> OTHER INFORMATION: Synthetic- 17

<400> SEQUENCE: 66

Gln Ala Lys Ile Leu Glu Ala Asp Ala Glu Ile Leu Lys Ala Tyr Ala
1 5 10 15

Lys Ile Leu Glu Ala His Ala Glu Ile Leu Lys Ala Gln
20 25

<210> SEQ ID NO 67
<211> LENGTH: 23
<212> TYPE: PRT
<213> ORGANISM: Artificial Sequence
<220> FEATURE:
<223> OTHER INFORMATION: Synthetic- 18

<400> SEQUENCE: 67

Ala Asp Ala Glu Ile Leu Arg Ala Tyr Ala Arg Ile Leu Glu Ala His
1 5 10 15

Ala Glu Ile Leu Arg Ala Gln
20

<210> SEQ ID NO 68
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 68

Ser Gly Ser Gly
1

<210> SEQ ID NO 69
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 69

Gly Gly Gly Gly
1

<210> SEQ ID NO 70
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 70

Gly Ser Gly Ser
1

<210> SEQ ID NO 71
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 71

Glu Ala Ala Lys
1

<210> SEQ ID NO 72
<211> LENGTH: 5
<212> TYPE: PRT
<213> ORGANISM: Artificial Sequence
<220> FEATURE:
<223> OTHER INFORMATION: Synthetic- spacer sequence

<400> SEQUENCE: 72

Glu Ala Ala Ala Lys
1               5

<210> SEQ ID NO 73
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 73

Ser Gly Ser Gly
1

<210> SEQ ID NO 74
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 74

```
Ser Ser Ser Ser
1


<210> SEQ ID NO 75
<211> LENGTH: 4
<212> TYPE: PRT
<213> ORGANISM: Artificial Sequence
<220> FEATURE:
<223> OTHER INFORMATION: Synthetic- spacer sequence

<400> SEQUENCE: 75

Gly Gly Gly Ser
1


<210> SEQ ID NO 76
<211> LENGTH: 5
<212> TYPE: PRT
<213> ORGANISM: Artificial Sequence
<220> FEATURE:
<223> OTHER INFORMATION: Synthetic- spacer sequence

<400> SEQUENCE: 76

Gly Gly Ala Ala Tyr
1               5


<210> SEQ ID NO 77
<211> LENGTH: 12
<212> TYPE: PRT
<213> ORGANISM: Artificial Sequence
<220> FEATURE:
<223> OTHER INFORMATION: Synthetic- NP T cell epitope
<220> FEATURE:
<221> NAME/KEY: MISC_FEATURE
<222> LOCATION: (1)..(1)
<223> OTHER INFORMATION: A is D-alanine
<220> FEATURE:
<221> NAME/KEY: MISC_FEATURE
<222> LOCATION: (3)..(3)
<223> OTHER INFORMATION: X is cyclohexylalanine
<220> FEATURE:
<221> NAME/KEY: MISC_FEATURE
<222> LOCATION: (13)..(13)
<223> OTHER INFORMATION: A is D-alanine

<400> SEQUENCE: 77

Ala Lys Xaa Val Ala Ala Trp Thr Leu Lys Ala Ala
1               5                   10


<210> SEQ ID NO 78
<211> LENGTH: 15
<212> TYPE: PRT
<213> ORGANISM: Artificial Sequence
<220> FEATURE:
<223> OTHER INFORMATION: Synthetic- NP T cell epitope

<400> SEQUENCE: 78

Gln Val Tyr Ser Leu Ile Arg Pro Asn Glu Asn Pro Ala His Lys
1               5                   10                  15


<210> SEQ ID NO 79
<211> LENGTH: 30
<212> TYPE: PRT
<213> ORGANISM: Artificial Sequence
<220> FEATURE:
<223> OTHER INFORMATION: Synthetic- NP-Q11: NP T cell epitope linked to
      (KEYA)20Q11

<400> SEQUENCE: 79

Gln Val Tyr Ser Leu Ile Arg Pro Asn Glu Asn Pro Ala His Lys Ser
```

```
1               5                   10                  15

Gly Ser Gly Gln Gln Lys Phe Gln Phe Gln Phe Glu Gln Gln
            20                  25                  30


<210> SEQ ID NO 80
<211> LENGTH: 20
<212> TYPE: PRT
<213> ORGANISM: Artificial Sequence
<220> FEATURE:
<223> OTHER INFORMATION: Synthetic- TNF4-23: soluble version of the TNF
      protein

<400> SEQUENCE: 80

Ser Ser Gln Asn Ser Ser Asp Lys Pro Val Ala His Val Val Ala Asn
1               5                   10                  15

His Gln Val Glu
            20


<210> SEQ ID NO 81
<211> LENGTH: 35
<212> TYPE: PRT
<213> ORGANISM: Artificial Sequence
<220> FEATURE:
<223> OTHER INFORMATION: Synthetic- TNF-Q11: TNF4-23 linked to
      (KEYA)20Q11

<400> SEQUENCE: 81

Ser Ser Gln Asn Ser Ser Asp Lys Pro Val Ala His Val Val Ala Asn
1               5                   10                  15

His Gln Val Glu Ser Gly Ser Gly Gln Gln Lys Phe Gln Phe Gln Phe
            20                  25                  30

Glu Gln Gln
        35


<210> SEQ ID NO 82
<211> LENGTH: 60
<212> TYPE: PRT
<213> ORGANISM: Artificial Sequence
<220> FEATURE:
<223> OTHER INFORMATION: Synthetic- random KEYA polypeptide
<220> FEATURE:
<221> NAME/KEY: MISC_FEATURE
<222> LOCATION: (1)..(60)
<223> OTHER INFORMATION: X is randomly selected from K, E, Y, or A
<220> FEATURE:
<221> NAME/KEY: MISC_FEATURE
<222> LOCATION: (5)..(60)
<223> OTHER INFORMATION: optional amino acid

<400> SEQUENCE: 82

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60


<210> SEQ ID NO 83
<211> LENGTH: 5
<212> TYPE: PRT
<213> ORGANISM: Artificial Sequence
<220> FEATURE:
<223> OTHER INFORMATION: Synthetic- random KEYA polypeptide
```

<220> FEATURE:
<221> NAME/KEY: MISC_FEATURE
<222> LOCATION: (1)..(5)
<223> OTHER INFORMATION: X is randomly selected from K, E, Y, or A

<400> SEQUENCE: 83

Xaa Xaa Xaa Xaa Xaa
1 5

<210> SEQ ID NO 84
<211> LENGTH: 10
<212> TYPE: PRT
<213> ORGANISM: Artificial Sequence
<220> FEATURE:
<223> OTHER INFORMATION: Synthetic- random KEYA polypeptide
<220> FEATURE:
<221> NAME/KEY: MISC_FEATURE
<222> LOCATION: (1)..(10)
<223> OTHER INFORMATION: X is randomly selected from K, E, Y, or A

<400> SEQUENCE: 84

Xaa Xaa Xaa Xaa Xaa Xaa Xaa Xaa Xaa Xaa
1 5 10

<210> SEQ ID NO 85
<211> LENGTH: 20
<212> TYPE: PRT
<213> ORGANISM: Artificial Sequence
<220> FEATURE:
<223> OTHER INFORMATION: Synthetic- random KEYA polypeptide
<220> FEATURE:
<221> NAME/KEY: MISC_FEATURE
<222> LOCATION: (1)..(20)
<223> OTHER INFORMATION: X is randomly selected from K, E, Y, or A

<400> SEQUENCE: 85

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa
20

<210> SEQ ID NO 86
<211> LENGTH: 12
<212> TYPE: PRT
<213> ORGANISM: Artificial Sequence
<220> FEATURE:
<223> OTHER INFORMATION: Synthetic- (KEYA)1-Q11
<220> FEATURE:
<221> NAME/KEY: MISC_FEATURE
<222> LOCATION: (1)..(1)
<223> OTHER INFORMATION: X is randomly selected from K, E, Y, or A

<400> SEQUENCE: 86

Xaa Gln Gln Lys Phe Gln Phe Gln Phe Glu Gln Gln
1 5 10

<210> SEQ ID NO 87
<211> LENGTH: 31
<212> TYPE: PRT
<213> ORGANISM: Artificial Sequence
<220> FEATURE:
<223> OTHER INFORMATION: Synthetic- (KEYA)20-Q11
<220> FEATURE:
<221> NAME/KEY: MISC_FEATURE
<222> LOCATION: (1)..(20)
<223> OTHER INFORMATION: X is randomly selected from K, E, Y, or A

<400> SEQUENCE: 87

Xaa Xaa Xaa Xaa Xaa Xaa Xaa Xaa Xaa Xaa Xaa Xaa Xaa Xaa Xaa Xaa 1 5 10 15

Xaa Xaa Xaa Xaa Gln Gln Lys Phe Gln Phe Gln Phe Glu Gln Gln
20 25 30

<210> SEQ ID NO 88
<211> LENGTH: 16
<212> TYPE: PRT
<213> ORGANISM: Artificial Sequence
<220> FEATURE:
<223> OTHER INFORMATION: Synthetic- Missing-tooth sequence 2

<400> SEQUENCE: 88

Lys Lys Ser Leu Ser Leu Ser Ala Ser Ala Ser Leu Ser Leu Lys Lys
1 5 10 15

<210> SEQ ID NO 89
<211> LENGTH: 4
<212> TYPE: PRT
<213> ORGANISM: Artificial Sequence
<220> FEATURE:
<223> OTHER INFORMATION: Synthetic- Exemplary KEYA peptide

<400> SEQUENCE: 89

Glu Glu Lys Tyr
1

<210> SEQ ID NO 90
<211> LENGTH: 4
<212> TYPE: PRT
<213> ORGANISM: Artificial Sequence
<220> FEATURE:
<223> OTHER INFORMATION: Synthetic- Exemplary KEYA peptide

<400> SEQUENCE: 90

Glu Tyr Ala Lys
1

<210> SEQ ID NO 91
<211> LENGTH: 4
<212> TYPE: PRT
<213> ORGANISM: Artificial Sequence
<220> FEATURE:
<223> OTHER INFORMATION: Synthetic- Exemplary KEYA peptide

<400> SEQUENCE: 91

Lys Lys Glu Tyr
1

<210> SEQ ID NO 92
<211> LENGTH: 4
<212> TYPE: PRT
<213> ORGANISM: Artificial Sequence
<220> FEATURE:
<223> OTHER INFORMATION: Synthetic- Exemplary KEYA peptide

<400> SEQUENCE: 92

Ala Glu Lys Tyr
1